(12) United States Patent
Seder et al.

(10) Patent No.: US 12,383,618 B2
(45) Date of Patent: Aug. 12, 2025

(54) EXPRESSION VECTOR DELIVERY SYSTEM AND USE THEREOF FOR INDUCING AN IMMUNE RESPONSE

(71) Applicants: The United States of America, as represented by the Secretary, Department of Health and Human Services, Bethesda, MD (US); The Chancellor, Masters and Scholars of the University of Oxford, Oxford (GB)

(72) Inventors: Robert Seder, Chevy Chase, MD (US); Geoffrey Lynn, Baltimore, MD (US); Leonard Seymour, Oxford (GB)

(73) Assignees: The United States of America, as represented by the Secretary, Department of Health and Human Services, Bethesda, MD (US); The Chancellor, Masters and Scholars of the University of Oxford, Oxford (GB)

( * ) Notice: Subject to any disclaimer, the term of this patent is extended or adjusted under 35 U.S.C. 154(b) by 1258 days.

(21) Appl. No.: 17/064,496

(22) Filed: Oct. 6, 2020

(65) Prior Publication Data
US 2021/0023208 A1    Jan. 28, 2021

Related U.S. Application Data

(62) Division of application No. 15/758,505, filed as application No. PCT/US2016/051037 on Sep. 9, 2016, now Pat. No. 10,799,580.
(Continued)

(51) Int. Cl.
*A61K 39/39*    (2006.01)
*A61K 47/59*    (2017.01)
(Continued)

(52) U.S. Cl.
CPC .............. *A61K 39/39* (2013.01); *A61K 47/59* (2017.08); *A61K 47/6455* (2017.08);
(Continued)

(58) Field of Classification Search
None
See application file for complete search history.

(56) References Cited

U.S. PATENT DOCUMENTS 6,312,727 B1    11/2001    Schacht et al.
10,385,380 B2 *    8/2019    Whitney .................. C12Q 1/37
(Continued)

FOREIGN PATENT DOCUMENTS

WO    WO 2010/128303    11/2010

OTHER PUBLICATIONS

Barouch et al., "A Human T-Cell Leukemia Virus Type 1 Regulatory Element Enhances the Immunogenicity of Human Immunodeficiency Virus Type 1 DNA Vaccines in Mice and Nonhuman Primates," *J Virol.* 79.14: 8828-8834, Jul. 2005.
(Continued)

*Primary Examiner* — Arthur S Leonard
(74) *Attorney, Agent, or Firm* — Klarquist Sparkman, LLP

(57) ABSTRACT

Embodiments of a novel system for delivering an expression vector encoding an antigen to a subject that allows for spatiotemporal control over stimulation of the subject's immune response to the antigen are provided. In some embodiments, the expression vector delivery system includes a polymer linked to an adjuvant in prodrug form that can form polymer nanoparticles and enter a cell (such as an immune cell) under physiological conditions. In some embodiments, the adjuvant is linked to the polymer by an
(Continued)

enzyme degradable labile bond, the cleavage of which activates the adjuvant to stimulate an immune response.

15 Claims, 18 Drawing Sheets

Specification includes a Sequence Listing.

Related U.S. Application Data

(60) Provisional application No. 62/215,927, filed on Sep. 9, 2015.

(51) Int. Cl.
*A61K 47/64* (2017.01)
*A61K 47/65* (2017.01)
*A61K 48/00* (2006.01)
A61K 39/00 (2006.01)

(52) U.S. Cl.
CPC .......... *A61K 47/65* (2017.08); *A61K 48/0041* (2013.01); *A61K 2039/53* (2013.01); *A61K 2039/55511* (2013.01); *A61K 2039/55555* (2013.01); *A61K 2039/6093* (2013.01)

(56) References Cited

U.S. PATENT DOCUMENTS

| | | | |
|---|---|---|---|
| 10,548,988 B2* | 2/2020 | Li | A61K 47/6849 |
| 11,191,821 B2* | 12/2021 | Seder | A61P 35/00 |
| 11,938,177 B2* | 3/2024 | Seder | A61K 9/0019 |
| 2010/0129439 A1 | 5/2010 | Alexis et al. | |
| 2015/0037326 A1 | 2/2015 | Butler-Ransohoff et al. | |
| 2015/0119330 A1 | 4/2015 | McGee et al. | |
| 2015/0328300 A1 | 11/2015 | Zepp et al. | |

OTHER PUBLICATIONS

Czarniecki, "Small Molecule Modulators of Toll-Like Receptors," *J Med Chem.* 51.21: 6621-6626, Nov. 2008.

Davies et al., "The Use of CpG-Free Plasmids to Mediate Persistent Gene Expression Following Repeated Aerosol Delivery of pDNA/PEI Complexes," *Biomaterials* 33.22: 5618-5627, Aug. 2012.

Forde et al., "Development and Characterization of an Enhanced Nonviral Expression Vector for Electroporation Cancer Treatment," *Mol Ther-Methods Clin Dev 1*: 14012, Apr. 2014 (8 pages).

Ganapathi et al., "The Imidazoquinoline Toll-Like Receptor-7/8 Agonist Hybrid-2 Potently Induces Cytokine Production by Human Newborn and Adult Leukocytes," *PLoS One* 10.8: e0134640, Aug. 2015 (12 pages).

Gerster et al., "Synthesis and Structure-Activity-Relationships of 1H-imidazo[4, 5-c]quinolines that Induce Interferon Production," *J Med Chem.* 48.10: 3481-3491, May 2005.

International Search Report and Written Opinion, Issued in International Application No. PCT/US2016/051037, ISA European Patent Office, mailed Jan. 3, 2017, 15 pages.

Lee et al., "DNA Vaccines, Electroporation and their Applications in Cancer Treatment," *Hum Vaccin Immunother.* 11.8: 1889-1900, 2015.

Oh et al., "Enhanced Adjuvanticity of Interleukin-2 Plasmid DNA Administered in Polyethylenimine Complexes," *Vaccine* 27.21-22: 2837-2843, Jun. 2003.

Ryu et al., "Stimulation of Innate Immune Cells by Light-Activated TLR7/8 Agonists," *J Am Chem Soc.* 136.31: 10823-10825, Aug. 2014.

Shukla et al., "Structure-Activity Relationships in Human Toll-Like Receptor 7-Active Imidazoquinoline Analogues," *J Med Chem.* 53.11: 4450-4465, Jun. 2010.

Stone et al., "Nanoparticle-Delivered Multimeric Soluble CD40L DNA Combined with Toll-Like Receptor Agonists as a Treatment for Melanoma," *PLoS One* 4.10: e7334, Oct. 2009 (14 pages).

Thermo Scientific, "Crosslinking Technical Handbook; Easy Molecular Bonding Crosslinking Technology," *Thermo Fisher Scientific*: 1-56, 2012.

Wales et al., "Targeting Intracellular Mediators of Pattern-Recognition Receptor Signaling to Adjuvant Vaccination," *Biochem Soc Trans.* 35: 1501-1503, Dec. 2007.

Yaday et al., "Predicting Immunogenic Tumour Mutations by Combining Mass Spectrometry and Exome Sequencing," *Nature* 515.7528: 572-576, Nov. 2014.

Zauner et al., "Polylysine-Based Transfection Systems Utilizing Receptor-Mediated Delivery," *Adv Drug Deliv Rev.* 30(1-3): 97-113, Mar. 1998.

* cited by examiner

Linker ≡ Enzyme degradable linker with terminal azide

P1-P4 represent any amino acid

Example sequence (R-I-P-K)

DBCO permits attachment to Azide terminated pro-drug TLR-7/8a

Alkyne permits attachment to Azide terminated pro-drug TLR-7/8a

Poly(ethlyenimine) (PEI) polymer carrier

Poly(lysine) (PL) backbone complexes nucleic acids for gene delivery (PL01)

(PL02)

Poly(lysine) (PL) backbone complexes nucleic acids for gene delivery

Poly(lysine) (PL) backbone complexes
nucleic acids for gene delivery

FIG. 10B
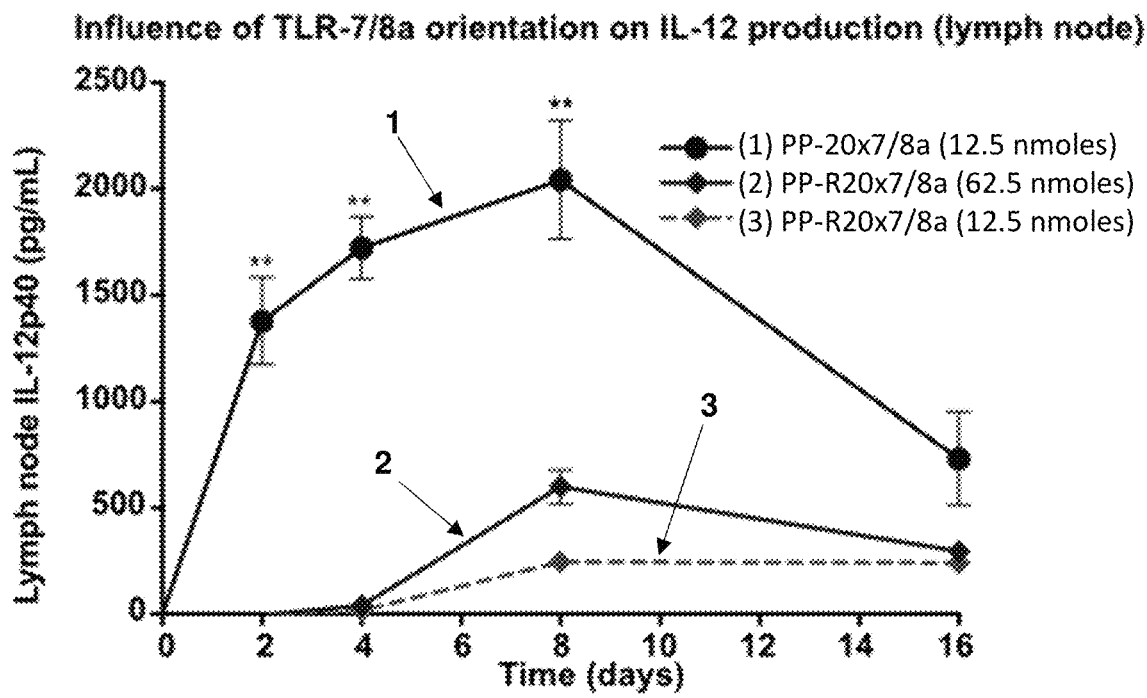
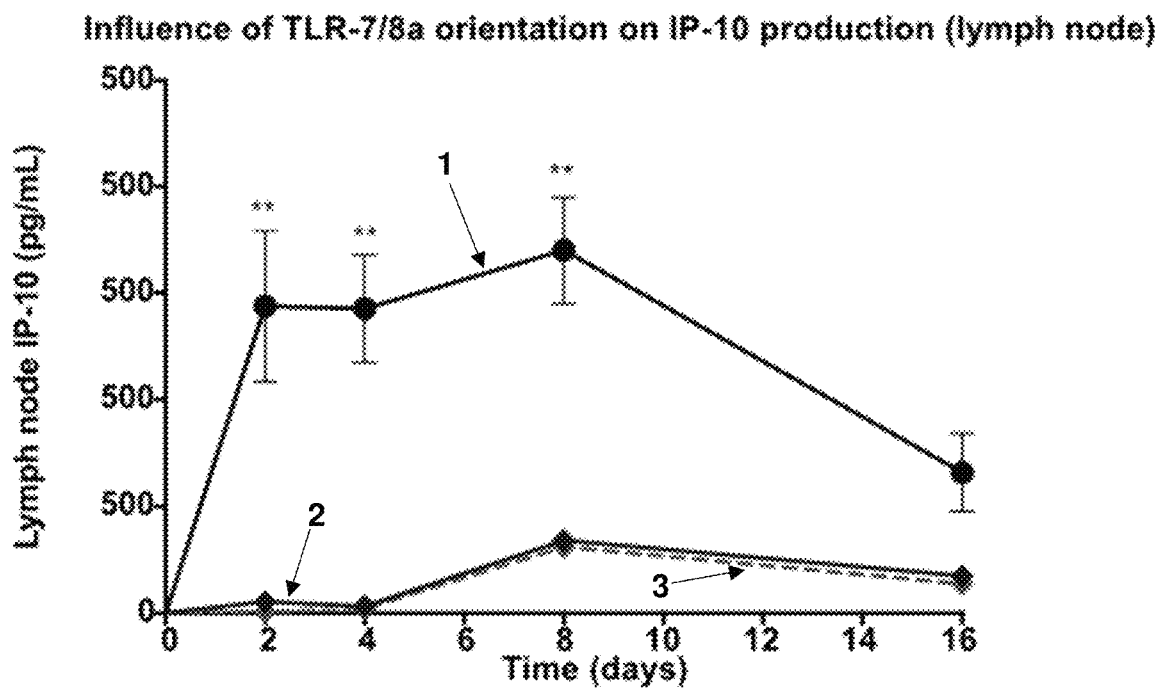
FIG. 10C

In vivo cytokine kinetic for prodrug TLR-7/8a (1)

EC50 for TLR-7
(in vitro): 0.02 µM (4)

EC50 for TLR-7
(in vitro): 0.87 µM (13)

EC50 for TLR-7
(in vitro): 9.36 µM (14)

EC50 for TLR-7
(in vitro): 0.13 µM (15)

EC50 for TLR-7
(in vitro): 0.11 µM (16)

EC50 for TLR-7
(in vitro): 2.17 µM

EXPRESSION VECTOR DELIVERY SYSTEM AND USE THEREOF FOR INDUCING AN IMMUNE RESPONSE

CROSS REFERENCE TO RELATED APPLICATIONS

This is a divisional of U.S. patent application Ser. No. 15/758,505, filed Mar. 8, 2018, which is the U.S. National Stage of International Application No. PCT/US2016/051037, filed Sep. 9, 2016, which was published in English under PCT Article 21(2), which in turn claims the benefit of U.S. Provisional Application No. 62/215,927, filed Sep. 9, 2015. Each of the prior applications is incorporated by reference herein in their entirety.

FIELD OF THE DISCLOSURE

This relates to embodiments of a novel system for delivering an expression vector encoding an antigen to a subject that allows for spatiotemporal control over stimulation of the subject's immune response to the antigen.

BACKGROUND

DNA and RNA based vaccines provide a flexible approach for expressing antigens for stimulating immune responses against infectious agents or cancers. However, a limitation of DNA and RNA-based vaccination approaches is that the nucleic acids used to express transgenic antigen are weakly immunogenic. To improve immune responses, DNA and RNA based vaccines can be combined with adjuvants, such as Toll-like receptor (TLR) agonists that enhance immune responses to the transgenic antigen. Adjuvants can enhance an immune response to an antigen expressed from a nucleic acid-based expression vector, such as a DNA or RNA plasmid vector. However, the immune response stimulated by the adjuvant can directly target the expression vector itself. This negative feedback leads to reduced antigen expression, and ultimately a reduced antigen-targeted T-cell response. Thus, to improve T cell responses to an antigen encoded by a nucleic acid-based expression vector, there is a need for adjuvants that enhance an immune response only after adequate antigen expression from the vector has occurred.

SUMMARY

Disclosed herein are embodiments of a novel system for delivering an expression vector encoding an antigen to a subject that allows for spatiotemporal control over activation of the subject's immune response to the antigen. The delivery system includes a polymer linked to an adjuvant in prodrug form. In several embodiments, the adjuvant prodrug includes a functional moiety required for adjuvant activity that is masked by connection via an enzyme-degradable labile bond to a progroup, to the polymer, or to a linker connected to the polymer. Masking of the functional moiety ablates adjuvant activity to form the adjuvant prodrug.

The expression vector can be complexed with the polymer to form polymer nanoparticles that can be taken up into cells (for example, taken up into the endosomal compartment of immune cells, such as antigen presenting cells) following administration to a subject. Within the cell, the antigen encoded by the nucleic acid molecule on the expression vector is expressed, and the adjuvant prodrug is processed to the active form of the adjuvant. Processing to generate the active adjuvant is slow enough to delay adjuvant-induced immune activation until after the antigen encoded by the expression vector is expressed by the cell. This spatiotemporal control over immune stimulation allows for optimal innate immune stimulation (by the adjuvant) without limiting expression of the antigen due to innate signaling pathways shutting down gene expression or adaptive immune responses targeting the foreign nucleotides or antigen expressed by the expression vector itself.

In some embodiments, a method of inducing an immune response to an antigen in a subject is provided. The method can comprise administering to a target location in the subject a therapeutically effective amount of an immunogenic composition comprising a polymer linked to an adjuvant prodrug (such as a prodrug Toll-like receptor (TLR)-7/8 agonist) and an expression vector (for example, a DNA or RNA plasmid expression vector) comprising a nucleic acid molecule encoding the antigen. The polymer linked to the adjuvant prodrug and the expression vector are in the form of polymer nanoparticles in the immunogenic composition. The polymer nanoparticles can enter cells under physiological conditions. The adjuvant prodrug comprises an enzyme-degradable labile bond, and cleavage of the enzyme-degradable labile bond by an intracellular enzyme activates the adjuvant prodrug to induce the immune response to the antigen in the subject.

In some embodiments of the disclosed methods, the adjuvant prodrug is linked to a linker by the enzyme-degradable labile bond and the linker is linked to the polymer, and cleavage of the enzyme-degradable labile bond by the intracellular enzyme activates the adjuvant and releases the adjuvant from the polymer. In several embodiments, the enzyme-degradable labile bond is a protease-cleavable labile bond, and cleavage of the protease-cleavable labile bond by an intracellular protease (such as cathepsin) activates the adjuvant to induce the immune response against the antigen in the subject.

In additional embodiments of the disclosed methods, the adjuvant prodrug can be activated to enhance the immune response from 1-10 days (such as 5-10 days) following administration of the immunogenic composition to the subject. In some embodiments, the adjuvant prodrug is not activated to enhance the immune response until after the nucleic acid molecule encoding the antigen is expressed in the subject.

In some embodiments of the disclosed methods, the polymer can be a cationic polymer such as a poly(ethylenimine) polymer, a poly(lysine) polymer, or a poly(arginine) polymer. In several embodiments, the polymer can be a cationic polymer (that is, a polymer with a predominantly positive charge) and the expression vector is linked to the cationic polymer by an electrostatic interaction. In several embodiments, the expression vector can be a non-immunogenic expression vector, such as a DNA expression vector that does not contain any CpG motifs.

In some embodiments of the disclosed methods, the polymer can be a hydrophilic polymer with neutral charge, such as a poly(N-(2-hydroxypropyl(methacrylamide)) (pHPMA)-based co-polymer, wherein the polymer is linked to an adjuvant prodrug (such as a prodrug TLR-7/8 agonist) through a linker group. The hydrophilic prodrug adjuvant can be comprised of unimolecular polymer coils or can be induced to form particles. In several embodiments, the hydrophilic adjuvant that does not carry high positive charge density can be admixed with an expression vector, such as a DNA expression vector that does not contain any CpG motifs.

In some embodiments of the disclosed methods, the ratio of adjuvant prodrug to monomer of the polymer is from 1:100 to 1:1 mol/mol, optionally wherein the ratio of adjuvant prodrug to monomer of the polymer is from 1:20 to 1:10 mol/mol.

In some embodiments, the expression vector delivery system includes a cationic polymer (such as poly(lysine) or poly(ethylenimine)) linked to a TLR-7/8 agonist. The cationic polymer can interact with an expression vector (such as a RNA or DNA plasmid) by electrostatic interaction to form polymer nanoparticles that can be administered to a subject and taken up by cells (such as immune cells, for example, antigen presenting cells) to mediate expression of an antigen encoded by the expression vector. The TLR-7/8 agonist includes an amine or hydrazine group required for adjuvant activity that is masked by connection by an enzyme-degradable labile bond to a progroup, to the cationic polymer, or to a linker connected to the cationic polymer, to form the adjuvant prodrug with ablated adjuvant activity. In embodiments wherein the TLR-7/8 agonist is joined by the enzyme-degradable labile bond to the cationic polymer or to the linker connected to the cationic polymer, cleavage of the enzyme-degradable labile bond (for example, by an intracellular hydrolase or protease, such as a cathepsin) connecting the adjuvant to the polymer (or linker) releases the adjuvant from the polymer (or linker) and converts the adjuvant to an active structure. In embodiments wherein the TLR-7/8 agonist is joined by the enzyme-degradable labile bond to the progroup, cleavage of the enzyme-degradable labile bond (for example, by an intracellular hydrolase or protease, such as a cathepsin) connecting the adjuvant to the progroup converts the adjuvant to an active structure. In several such embodiments, when the expression vector and delivery system are administered to a subject, the prodrug TLR-7/8 agonist is not activated to enhance the immune response until after the nucleic acid molecule encoding the antigen is expressed in the subject.

In further embodiments, a compound, or a pharmaceutically acceptable salt thereof, comprising a structure with TLR-7/8 agonist activity is provided, such as a compound with the structure of any one of Compounds 13 or 16-28.

The foregoing and other features and advantages of this disclosure will become more apparent from the following detailed description of several embodiments, which proceeds with reference to the accompanying figures.

BRIEF DESCRIPTION OF THE FIGURES

FIGS. 10A-10C show a set of molecular structures and graphs illustrating that the orientation of the TLR-7/8a attached to the polymer carrier can influence the timing of onset and magnitude of lymph node cytokine production in vivo. (10A) polymer nanoparticles including polymer linked to a TLR-7/8s were prepared with the TLR-7/8a attached to the polymer carrier with either the C4-amine exposed (PP-20×7/8a) or blocked (PP-R20×7/8a). "PP" refers to polymer nanoparticle. The linkage of the TLR-7/8a to the polymer in PP-R20×7/8a did not include a cathepsin-cleavable linker. (10B, 10C) the polymer nanoparticles including the polymer/TLR-7/8a conjugates were administered subcutaneously into the hind footpads of C57BL/6 mice and lymph nodes (n=4) were isolated at serial time points thereafter and cultured overnight. Supernatant from the ex vivo lymph node cell suspensions (n=4) were evaluated for (b) IL-12 and (c) IP-10 by ELISA. Blocking the C4-amine delayed onset and lowered the magnitude of cytokine production. All data are reported as mean±SEM; significance is relative to all other groups (ANOVA with Bonferroni correction); ns, not significant ($P>0.05$); *, $P<0.05$; **, $P<0.01$.

As shown in FIG. 11, the polymers linked to the TLR-7/8a with the C4-amine exposed induce high magnitude immune responses by day one, indicating rapid onset of immune activation.

As shown in FIG. 12, the polymers linked to the pro-drug TLR-7/8a did not induce immune activation (>2× S.D of responses by polymer alone, ~400 pg/mL IL-12) until between 2 and 7 days after administration

SEQUENCE LISTING

Figure 1:
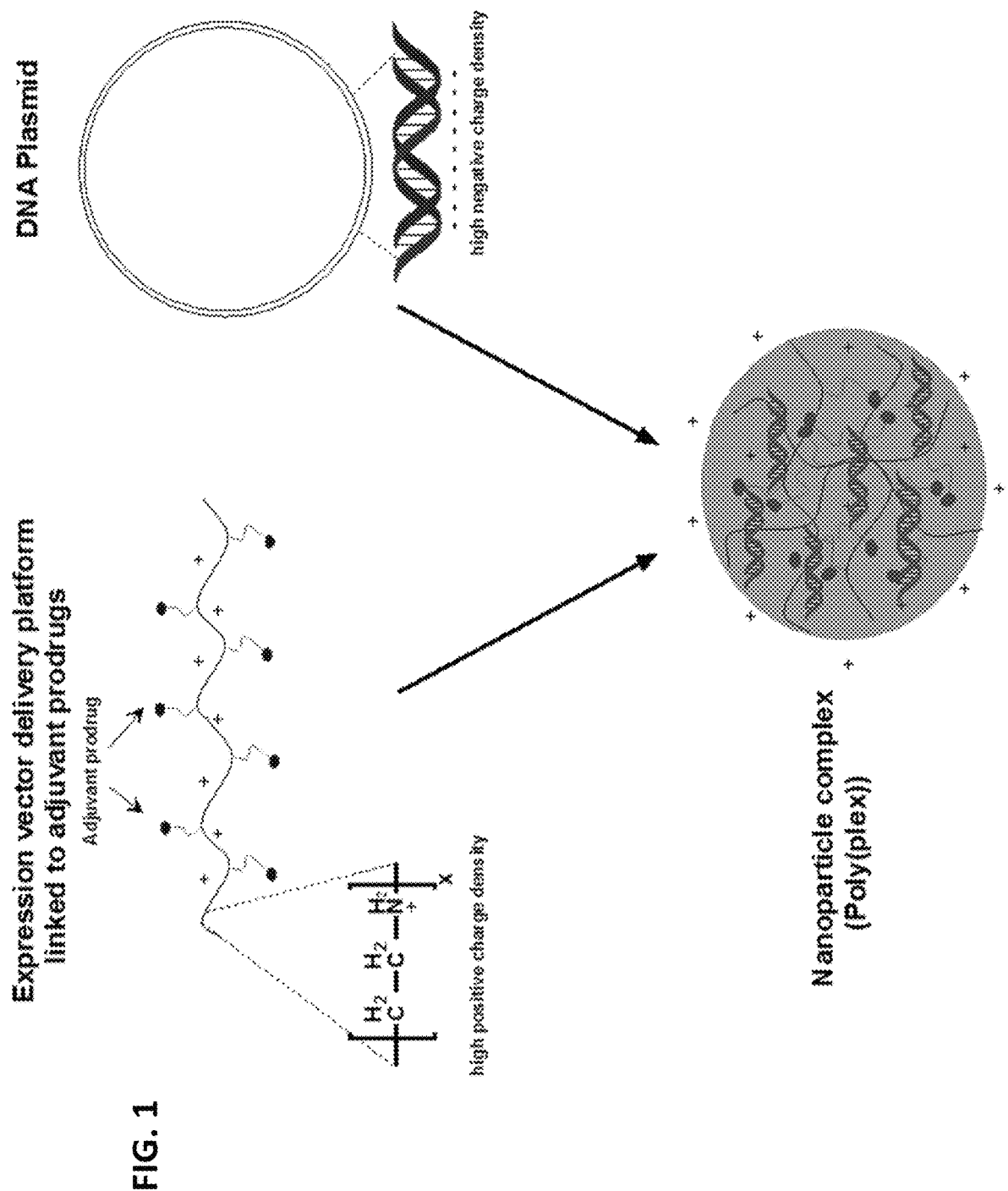
FIG. 1 is a cartoon schematic illustrating embodiments of the system for delivering an expression vector encoding an antigen to a subject. On the left, an expression vector delivery system comprised of a positively charged (cationic) polymer linked to an adjuvant prodrug can be linked with a negatively charged (anionic) DNA-based expression vector to form a nanoparticle complex of the two materials that is held together (i.e., linked) through electrostatic interactions.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~1 kb), which was created on Aug. 25, 2020, which is incorporated by reference herein.

DETAILED DESCRIPTION

Disclosed herein are embodiments of a novel system for delivering an expression vector encoding an antigen to a subject that allows for spatiotemporal control over activation of the subject's immune response to the antigen. The delivery system includes a polymer linked to an adjuvant in prodrug form. The expression vector can be complexed with the polymer to form polymer nanoparticles that can be taken up into cells (for example, taken up into the endosomal compartment of immune cells, such as an antigen presenting cells) following administration to a subject. Within the cell, the antigen encoded by the nucleic acid molecule on the expression vector is expressed, and the adjuvant prodrug is processed to the active form of the adjuvant. Processing to generate the active adjuvant is slow enough to delay adjuvant-induced immune activation until after the antigen encoded by the expression vector is expressed by the cell. By local (such as intramuscular) administration of the polymer nanoparticles including the expression vector complexed with the polymer, the therapeutic agent remains primarily localized near the site of administration (for example, at the administration site, and in lymph nodes near the administration site).

Accordingly, the polymeric delivery system can control the pharmacokinetics of the prodrug adjuvant. The delivery system enhances retention of the prodrug adjuvant near the site of injection and draining lymphatics, and also promotes uptake by immune cells. The polymer carrying the prodrug adjuvant can be a cationic polymer that can complex DNA or RNA and be used to form a nanoparticle poly(plex) that is able to deliver the prodrug and genetic material. Alternatively, the polymer carrying the prodrug PRR agonist can simply be co-administered with RNA, DNA or viral based gene delivery systems. As described herein, this spatiotemporal control over immune stimulation allows for optimal innate immune stimulation (by the adjuvant) without innate signaling pathways shutting down gene expression or adaptive immune responses targeting the foreign nucleotides or antigen expressed by the expression vector itself.

I. Terms

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

About: Plus or minus 5% from a set amount. For example, "about 5" refers to 4.75 to 5.25. A ratio of "about 5:1" refers to a ratio of from 4.75:1 to 5.25:1.

Acyl: A group having the structure —C(O)R, where R may be, for example, optionally substituted alkyl, optionally substituted aryl, or optionally substituted heteroaryl. Lower acyl groups are those that contain one to six carbon atoms.

Adjuvant: Any material added to vaccines to enhance the immunogenicity of an antigen. Adjuvants can include a suspension of minerals (alum, aluminum hydroxide, or phosphate) on which antigen is adsorbed; or water-in-oil emulsion, for example, in which antigen solution is emulsified in mineral oil (Freund's incomplete adjuvant), sometimes with the inclusion of killed mycobacteria (Freund's complete adjuvant) to further enhance immunogenicity (inhibits degradation of antigen and/or causes influx of macrophages) Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and Toll-like receptor (TLR) agonists, such as TLR-7/8 agonists. The person of ordinary skill in the art is familiar with adjuvants (see, e.g., Singh (ed.) Vaccine Adjuvants and Delivery Systems. Wiley-Interscience, 2007).

Adjuvant Prodrug: A derivative of an active adjuvant that requires a transformation under the conditions of use, such as within the body, to release the active adjuvant. Until converted into the active adjuvant, adjuvant prodrugs are pharmacologically inactive or have substantially reduced pharmacological activity (such as less than 90%) compared to the active adjuvant.

Adjuvant prodrugs may be prepared by linking a functional moiety on the adjuvant that is required for adjuvant activity to a progroup, linker, or other compound in such a way that the modified adjuvant lacks (or has substantially reduced) adjuvant activity, and where cleavage of the progroup, linker, or other compound in vivo produces the active form of the adjuvant. For example, Adjuvant prodrugs can be obtained by masking one or more functional moieties in an active adjuvant at least in part required for adjuvant activity with a progroup to form the adjuvant prodrug. The adjuvant prodrug undergoes a transformation, such as cleavage of the progroup from the functional moiety, under the specified conditions of use to unmask the functional moiety, to release the active adjuvant. The cleavage of the progroup may proceed spontaneously, such as by way of a hydrolysis reaction, or it may be catalyzed or induced by another agent, such as by an enzyme, by acid or base, or by a change of or exposure to a physical or environmental parameter, such as a change of temperature. The agent is typically endogenous to the conditions of use, such as an enzyme present in the cells to which the prodrug is administered or the acidic conditions of a cellular compartment (such as the lysosome).

A progroup is a type of protecting group that, when used to mask a functional moiety within an active adjuvant, converts the adjuvant into a prodrug adjuvant. Progroups are typically attached to the functional moiety of the drug via bonds that are cleavable under specified conditions of use. As a specific example, for an adjuvant prodrug with a amide or hydrazine functional moiety, the functional moiety masked by the progroup can comprise the formula —NH—C(O)—R or —NH—NH—C(O)—R wherein the progroup comprises —C(O)R.

Administration: To provide or give to a subject an agent, for example, a composition including polymer nanoparticles comprised of an expression vector delivery system complexed with an expression vector encoding an antigen as described herein, by any effective route. Exemplary routes of administration include, but are not limited to, oral, injection (such as subcutaneous, electroporation (such as by endoscope electroporation), intramuscular, intradermal, intraperitoneal, and intravenous), sublingual, rectal, transdermal (for example, topical), intranasal, vaginal, and inhalation routes. In some embodiments, the polymer nanoparticles including the adjuvant prodrug can be co-administered with the expression vector (e.g., by administering an admixed composition) and intracellular delivery of the expression vector can be accomplished using endoscopic electroporation.

Aliphatic: A group including alkyl, alkenyl, alkynyl, halogenated alkyl and cycloalkyl groups. A lower aliphatic group is a branched or unbranched aliphatic group having from 1 to 10 carbon atoms.

Alkenyl: A cyclic, branched or straight chain group containing only carbon and hydrogen, and contains one or more double bonds that may or may not be conjugated. Alkenyl groups may be unsubstituted or substituted. Lower alkenyl groups contain one to six carbon atoms.

Alkoxy: A straight, branched or cyclic hydrocarbon configuration and combinations thereof, including from 1 to 20 carbon atoms, preferably from 1 to 6 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

Alkoxycarbonyl: An alkoxy substituted carbonyl radical, —C(O)OR, wherein R represents an optionally substituted alkyl, aryl, aralkyl, cycloalkyl, cycloalkylalkyl or similar moiety.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A lower alkyl group is a saturated branched or unbranched hydrocarbon having from 1 to 6 carbon atoms. Preferred alkyl groups have 1 to 4 carbon atoms. Alkyl groups may be substituted alkyls wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

Alkynyl: A cyclic, branched or straight chain group containing only carbon and hydrogen, and unless otherwise mentioned typically contains one to twelve carbon atoms, and contains one or more triple bonds. Alkynyl groups may be unsubstituted or substituted. A lower alkynyl group is one that contains one to six carbon atoms.

Amine or Amino: A group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

Aminoalkyl: An alkyl group as defined above where at least one hydrogen atom is replaced with an amino group (e.g., —$CH_2$—$NH_2$).

Aminocarbonyl: A group that, alone or in combination, includes an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

Amide or Amido: A group that is represented by the formula —C(O)NRR', where R and R' independently can be a hydrogen, alkyl, alkenyl, alkynyl, aryl, aralkyl, cycloalkyl, halogenated alkyl, or heterocycloalkyl group.

Analog: A molecule that differs in chemical structure from a parent compound, for example, a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

Antigen: A polypeptide or portion thereof that can stimulate the production of antibodies or a T cell response in an animal. An antigen reacts with the products of specific humoral or cellular immunity, including those induced by heterologous antigens. In some examples, an antigen can include a polypeptide from a pathogen of interest (such as a virus) or a diseased tissue of interest (such as a tumor). An antigen that can stimulate the production of antibodies or a T cell response in a subject to a polypeptide expressed by a virus is a viral antigen. An antigen that can stimulate the production of antibodies or a T cell response in a subject to a polypeptide primarily expressed by tumor tissue, but not healthy tissue, is a tumor associated antigen.

Antigen-presenting cell (APC): A cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

Aralkyl: An alkyl group wherein an aryl group is substituted for a hydrogen of the alkyl group. An example of an aralkyl group is a benzyl group.

Aryl: A monovalent unsaturated aromatic carbocyclic group having a single ring (e.g., phenyl) or multiple condensed rings (e.g., naphthyl or anthryl), which can optionally be unsubstituted or substituted. A heteroaryl group is an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

Aryloxy or Heteroaryloxy: A group of the formula —OAr, wherein Ar is an aryl group or a heteroaryl group, respectively.

Carboxylate or Carboxyl: The group —COO$^-$ or —COOH. The carboxyl group can form a carboxylic acid. A substituted carboxyl is a —COOR group where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

Cycloalkyl: A non-aromatic carbon-based ring composed of at least three carbon atoms. Examples of cycloalkyl groups include, but are not limited to, cyclopropyl, cyclobutyl, cyclopentyl, cyclohexyl, and the like. A heterocycloalkyl group is a cycloalkyl group as defined above where at least one of the carbon atoms of the ring is substituted with a heteroatom such as, but not limited to, nitrogen, oxygen, sulfur, or phosphorous.

CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG.

Enzyme-degradable labile bond: A covalent bond between two moieties that can undergo enzyme catalyzed hydrolysis. In several embodiments, the enzyme is an intracellular enzyme, such as a cathepsin.

Ester: A carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Expression vector: A recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids, and viruses (e.g., lentiviruses, retroviruses, adenoviruses, and adeno-associated viruses) that incorporate the recombinant polynucleotide.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Functional group: A specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

Halogenated alkyl or Haloalkyl group: An alkyl group with one or more hydrogen atoms present on these groups substituted with a halogen (F, Cl, Br, I).

Hydroxyl: A group represented by the formula —OH.

Hydroxyalkyl: An alkyl group that has at least one hydrogen atom substituted with a hydroxyl group. A alkoxyalkyl group is an alkyl group that has at least one hydrogen atom substituted with an alkoxy group described above.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogenic composition: A composition comprising a nucleic acid molecule or expression vector encoding an antigen that induces a measurable CTL response against the antigen, or induces a measurable B cell response (such as production of antibodies) against the antigen. The antigen can be expressed in a subject following administration of an effective amount of the immunogenic composition to the subject, and thus be used to elicit an immune response against the antigen).

In one example, an "immunogenic composition" is a composition that includes polymer nanoparticles of an expression vector delivery system complexed with an expression vector encoding an antigen as described herein, that can induce a measurable CTL response against the antigen when administered to a subject, or can induce a measurable B cell response (such as production of antibodies) against the antigen when administered to a subject.

For in vivo use, the immunogenic composition will typically include polymer nanoparticles of an expression vector delivery system complexed with an expression vector encoding an antigen in a pharmaceutically acceptable carrier and may also include other agents. Any particular polymer nanoparticles of an expression vector delivery system complexed with an expression vector encoding an antigen can be readily tested for its ability to induce a CTL or B cell response by art-recognized assays.

Infectious agent: An agent that can infect a subject, including, but not limited to, viruses, bacteria, and fungi.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). As used herein, "linked" and variations thereof refer to components that maintain a chemical or physical association after immunization at least until they contact a cell, such as an immune cell.

In several embodiments, linked components are associated in a chemical or physical manner so that the components are not freely dispersible from one another, at least until contacting a cell, such as an immune cell. For example, two components may be covalently bound to one another so that the two components are incapable of separately dispersing or diffusing Linking is specifically distinguished from a simple mixture of antigen and adjuvant such as may be found, for example, in a conventional vaccine. In a simple mixture, the components can be free to independently disperse within the vaccinated environment.

Nucleic acid: A polymer composed of at least 10 nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleic acid molecule encoding an antigen" includes all nucleotide sequences that are degenerate versions of each other and that encode the same antigen. Nucleotide sequences that encode proteins and RNA may include introns.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pattern recognition receptor: A protein receptor expressed by cells of the immune system to identify pathogen-associated molecular patters (PAMPS) as well as damage associated molecular patterns (DAMPs). PAMP or DAMP activation of pattern recognition receptors induces an intracellular signaling cascade resulting in the alteration of the host cell's transcription profile to induce expression of a host of pro-inflammatory and pro-survival genes that enhance adaptive immunity. Non-limiting examples of pattern recognition receptors include Toll-like receptors (TLR), Stimulator of Interferon Genes receptor (STING), C-type lectin receptors (CLR), RIG-I-like receptors (RLR), and NOD-like receptors (NLR). Agonists of such pattern recognition receptors can be used as adjuvants for enhancing an immune response to a target antigen.

Toll-like receptors (TLRs) 1-13 are transmembrane PRRs that recognize a diverse range of PAMPs. TLRs can be divided into two broad categories—those that are localized to the cell surface and those that are localized to the endosomal lumen. TLRs that are present on the cell surface are important in recognition of bacterial pathogens. TLRs that are localized to the lumen of endosomes, such as TLRs 3, 7, 8, and 9, serve to recognize nucleic acids and are thus thought to be important in the promotion of antiviral immune responses. TLR-7 and TLR-8 recognize ssRNA. Several different imidazoquinoline compounds are known TLR-7/8 agonists. TLR-9 recognizes unmethylated deoxycytidylate-phosphate-deoxyguanylate (CpG) DNA, found primarily in bacteria.

The NOD-like receptors (NLRs) and the RIG-I-like receptors (RLRs) are localized to the cytoplasm. Non-limiting examples of RLRs include RIG-I, MDAS, and LGP2. There are 22 human NLRs that can be subdivided into the five structurally related NLR families A, B, C, P, and X. All NLRs have three domains: an N-terminal domain involved in signaling, a nucleotide-binding NOD domain, and a C-terminal leucine rich region (LRR) important for ligand recognition. Non-limiting examples of NLRs include NALP3 and NOD2.

For more information on pattern recognition receptors, see, for example, Wales et al., Biochem Soc Trans., 35:1501-1503, 2007.

Pharmaceutical composition: A composition including an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, PA (19th Edition).

Pharmaceutically acceptable carrier: The pharmaceutically acceptable carriers (vehicles) useful in this disclosure are conventional. Remington: The Science and Practice of Pharmacy, The University of the Sciences in Philadelphia, Editor, Lippincott, Williams, & Wilkins, Philadelphia, PA, 21st Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired tumor response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Pharmaceutically acceptable salt or ester: Salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like.

Pharmaceutically acceptable salts of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of pharmacologically acceptable salts, see Berge et al., *J. Pharm. Sci.* 66:1 (1977).

Pharmaceutically acceptable esters include those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Polymer: A molecule of repeating structural units (monomers) formed via a chemical reaction, i.e., polymerization. The polymers included in the disclosed embodiments can form polymer nanoparticles that can be administered to a subject without causing toxic side effects. Further, the polymers included in the disclosed embodiments include a side chain with a functional group that can utilized, for example, to facilitate linkage to an adjuvant prodrug. In several embodiments, the polymer can be a cationic polymer (that is, a polymer with a predominantly positive charge) that can form a complex with a nucleic acid-based expression vector by electrostatic interaction. Non-limiting examples of cationic polymers that can be used in the disclosed embodiments include poly(lysine), polyphosphoesters, poly(amidoamines)s, poly(ethylenimine) (PEI), and Poly(beta-amino ester)s (PBAEs) based polymers.

Polymer Nanoparticle: A nanoparticle structure that can form spontaneously from polymers in aqueous solution. The polymer nanoparticles used in the disclosed embodiments have an average diameter of from 50 to 1000 nm and can be taken up into cells (e.g., immune cells). In some embodiments, the polymer nanoparticles may be included in larger particle structures, including those that are too large for uptake by immune cells (e.g., particles larger than about 5000 nm) and that slowly release the polymer nanoparticles including prodrug adjuvant as a function of their degradation. In several embodiments, the polymer nanoparticle includes a cationic polymer that can self-assemble with a negatively charged expression vector (e.g., a DNA or RNA plasmid expression vector) to form the polymer nanoparticles having a diameter of from 100 to 1000 nm.

The disclosed polymer nanoparticles are formed by a polymer linked to an adjuvant prodrug and an expression vector encoding an antigen. In several embodiments, such polymer nanoparticles can be administered to a subject without causing toxic side effects. Additionally, in several embodiments, the polymer nanoparticles can be substantially non-immunogenic, that is, the immunogenicity associated with the polymer nanoparticle primarily results from the immune response to the antigen encoded by an expression vector and the activated (non-prodrug) form of the adjuvant, as opposed to the nanoparticle, the polymer, the expression vector, and/or the adjuvant prodrug.

Polymerization: A chemical reaction, usually carried out with a catalyst, heat or light, in which a large number of relatively simple molecules (monomers) combine to form a chainlike macromolecule (a polymer). The chains further can be combined, or crosslinked, by the addition of appropriate chemicals. The monomers typically are unsaturated or otherwise reactive substances. Polymerization commonly occurs by addition or condensation. Addition polymerization occurs when an initiator, usually a free radical, reacts with a double bond in the monomer. The free radical adds to one side of the double bond, producing a free electron on the other side. This free electron then reacts with another monomer, and the chain becomes self-propagating. Condensation polymerization involves the reaction of two monomers, resulting in the splitting out of a water molecule.

Promoter: An array of nucleic acid control sequences which direct transcription of a nucleic acid. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters include, but are not limited to the SV40 promoter, the CMV enhancer-promoter, and the CMV enhancer/β-actin promoter. Both constitutive and inducible promoters are included (see e.g., Bitter et al., *Methods in Enzymology* 153:516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Subject: Includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

Substituted or Substitution: Replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Sulfinyl: The group —S(=O)H. A substituted sulfinyl or sulfoxide is a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

Sulfonyl: The group —$SO_2$H. The sulfonyl group can be further substituted with a variety of groups to form, for example, sulfonic acids, sulfonamides, sulfonate esters and sulfones. A substituted sulfonyl is a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

Sulfonylamido or sulfonamide: The group —$SO_2NH_2$.

Therapeutically effective amount: The amount of an agent that alone, or together with one or more additional agents, induces a desired response, such as, for example, an anti-tumor immune response, or an anti-viral immune response, in a subject. Ideally, a therapeutically effective amount provides a therapeutic effect without causing a substantial cytotoxic effect in the subject.

In one example, a desired response is to induce an immune response that inhibits or reduces or prevents infection by an infectious agent, such as a virus. The infected cells do not need to be completely eliminated or reduced or prevented for the composition to be effective. For example, administration of a therapeutically effective amount of the immunogenic composition can decrease the number of infected cells (or prevent the infection of cells) in a subject by a desired amount, for example by at least 10%, at least 20%, at least 50%, at least 60%, at least 70%, at least 80%, at least 90%, at least 95%, at least 98%, or even at least 100% (elimination or prevention of detectable infected cells), as compared to the number of infected cells in the absence of the composition.

In one example, a desired response is to induce an immune response that leads to a reduction in the size, volume, or number (such as metastases) of a tumor in a subject. For example, the agent or agents can induce an immune response that decreases the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of a disclosed immunogenic composition including nanoparticles of an expression vector delivery system complexed with an expression vector encoding an antigen that is administered to a human or veterinary subject will vary depending upon a number of factors associated with that subject, for example the overall health of the subject. A therapeutically effective amount can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired immune response. However, the therapeutically effective amount of can be dependent on the source applied, the subject being treated, the severity and type of the condition being treated, and the manner of administration.

The therapeutically effective amount of a disclosed immunogenic composition including polymer nanoparticles of an expression vector delivery system complexed with an expression vector encoding an antigen can be administered systemically or locally. In addition, the therapeutically effective amount can be administered in a single dose, or in several doses, for example daily, during a course of treatment. However, the therapeutically effective amount will be dependent on the preparation applied, the subject being treated, the severity and type of the affliction, and the manner of administration of the compound Thiol: The group —SH. A substituted thiol is a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

Treating or Inhibiting a Disease: A therapeutic intervention that reduces a sign or symptom of a disease or pathological condition related to a disease (such as a tumor or viral infection). Treatment can also induce remission or cure of a condition, such as a tumor or viral infection. In particular examples, treatment includes preventing a tumor, for example by inhibiting the full development of a tumor, such as preventing development of a metastasis or the development of a primary tumor. Prevention does not require a total absence of a tumor.

Reducing a sign or symptom of a disease or pathological condition related to a disease, refers to any observable beneficial effect of the treatment. Reducing a sign or symptom associated with a tumor or viral infection can be evidenced, for example, by a delayed onset of clinical symptoms of the disease in a susceptible subject (such as a subject having a tumor which has not yet metastasized, or a subject that may be exposed to a viral infection), a reduction in severity of some or all clinical symptoms of the disease, a slower progression of the disease (for example by prolonging the life of a subject having a tumor or viral infection), a reduction in the number of relapses of the disease, an improvement in the overall health or well-being of the subject, or by other parameters well known in the art (e.g., that are specific to a particular tumor or viral infection). A "prophylactic" treatment is a treatment administered to a subject who does not exhibit signs of a disease or exhibits only early signs for the purpose of decreasing the risk of developing pathology.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

An "established" or "existing" tumor is an existing tumor that can be discerned by diagnostic tests. In some embodiments, and established tumor can be palpated. In some embodiments, and "established tumor" is at least 500 mm$^3$, such as at least 600 mm$^3$, at least 700 mm$^3$, or at least 800 mm$^3$ in size. In other embodiments, the tumor is at least 1 cm long. With regard to a solid tumor, and established tumor generally has an robust blood supply, and has induced Tregs and myeloid derived suppressor cells (MDSC).

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

II. Expression Vector Delivery System Including an Adjuvant Prodrug

Disclosed herein are embodiments of a novel system for delivering an expression vector encoding an antigen to a subject that allows for spatiotemporal control over activation of the subject's immune response to the antigen. The expression vector delivery system includes a polymer linked to an adjuvant prodrug, for example, via a linker. In several embodiments, the polymer can interact with the expression vector (e.g., by electrostatic interaction) and form polymer nanoparticles under physiological conditions that can be taken up into a cell (such as an immune cell, for example, an antigen presenting cell). In additional embodiments, the polymer linked to the prodrug can form polymer nanoparticles under physiological conditions that can be taken up into a cell (such as an immune cell, for example, an antigen presenting cell) and the expression vector can be admixed with the polymer nanoparticles. A detailed discussion of the components of the expression vector delivery system follows.

Polymer Nanoparticles

In several embodiments, the expression vector delivery system includes a polymer with which the expression vector can bind (e.g., by electrostatic interaction) and form polymer nanoparticles under physiological conditions that can be taken up into a cell (such as an immune cell, for example, an antigen presenting cell). In additional embodiments, the polymer linked to the prodrug can form polymer nanoparticles under physiological conditions that can be taken up into a cell (such as an immune cell, for example, an antigen presenting cell) and the expression vector can be admixed with the polymer nanoparticles. The polymer nanoparticles are of a size that can be taken up into the endosomal system of cells (such as immune cells). In a population of such polymer nanoparticles the polymer nanoparticles can be all of the same type (e.g., the same size, or including the same expression vector sequences) or the polymer nanoparticles can be made up of two or more different types (e.g., including varying sizes, or including different expression vector sequences) in any combination and in any ratio. The polymer nanoparticles formed by the expression vector complexed with the expression vector delivery system can be in an average size range of about 50 nm to about 1000 nm. Thus, the polymer nanoparticles can average about 50 nm, about 75 nm, about 100 nm, about 150 nm, about 200 nm, about 250 nm, about 300 nm, about 400 nm, about 500 nm, about 750 nm, about 1000 nm, or can have an average range of about 50 nm to about 500 nm, from about 100 nm to about 500 nm, from about 100 nm to about 750 nm, from about 100 nm to about 1000 nm, from about 250 nm to about 750 nm, from about 500 nm to about 1000 nm, from about 250 nm to about 500 nm. It will be appreciated by one of skill in the art that in an immunogenic composition comprising the polymer nanoparticles formed by the expression vector complexed with the expression vector delivery system, the polymer nanoparticles in the composition can vary in size, but will generally fall within the size range set forth herein. Methods of generating polymer nanoparticles from soluble polymer coils complexed with nucleic acid molecules are known (see, e.g., Shmueli et al., J. Visualized Exp., 73:e50176, 2013; and U.S. Pat. No. 8,323,696; Guerrero Cazarez et al., ACS Nano, 8: 5141-5153, 2014). In a

Polymer

The expression vector delivery system includes a polymer that can be linked to an adjuvant prodrug, can form a complex with an expression vector (e.g., by electrostatic interaction), and can form polymer nanoparticles that can be administered to a subject without causing toxic side effects. Any appropriate polymer can be used. The polymer can be a statistical copolymer or alternating copolymer. The polymer can be a block copolymer, such as the A-B type, or the polymer can be comprised of a grafted copolymer, whereby two polymers are linked through polymer analogous reaction.

The polymer may include naturally occurring and synthetic monomers and combinations thereof. Natural biopolymers may include single or double stranded RNA or DNA, comprised of nucleotides (e.g., adenosine, thymidine). The natural biopolymers can be peptides comprised of amino acids; a specific example is poly(lysine). Biopolymers can be polysaccharides, which may include but are not limited to glycogen, cellulose and dextran. Additional examples include polysaccharides that occur in nature, including alginate and chitosan. Polymers may also be comprised of naturally occurring small molecules, such as lactic acid or glycolic acid, or may be a copolymer of the two (i.e., PLGA). Suitable preformed particles may also be based on formulations (e.g., stabilized emulsions, liposomes and polymersomes) or may be mineral salts that form particles suitable for complexation or ion exchange on the surfaces of the particles, which may include Aluminum-based salts.

In some embodiments, the polymer can be an anionic (e.g., poly(acidic)) polymer or cationic (e.g., poly(basic)) polymer. Cationic polymers can bind to nucleic acid-based expression vectors (such as DNA or RNA plasmid vectors) by electrostatic interaction. In some embodiments, the cationic polymer can be a naturally occurring or synthetic poly(amine), such as poly(lysine) or poly(ethylenimine) (PEI). In additional embodiments, the cationic polymer can be a poly(amido amine) (PAA) or poly(beta amino ester) (PBAE) produced from the Michael addition reaction of amines with either bis(acrylamides) or bis(acrylesters). Non-limiting examples of cationic polymers that can be used in the disclosed embodiments include poly(ethylenimine), poly(allylanion hydrochloride; PAH), putrescine, cadaverine, poly(lysine) (PL), poly(arginine), poly(trimethylenimine), poly(tetramethylenimine), poly(propylenimine), aminoglycoside-polyamine, dideoxy-diamino-b-cyclodextrin, spermine, spermidine, cadaverine, poly(2-dimethylamino)ethyl methacrylate, poly(histidine), cationized gelatin, dendrimers, chitosan, and any combination thereof. The cationic polymer may contain a quaternary ammonium group, such as that present on methylated chitosan. The prodrug adjuvant can be linked to the polymer through one of the various aforementioned linker groups. The polycation polymer (e.g., PEI or PL) can be complexed with the expression vector via physical electrostatic force (e.g., wherein the negative charges in the nucleic acid of the expression vector bind with the positive charges in the poly(cation)).

In additional embodiments, the polymer may include monomers of (meth)acrylates, (meth)acrylamides, styryl and vinyl moieties. Specific examples of (meth)acrylates, (meth)acrylamides, as well as styryl- and vinyl-based monomers include N-2-hydroxypropyl(methacrylamide) (HPMA), hydroxyethyl(methacrylate) (HEMA), Styrene and vinylpyrrolidone (PVP), respectively. The polymer can be a thermoresponsive polymer comprised of monomers of N-isopropylacrylamide (NIPAAm); N-isopropylmethacrylamide (NIPMAm); N,N'-diethylacrylamide (DEAAm); N-(L)-(1-hydroxymethyl)propyl methacrylamide (HMP-MAm); N,N'-dimethylethylmethacrylate (DMEMA), 2-(2-methoxyethoxy)ethyl methacrylate (DEGMA). Polymers can also be based on cyclic monomers that include cyclic urethanes, cyclic ethers, cyclic amides, cyclic esters, cyclic anhydrides, cyclic sulfides and cyclic amines.

In some embodiments, the polymer can be a hydrophilic polymer with near neutral charge, such as a poly(N-(2-hydroxypropyl(methacrylamide)) (pHPMA)-based co-polymer, wherein the polymer is linked to an adjuvant prodrug (such as a prodrug TLR-7/8 agonist) through a linker group. The hydrophilic polymer-prodrug adjuvant can be comprised of unimolecular polymer coils or can be induced to form particles. In several embodiments, the hydrophilic polymer-prodrug adjuvant that does not carry high positive charge density and can be admixed with an expression vector, such as a DNA expression vector that does not contain any CpG motifs.

Polymers based on cyclic monomers may be produced by ring opening polymerization and include polyesters, polyethers, polyamines, polycarbonates, polyamides, polyurethanes and polyphosphates; specific examples may include but are not limited to polycaprolactone and poly (ethylenimine) (PEI). Suitable polymers may also be produced through condensation reactions and include polyamides, polyacetals and polyesters.

The polymer included in the expression vector delivery system includes a plurality of monomer units. In some embodiments, the polymer can include from 3 to 10000 monomer units, such as from 3 to 500 monomer units, from 3 to 100 monomer units, from 3 to 50 monomer units, from 3 to 10 monomer units, from 5 to 1000 monomer units, such as from 5 to 500 monomer units, from 5 to 100 monomer units, from 5 to 50 monomer units, from 5 to 10 monomer units, from 500 to 1000 monomer units, from 100 to 500 monomer units, from 250 to 500 monomer units, from 300 to 600 monomer units, or from 100 to 250 monomer units. Typically at least five monomers are needed to sufficiently complex the negatively charged nucleic acid. In embodiments including a cationic polymer, increasing the number of monomer units (degree of polymerization) increases the strength of the interaction of the positively charged polymer and negatively charged nucleic acid. In some embodiments, the average molecular weight of the polymer may be between about 5,000 to 1,000,000 g/mol. The polydispersity indexes of the polymer may range from about 1.05 to about 5.0.

The monomers of the polymer included in the expression vector delivery system include a sidechain including at least one functional group that can be coupled to the adjuvant prodrug, or to a linker that can be coupled to the adjuvant prodrug. However, typically not all of the monomers in the polymer are linked to the adjuvant prodrug. For example, the ratio of adjuvant prodrug to monomer of the polymer can be from 1:100 to 1:1 mol/mol, such as from 1:20 to 1:10 mol/mol. Typically, the delivery system includes a sufficiently high density of the adjuvant prodrug to enhance an immune response without impacting the ability of the polymer to complex with nucleic acid molecules and form polymer nanoparticles under physiological conditions.

Linker

The adjuvant prodrug can be linked to the polymer by any suitable means. Both covalent and non-covalent attachment means may be used. The procedure for linking the adjuvant prodrug to the polymer varies according to the chemical structure of the adjuvant and the polymer. In some instances, the polymer can be directly linked to the adjuvant prodrug. In other instance, the polymer can be indirectly linked to the adjuvant prodrug via a linker. Suitable linkers are well known to those of skill in the art and include, but are not limited to, straight or branched-chain carbon linkers, heterocyclic carbon linkers, peptide linkers, or a combination thereof. In some embodiments, the carbon linker can include a $C_1$-$C_{18}$ alkane linker. The linker molecule may comprise a hydrophilic or hydrophobic linker. Typically, the linker is capable of forming covalent bonds to both the polymer and the adjuvant. In several embodiments, the linker includes a peptide that is cleavable by an intracellular enzyme (such as a cathepsin).

In some embodiments, the linker may comprise one or more PEG moieties. The linker, such as PEG, may be at least 2 monomers in length. The linker, such as PEG, may be between about 4 and about 24 monomers in length, or more. In some embodiments, where the linker comprises a carbon chain, the linker may comprise a chain of between about 1 or 2 and about 18 carbons. In some embodiments, where the linker comprises a carbon chain, the linker may comprise a chain of between about 12 and about 20 carbons. In some embodiments, where the linker comprises a carbon chain, the linker may comprise a chain of between no more than 18 carbons.

The linker may be linked to the polymer by any suitable chemical moiety, for example any moiety resulting from a 'click chemistry' reaction, or thiol exchange chemistry. For example, a triazole group may attach the linker to the polymer. An alkyne group and an azide group may be provided on respective molecules to be linked by "click chemistry". For example the prodrug PRR agonist may comprise, or be modified with, an N-terminal azide that allows for coupling to a polymer having an appropriate reactive group such as an alkyne group. The skilled person will understand that there are a number of suitable reactions available to link the linking group to the polymer backbone. In one embodiment, the linker may be linked to the polymer backbone of the polymer by an amine. The link with an amine may be provided by reacting any suitable electrophilic group such as alkenes (via Michael addition), activated esters (for example, NHS ester), aldehydes, and ketones (via Schiff base). The prodrug adjuvant may be linked to the polymer using split intein or SpyTag or other enzymatic ligase strategies. In several embodiments, linkage of an adjuvant to the linker generates the prodrug form of the adjuvant; active adjuvant is released when the linkage to the linker is degraded (e.g., by enzyme catalyzed degredation such as cathepsin cleavage).

In additional embodiments, the adjuvant prodrug can be linked to the polymer through non-covalent high affinity interactions such as that by coil-coil interactions from two complementary 28 amino acid coil domains present on the adjuvant prodrug and polymer respectively. Additional interactions include avidin/biotin and antibody/epitope interactions that would be permissive to linking the prodrug PRR agonist with a polymer backbone.

In some embodiments, the linker may be a poly(basic) or poly(acidic) molecule that carriers a positive or negative charge, respectively. The poly(basic) linker that can be electrostatically complexed to a poly(acidic) polymer through charge neutralization. The poly(acidic) linker can be electrostatically complexed to a poly(basic) polymer. The positive charge can be non-basic in origin and may result from a quaternary amine.

In some embodiments, the linker is cleavable under intracellular conditions, such that cleavage of the linker releases the adjuvant from the polymer in the intracellular environment.

For example, the linker can be cleavable by an enzyme that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease (such as a cathepsin). In some embodiments, the peptide linker is at least two amino acids long or at least three amino acids long. However, the linker can be 2, 3, 4, 5, 6, 7, 8, 9, 10, 11, 12, 13, 14 or 15, or more (such as up to 30) amino acids long, such as 2-5, 3-10, 3-15, 2-5, 2-10, 2-15, or more amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

Particular sequences for the cleavable peptide in the linker can be used to control the rate of cleavage of the linker. For tetrapeptide linkers (including four amino acids), for rapid cleavage, preferred amino acids at the P1 position of the tetrapeptide are K, R, Q, T, L, N, or M. For slow release, preferred amino acids at the P1 position of the tetrapeptide are H, D, E, G, P, F, A, V or I. In some embodiments, use of D amino acids in the linker provides another means of slowing the rate of hydrolysis. In some embodiments, the linker can include a cathepsin-cleavable peptide comprising L-amino acids or D-amino acids comprising the amino acid sequence set forth as one of: GFLG (SEQ ID NO: 1), KPLR (SEQ ID NO: 2), KLRP (SEQ ID NO: 3), SLVR (SEQ ID NO: 4), or SLRV (SEQ ID NO: 5).

In other embodiments, the cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2- pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In some embodiments, the linker can include a spacer element, which, when present, increases the size of the linker such that the distance between the polymer and the adjuvant is increased. Exemplary spacers are known to the person of ordinary skill, and include those listed in U.S. Pat. Nos. 7,964,567, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Adjuvant Prodrug

The adjuvant prodrug linked to the polymer may be, or be derived from, any suitable adjuvant. Suitable adjuvants include small organic molecules, i.e., molecules having a molecular weight of less than about 1000 Daltons, although in some embodiments the adjuvant may have a molecular weight of less than about 700 Daltons and in some cases the adjuvant may have a molecular weight from about 500 Daltons to about 700 Daltons.

The density of the adjuvant prodrug included in the expression vector delivery system can be varied as needed for particular applications. For example, the adjuvant prodrug may be linked to the monomer units (such as co-monomer units) of the polymer at a density of from 1 to 100 mol %, such as from 1 to 10 mol %, from 5 to 10 mol %, from 1 to 5 mol % of the polymer, from 5 to 15 mol %, from 10 to 20 mol %, from 10 to 15 mol %, from 7 to 13 mol %, from 8 to 10 mol %, from 1 to 25 mol %, from 5 to 25 mol %, from 10 to 25 mol %. The mol % of the prodrug adjuvant refers to the molar percentage of monomer units bearing the prodrug adjuvant incorporated to the main polymer chain. For example, 10 mol % prodrug adjuvant is equal to 10 monomer units linked to the prodrug adjuvant molecules from a total 100 monomer units. The remaining 90 may be macromolecule-forming monomeric units.

In some embodiments, the adjuvant prodrug may be linked to the monomer units (such as co-monomer units) of the polymer at a density of from 1 to 3 mol %, from 2 to 4 mol %, from 3 to 5 mol %, from 4 to 6 mol %, from 5 to 7 mol %, from 6 to 8 mol %, from 7 to 9 mol %, from 8 to 10 mol %, from 9 to 11 mol %, from 10 to 12 mol %, from 11 to 13 mol %, from 12 to 14 mol %, from 13 to 15 mol %, from 14 to 16 mol %, from 15 to 17 mol %, from 16 to 18 mol %, from 17 to 19 mol %, from 18 to 20 mol %, from 20 to 22 mol %, from 21 to 23 mol %, from 22 to 24 mol % from 23 to 25 mol %.

In some embodiments, the adjuvant prodrug may be linked to the monomer units (such as co-monomer units) of the polymer at a density of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, about 21 mol %, about 22 mol %, about 23 mol %, about 24 mol %, about 25 mol %.

The adjuvant includes a functional moiety required for adjuvant activity that is masked by linkage to a progroup, to the polymer, or to a linker connected to the polymer, to form the adjuvant prodrug with ablated adjuvant activity. In some embodiments, the functional moiety can be joined to the progroup, the polymer, or the linker connected to the polymer, by an enzyme-degradable labile bond. Cleavage of the enzyme degradable bond activates the adjuvant. The rate of cleavage of the enzyme-degradable labile bond is slow enough to delay adjuvant-induced immune activation until after the antigen encoded by the expression vector is expressed by the cell. Thus, use of the adjuvant prodrug delays the onset of immune activation to avoid adjuvant-induced immune responses that decrease expression of the antigen from the expression vector. Typically, antigen expression from the expression vector begins about 2 days following administration of polymer nanoparticles including the expression vector delivery system complexed with the expression vector. Accordingly, in several embodiments, the adjuvant-induced immune response can peak or cross a minimal threshold (i.e., >2×S.D. of the magnitude of the innate immune responses induced by the expression vector without adjuvant, where S.D. is standard deviation) of innate immune stimulation needed to elicit an appreciable T cell response against the encoded antigen from 4-10 days (such as 4 days, 5 days, 6 days, 8 days) following administration of the polymer nanoparticles including the expression vector delivery system complexed with the expression vector.

Several methods are available for determining the timing of immune activation in vivo and involve the use of either a host carrying a reporter enzyme (for example, luciferase) or involve analysis of a tissue biopsy. A suitable host carrying a reporter enzyme that would indicate the timing of immune activation is a murine host that produces luciferase upon nuclear translocation of the transcription factor NF-kB. NF-kB is translocated to the nucleus of cells in the host upon immune activation and is considered among the first steps upon the initiation of an immune response. Measuring Luciferase expression by bioluminescence allows for an indirect measure of the timing of immune activation directly in the intact host. A direct measure of immune activation in the host requires tissue specimens to be collected. The cells from the tissue specimens can be analyzed for expression of genes associated with inflammation (for example, NF-kB) or the cells can be analyzed for the production of biomarkers, such as the expression of co-stimulatory molecules or the production of cytokines. In some examples, the timing of adjuvant-induced immune responses can be determined by quantifying the magnitude of lymph node cytokine production in the draining lymph nodes proximal to the site of administration of the polymer nanoparticles comprised of an expression vector delivery system linked to an adjuvant (active or in prodrug form) that is linked or simply admixed with an expression vector. Cytokine production in this assay is considered to be therapeutically relevant (i.e., capable of inducing CD8 T cell responses) when IL-12p40 cytokine production in the lymph node exceeds 2× the standard deviation of the magnitude of cytokine production induced by the expression vector delivery system that is not linked to adjuvant. This magnitude of cytokine production can be observed for the gene delivery system linked to the active adjuvant by 6 hours after administration but is not observed in the host that has received the polymer nanoparticles linked with the adjuvant prodrug until between 2-8 days after administration.

In several embodiments, the adjuvant prodrug can be a prodrug of a pattern recognition receptor agonist. Non-limiting examples of pattern recognition receptor agonists TLR-1/2/6 agonists (e.g., lipopeptides and glycolipids, such as Pam2cys or Pam3cys lipopeptides); TLR-3 agonists (e.g., dsRNA, such as PolyI:C, and nucleotide base analogs); TLR-4 agonist (e.g., lipopolysaccharide (LPS) derivatives and small molecule analogs of pyrimidoindole); TLR5 agonists (e.g., Flagellin); TLR-7/8 agonists (e.g., ssRNA and nucleotide base analogs, including derivatives of imidazoquinolines, hydroxy-adenine, benzonapthyridine and loxoribine); and TLR-9 agonists (e.g., unmethylated CpG); Stimulator of Interferon Genes (STING) agonists (e.g., cyclic dinucleotides, such as cyclic diadenylate monophosphate); C-type lectin receptor (CLR) agonists (such as various mono, di, tri and polymeric sugars that can be linear or branched, e.g., mannose, Lewis-X tri-saccharides, etc.); RIG-I-like receptor (RLR) agonists; and NOD-like receptor (NLR) agonists (such as peptidogylcans and structural motifs from bacteria, e.g., meso-diaminopimelic acid and muramyl dipeptide); and combinations thereof. In several embodiments, the pattern recognition receptor agonist can be a TLR agonist, such as an imidazoquinoline-based TLR-7/8 agonist. For example, the prodrug adjuvant can be a prodrug of Imiquimod (R837) or Resiquimod (R848), which are approved by the FDA for human use.

Disclosed herein is the unexpected finding that certain compositions of prodrug Toll-like receptor-7/8 agonists (TLR-7/8a) using labile amide bonds can delay the onset of immune activation (i.e. detection of pharmacodynamics biomarkers, such as cytokines) up to 6-8 days after delivery of the prodrug molecule on a polymeric delivery system. The extent of this delay would not be anticipated based on in vitro kinetics studies of similar prodrug approaches and potentially significantly improves the utility of this approach as peak gene expression by plasmids occurs between 4 and 8 days after delivery, thus allowing for optimal gene expression to occur prior to the onset of immune activation.

Accordingly, in several embodiments, the adjuvant prodrug can be a prodrug of a TLR-7 agonist, a TLR-8 agonist and/or a TLR-7/8 agonist. Numerous such agonists are known, including many different imidazoquinoline compounds.

Imidazoquinolines are of use in the methods disclosed herein. Imidazoquinolines are synthetic immunomodulatory drugs that act by binding Toll-like receptors 7 and 8 (TLR-7/TLR-8) on antigen presenting cells (e.g., dendritic cells), structurally mimicking these receptors' natural ligand, viral single-stranded RNA. Imidazoquinolines are heterocyclic compounds comprising a fused quinoline-imidazole skeleton. Derivatives, salts (including hydrates, solvates, and N-oxides), and prodrugs thereof also are contemplated by the present disclosure. Particular imidazoquinoline compounds are known in the art, see for example, U.S. Pat. Nos. 6,518,265; and 4,689,338. In some non-limiting embodiments, the imidazoquinoline compound is not imiquimod and/or is not resiquimod.

In some embodiments, the adjuvant prodrug can be a prodrug of a small molecule adjuvant having a 2-aminopyridine fused to a five membered nitrogen-containing heterocyclic ring, include but are not limited to imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In some embodiments, the adjuvant prodrug can be a prodrug of a TLR-7/8 agonist. For example the TLR-7/8 agonist prodrug can include a functional moiety required for TLR-7/8 agonist activity that is masked by a progroup, or is masked by linkage to the polymer or a linker (such as a cathepsin-cleavable linker) coupled to the polymer. In some embodiments, the TLR-7/8 agonist can be linked to the polymer (or a linker that is linked to the polymer) by a labile bond, the cleavage of which releases the TLR-7/8 agonist from the polymer and activates the TLR-7/8 agonist activity.

In some embodiments, the adjuvant prodrug can be a prodrug of a TLR-7/8 agonist and can include a formula:

(Formula I)

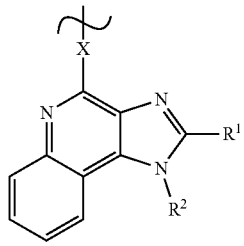

In Formula I, X is amine or hydrazine; $R^1$ is selected from one of hydrogen, optionally-substituted lower alkyl, or optionally-substituted lower ether; and $R^2$ is selected from one of hydrogen, optionally-substituted lower alkyl, optionally substituted aralkyl, optionally substituted benzyl, optionally substituted arylamine, or optionally substituted lower alkylamine. The polymer or linker can be joined to X by the labile bond; or the polymer or linker can be joined to one of $R^1$ or $R^2$, and X is joined to a progroup by the labile bond. In several embodiments the R2 position can include poly(basic) substituents, which can increase retention of the adjuvant in the endosomal system of a cell following release of the adjuvant from the polymer by the intracellular enzyme.

In some embodiments, the $R^1$ included in Formula I can be selected from hydrogen,

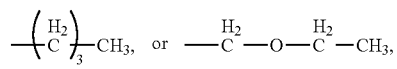

and/or the $R^2$ in Formula I can be selected from hydrogen,

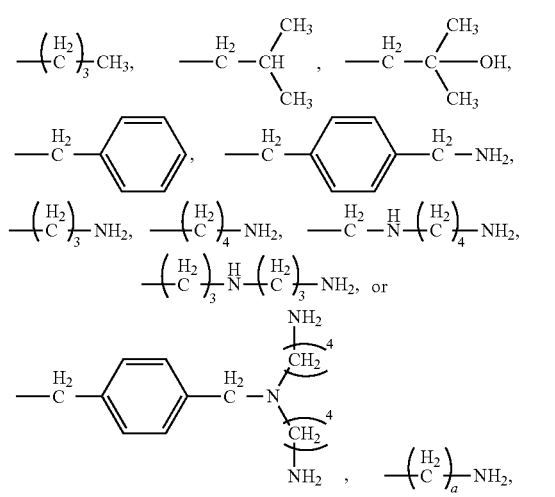

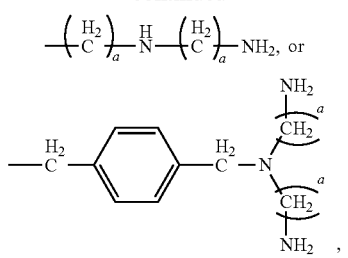

wherein a is independently 1 to 4. In some embodiments, $R^2$ can be

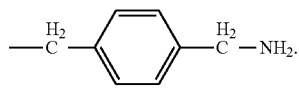

In some embodiments, $R^2$ can be

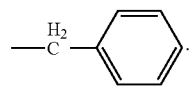

In some embodiments, the $R^1$ included in Formula I can be selected from hydrogen,

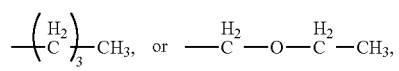

and/or $R^2$ can be selected from one of

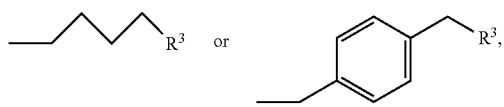

wherein $R^3$ can be selected from one of

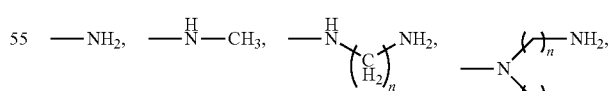

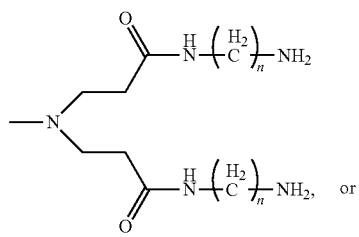

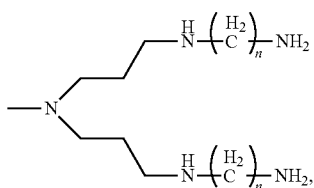

and wherein n is from 1 to 12, such as 1 to 4, for example 1 or 2.

Another unexpected finding disclosed herein is that the magnitude and duration of the activity induced by prodrug TLR-7/8a can depend on the poly(basic) character of the released TLR-7/8a. For example, as disclosed in Example 2, comparing two compositions of prodrug TLR-7/8a, the dibasic TLR-7/8a provides higher magnitude and greater duration of immune activity as compared with the monobasic compound. One non-limiting explanation is that this finding may be due to increased retention of the dibasic TLR-7/8a in the endosomal compartment of immune cells following hydrolysis of the chemically labile prodrug site, or may result from the 2+ charge on the di-basic molecule preventing membrane permeability and therefore leading to increased retention of the molecule in the draining lymphatics. Accordingly, in some embodiments, the TLR-7/8a can comprise Formula I, wherein X is amine or hydrazine, and $R^1$ is selected from one of hydrogen, optionally-substituted lower alkyl, or optionally-substituted lower ether; and $R^2$ comprises an optionally substituted arylamine, or optionally substituted lower alkylamine.

In some embodiments, the TLR-7/8a comprises a formula set forth as one of:

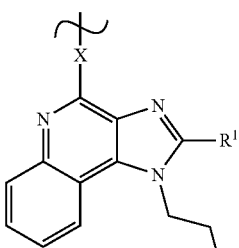

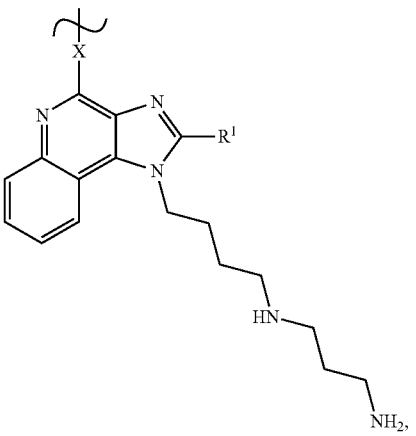

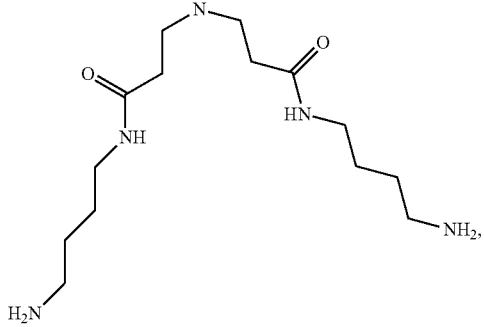

-continued
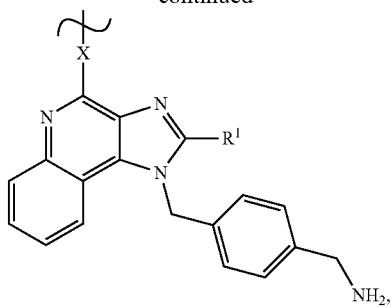
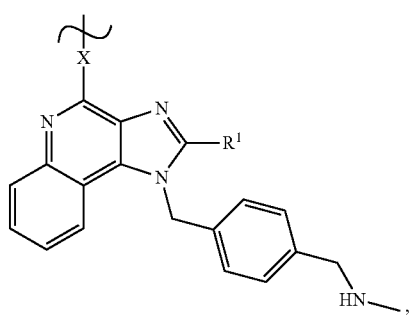
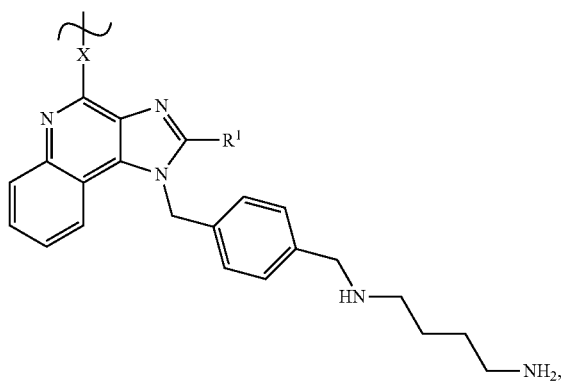
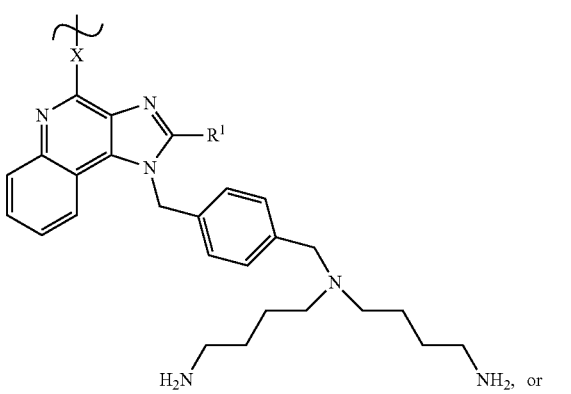
-continued
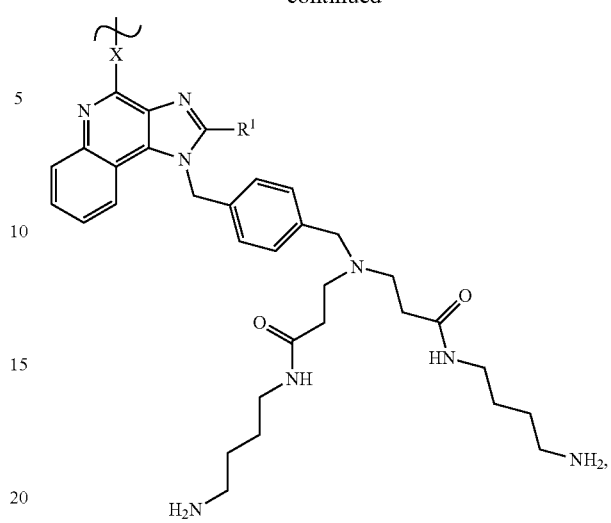
wherein $R^1$ is one of hydrogen,
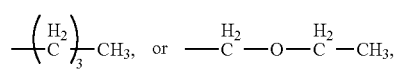
and X is amino or hydrazine, and the TLR-7/8a is linked to the polymer (or a linker linked to the polymer, such as a cathepsin cleavable linker) via the amino or hydrazine group. In several such embodiments, $R^1$ is
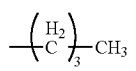
and $R^2$ is amino or hydrazine.
In some embodiments, the TLR-7/8a comprises a formula set forth as one of:
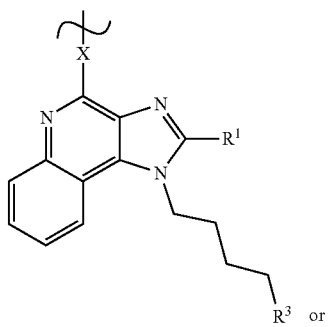

-continued

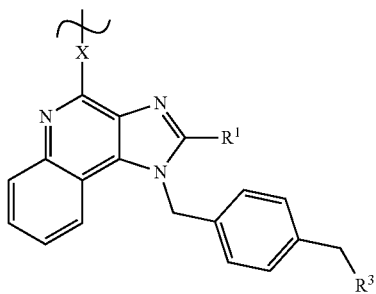

wherein, the $R^1$ can be selected from hydrogen,

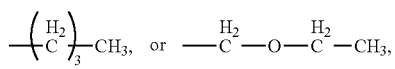

and/or $R^3$ can be selected from one of

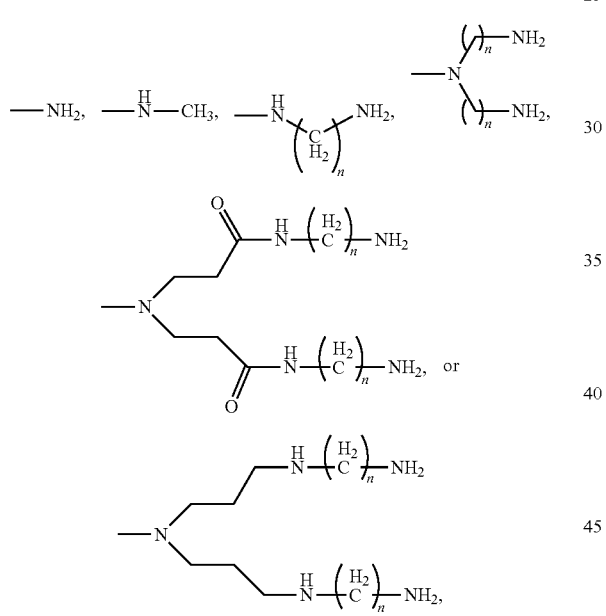

and wherein n is from 1 to 12, such as 1 to 4, for example 1 or 2, and X is amino or hydrazine, and the TLR-7/8a is linked to the polymer (or a linker linked to the polymer, such as a cathepsin cleavable linker) via the amino or hydrazine group. In several such embodiments, $R^1$ is

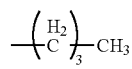

and $R^2$ is amino or hydrazine.

In some non-limiting embodiments, the prodrug TLR-7/8 agonist can comprise or consist of a poly(basic) structure, for example as set forth as one of the following formulas:

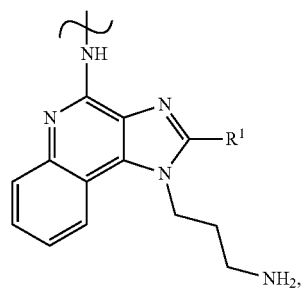

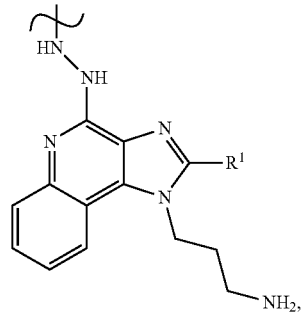

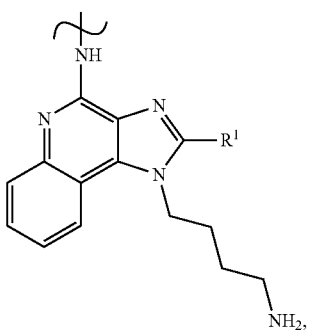

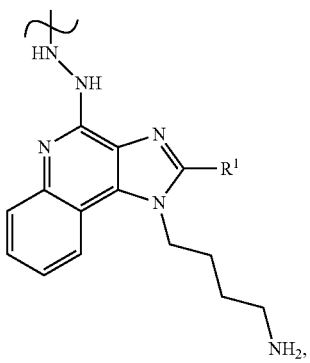

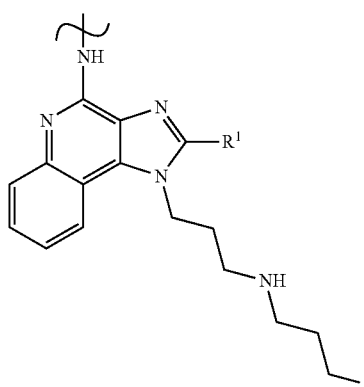

-continued
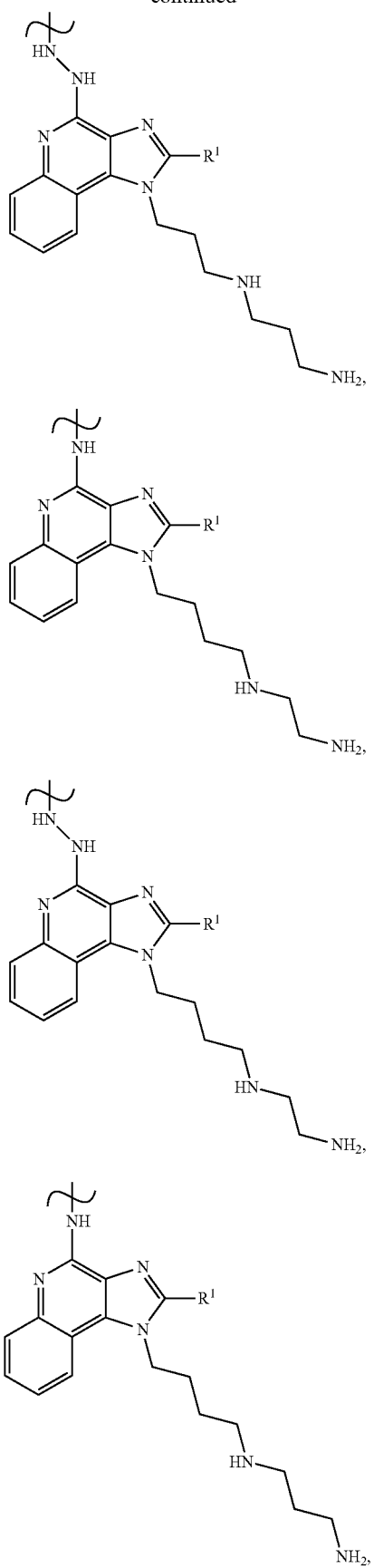
-continued
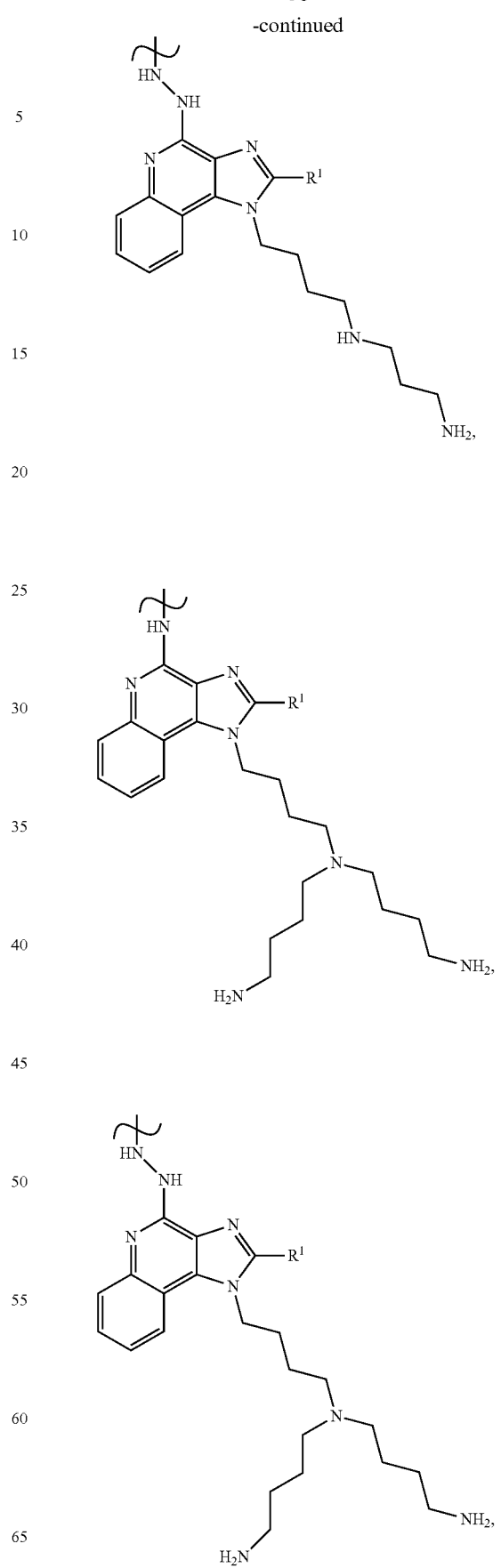

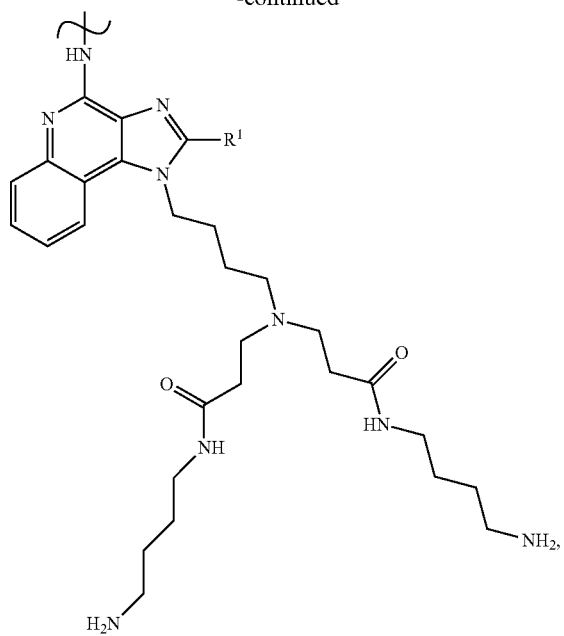
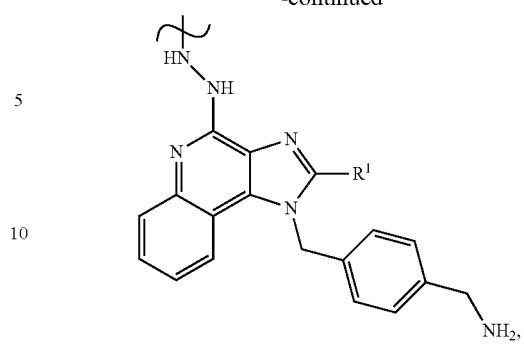

43
-continued
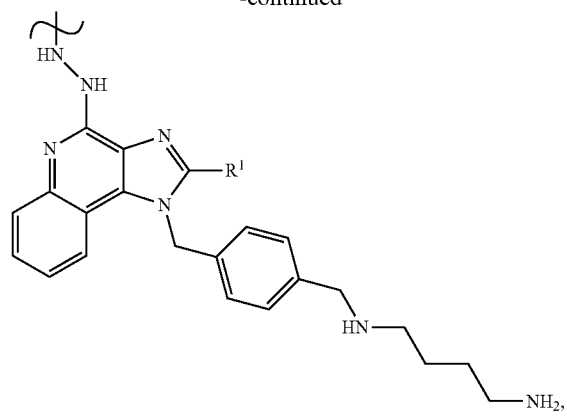
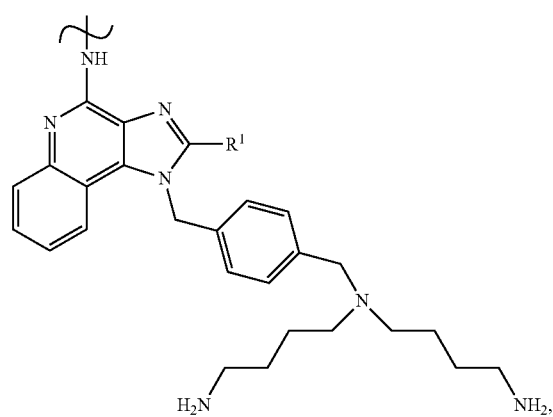
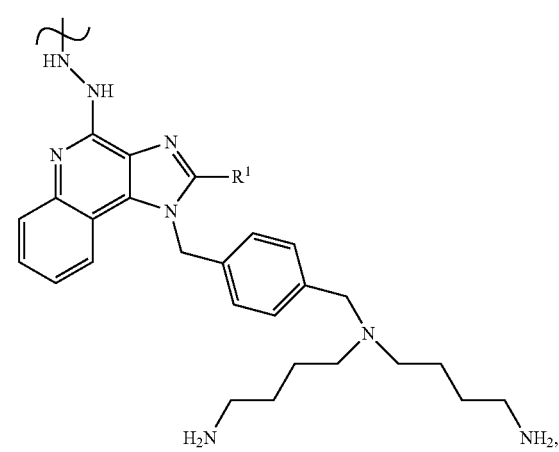
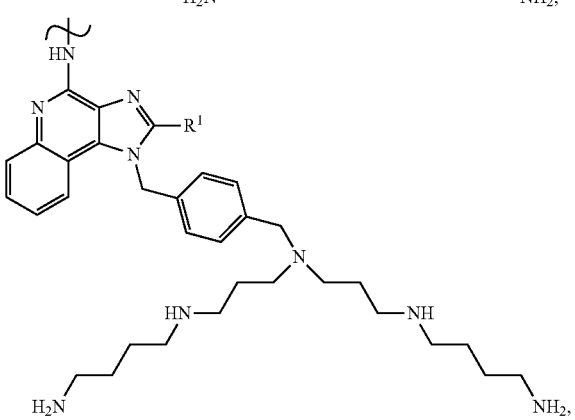
44
-continued
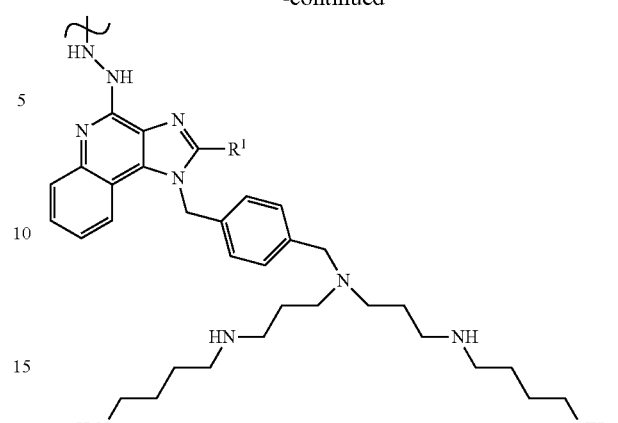
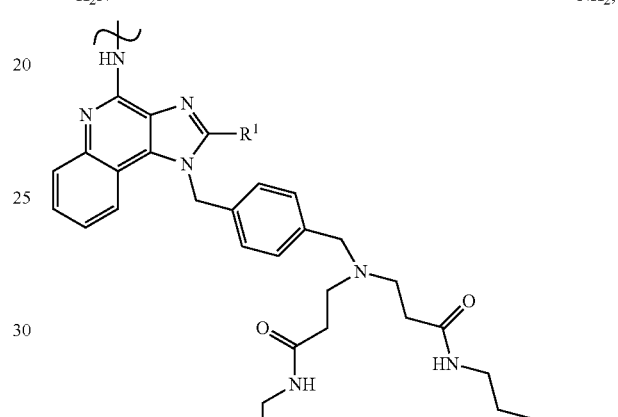
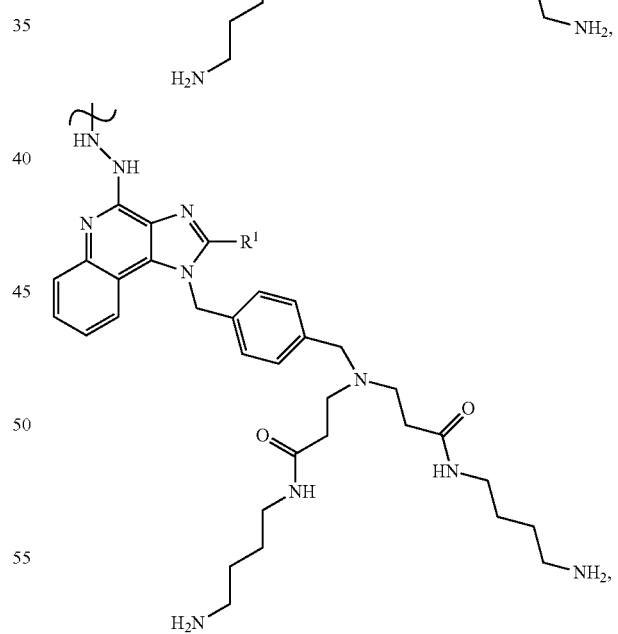
wherein $R^1$ is one of hydrogen,
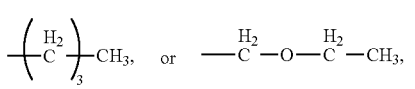

and the TLR-7/8a is linked to the polymer (or a linker linked to the polymer, such as a cathepsin cleavable linker) via the amino or hydrazine group. In several such embodiments, $R^1$ is

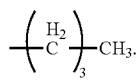

The polymer or linker can be linked to the amine or hydrazine by a labile bond, the cleavage of which releases the adjuvant from the polymer and activates the TLR-7/8 agonist activity of the agonist.

In additional embodiments, the adjuvant is a STING agonist, such as a cyclic-dinucleotide (CDN) STING agonist. In some embodiments, the STING agonist can comprise a formula:

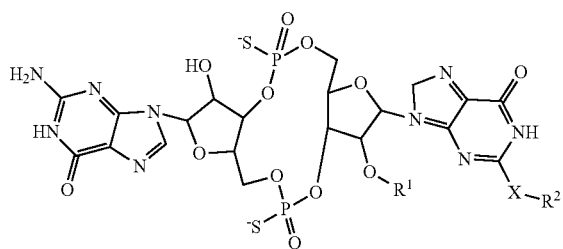

wherein, X is hydrazide or amine, and one of
(a) $R^1$ is hydrogen, and $R^2$ is the polymer or linker and is joined to X by the labile bond;
(b) $R^1$ is the polymer or linker and is joined to the ribose by the labile bond, and $R^2$ is hydrogen;
(c) $R^1$ is the polymer or linker and is joined to the ribose, and $R^2$ is a progroup joined to X by the labile bond; or
(d) $R^1$ is a progroup joined to the ribose by the labile bond, and $R^2$ is the polymer or linker.

In additional embodiments, the adjuvant can be a TLR-1/2 agonist. For example the adjuvant can comprises a formula:

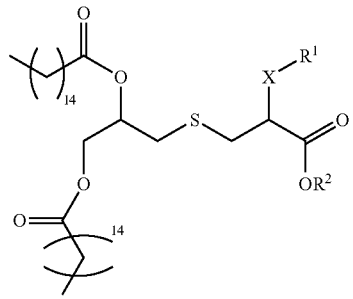

wherein X is hydrazide or amine; and $R^1$ is the polymer or linker and is joined to X by the labile bond, and $R^2$ is hydrogen; or $R^1$ is a progroup joined to X by the labile bond, and $R^2$ is the polymer or linker.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Expression Vector

The polymer linked to the adjuvant prodrug can be complexed with an expression vector including a nucleic acid molecule encoding an antigen for which an immune response is desired. Suitable expression vectors include nucleic acid based expression vectors, such as DNA and RNA plasmid vectors.

In one non-limiting example, a disclosed immunogen is expressed using a pVRC8400 vector (described in Barouch et al., *J. Virol*, 79, 8828-8834, 2005, which is incorporated by reference herein) that has been modified to remove any CpG motifs.

In some embodiments, the expression vector is non- or weakly-immunogenic, that is it does not contain nucleic acid sequences that are known to induce an immune response to the nucleic acid itself (as opposed to any proteins encoded by the nucleic acid molecule). In several embodiments, the expression vector includes a CpG-free promoter (such as a CMV-EF1 that is free of CpG motifs) that drives gene expression in mammals, a CpG-free nucleic acid molecule encoding the antigen, a terminal polyA sequence, a CpG-free interferon S/MAR and Beta globin MAR sequence (to increase gene expression levels and plasmid persistence in mammalian cells), optionally a CpG-free Kanamycin resistance gene (for bacterial production of the expression vector), and/or a CpG-free R6K origin of replication (for bacterial production of the expression vector).

One of skill in the art can readily use the genetic code to construct a variety of functionally equivalent nucleic acids, such as nucleic acids which differ in sequence but which encode the same antibody sequence, or encode a conjugate or fusion protein including the nucleic acid sequence. Exemplary expression vector and nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids and expression vectors can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding an antigen can include a recombinant DNA which is incorporated into an expression vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

The expression vector includes sufficient cis-acting elements for expression; other elements for expression can be supplied by the host cell or in an in vitro expression system. Further, the nucleic acid molecule encoding the antigen included on the expression vector can be operatively linked to expression control sequences. An expression control sequence operatively linked to a coding sequence is positioned such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

In some embodiments, the nucleic acid molecule encodes a precursor of a disclosed antigen, that, when expressed in an appropriate cell, is processed into a disclosed antigen. For example, the nucleic acid molecule can encode an antigen with an N-terminal signal sequence for entry into the cellular secretory system that is proteolytically cleaved during processing encoded protein in the cell.

In some embodiments, the antigen is an antigen from an infectious agent, such as virus, a bacteria, or a fungus.

Non-limiting examples of infectious viruses include: Retroviridae (for example, human immunodeficiency viruses, such as HIV-1; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses, such as MERS, SARs, etc); Arboviruses (eastern equine, western equine, St. Louis, Venezuelan equine encephalitis, and West Nile viruses); Epstein-Barr virus; Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses).

In some non-limiting embodiments, the antigen is a human immunodeficiency virus protein or immunogenic portion thereof, such as a HIV-1 gag p41 protein, a HIV-1 gp120 protein, a HIV-1 gp41 protein, HIV-1 gp140, HIV-1 gp145, or a HIV-1 Env protein. In some non-limiting embodiments, the antigen is an influenza protein or immunogenic portion thereof, such as a hemagglutinin protein or a neuraminidase protein. In some non-limiting embodiments, the antigen is an Ebola protein or immunogenic portion thereof, such as a GP protein.

Non-limiting examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococci, Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Pseudomonas aeruginosa, Clositridium difficilie, Streptobacillus moniliformis, Treponema pallidium, Treponema pertenue, Leptospira*, and *Actinomyces israelli*.

In some non-limiting embodiments a *Mycobacterium tuberculosis* protein or immunogenic portion thereof, such as an ESAT-6 protein or a 85B protein.

Non-limiting examples of infectious fungi include, but are not limited to, *Cryptococcus neoformans, Histoplasma capsulatum, Coccidioides immitis, Blastomyces dermatitidis, Chlamydia trachomatis*, and *Candida albicans*.

Other infectious agents include *Plasmodium falciparum, Plasmodium vivax, Leishmania major, Trypanosoma cruzi, Giardia lablia*, and *Toxoplasma gondii*.

In additional embodiments, the antigen is a toxin or immunogenic portion thereof, such as a protein-based toxins produced by bacteria, such as Anthrax and Tetanus toxins. In additional embodiments, the antigen is a toxin or immunogenic portion thereof, such as a manmade toxin or drug of abuse, such as protein toxins (ricin).

In additional embodiments, the antigen is a tumor associated antigen or immunogenic portion thereof. For example, the antigen can be a conserved cancer-associated self-antigen, such as NYESO1 (testicular cancer), Na17 (melanoma), gp100 (melanoma). In additional embodiments, the antigen is a neoantigen that is a mutated self-protein that can be unique to a particular tumor or cancer from a particular individual.

In some embodiments, the antigen can be from a hematological tumor. Non-limiting examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the antigen can be from a solid tumor. Non-limiting examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

In some embodiments, the tumor associated antigen is from a breast cancer, such as a ductal carcinoma or a lobular carcinoma. In some embodiments, the tumor associated antigen is from a prostate cancer. In some embodiments, the tumor associated antigen is from a skin cancer, such as a basal cell carcinoma, a squamous cell carcinoma, a Kaposi's sarcoma, or a melanoma. In some embodiments, the tumor associated antigen is from a lung cancer, such as an adenocarcinoma, a bronchiolaveolar carcinoma, a large cell carcinoma, or a small cell carcinoma. In some embodiments, the tumor associated antigen is from a brain cancer, such as a glioblastoma or a meningioma. In some embodiments, the tumor associated antigen is from a colon cancer. In some embodiments, the tumor associated antigen is from a Liver cancer, such as a hepatocellular carcinoma. In some embodiments, the tumor associated antigen is from a pancreatic cancer. In some embodiments, the tumor associated antigen is from a Kidney cancer, such as a renal cell carcinoma. In some embodiments, the tumor associated antigen is from a Testicular cancer.

III. Methods of Eliciting an Immune Response

In several embodiments, an immunogenic composition including the polymer nanoparticles comprising polymer linked to adjuvant prodrug and complexed with an expression vector encoding an antigen as described herein may be administered to a subject to elicit an immune response in the subject to the antigen encoded by the expression vector. In additional embodiments, an immunogenic composition comprising an effective amount of a compound or a pharmaceutically acceptable salt therefor comprising the structure set forth as any one of Compounds 1, 13, or 15-28 can be administered to a subject to induce or enhance an immune response in the subject (such as an anti-tumor immune response). Subjects that can benefit from the disclosed methods include human and veterinary subjects. The immune response can be a protective immune response, for example a response that prevents or reduces subsequent infection with a virus including the antigen. In some embodiments, the immune response can be a therapeutic immune response, for example a response that treats or inhibits a tumor that expressed the antigen on its cell surface.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize the disease or condition. These and other routine methods allow the clinician to select patients in need of therapy using the methods and pharmaceutical compositions of the disclosure. In accordance with these methods and principles, an immunogenic composition comprising polymer linked to adjuvant prodrug and complexed with an expression vector encoding an antigen as described herein can be administered according to the teachings herein, or other conventional methods known to the person of ordinary skill in the art, as an independent prophylaxis or treatment program, or as a follow-up, adjunct or coordinate treatment regimen to other treatments.

The administration of a therapeutically effective amount of an immunogenic composition including polymer nanoparticles comprising polymer linked to adjuvant prodrug and complexed with an expression vector encoding an antigen as described herein can be for prophylactic or therapeutic purpose. When provided prophylactically, the immunogenic composition is provided in advance of any symptom, for example in advance of infection or development of a tumor. The prophylactic administration of the immunogenic composition serves to prevent or ameliorate subsequent development of the disease or condition, such as to attenuate the anticipated severity, duration or extent of an infection or tumor, and/or any associated disease symptoms. When provided therapeutically, the immunogenic composition is provided at or after the onset of a symptom of disease or condition, for example after development of a symptom of infection, or diagnosis of infection, or development of a symptom of a tumor, or diagnosis of a tumor. Treatment of the infection or tumor can include delaying and/or reducing signs or symptoms of the infection or tumor in the subject. In some examples, treatment using the methods disclosed herein prolongs the time of survival of the subject.

The immunogenic composition can be used in coordinate immunization protocols or combinatorial formulations. In certain embodiments, novel combinatorial immunogenic compositions and coordinate immunization protocols employ separate immunogens or formulations, each directed toward eliciting an immune response against the antigen of interest, such as an immune response to a particular virus or tumor. Separate immunogenic compositions that elicit the immune response can be combined in a polyvalent immunogenic composition administered to a subject in a single immunization step, or they can be administered separately (in monovalent immunogenic compositions) in a coordinate immunization protocol.

The actual dosage of polymer nanoparticles comprising polymer linked to adjuvant prodrug and complexed with an expression vector encoding an antigen as described herein will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including polymer nanoparticles comprising polymer linked to adjuvant prodrug and complexed with an expression vector encoding an antigen as described herein can be used in coordinate (or prime-boost) vaccination protocols or combinatorial formulations. There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, a therapeutically effective amount of a immunogenic composition including polymer nanoparticles of an expression vector delivery system complexed with an expression vector encoding an antigen as described herein can be administered to a subject to treat or inhibit an infectious agent in a subject. The subject can be selected for treatment that has, is suspected of having or is at risk of developing an infection with the infectious agent. In some embodiments, the infectious agent is a virus, a bacteria, or a fungus as described above, and the antigen included on the expression vector is antigen from the particular virus, bacteria, or fungus.

In some embodiments, a therapeutically effective amount of a immunogenic composition including polymer nanoparticles of an expression vector delivery system complexed with an expression vector encoding an antigen as described herein can be administered to a subject to treat or inhibit a tumor and/or a cancer in a subject. The subject can be selected for treatment that has, is suspected of having or is at risk of developing the tumor and/or cancer. In some embodiments, treating the tumor and/or cancer in the subject decreases growth and/or proliferation of the tumor. The tumor can be any tumor of interest and can be benign or malignant.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

Treatment initiated after the development of a condition, such as malignant cancer, may result in decreasing the severity of the symptoms of one of the conditions, or completely removing the symptoms, or reducing metastasis, tumor volume or number of tumors. In some example, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

Subjects can be screened prior to initiating the disclosed therapies, for example to determine whether the subject has a tumor. The presence of a tumor can be determined by methods known in the art, and typically include cytological and morphological evaluation. The tumor can be an established tumor. The cells can be in vivo or ex vivo, including cells obtained from a biopsy. The presence of a tumor indicates that the tumor can be treated using the methods provided herein.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth, or the amount that is effective at reducing a sign or a symptom of the tumor. In another embodiment, a therapeutically effective amount is the amount necessary to inhibit infection by an infectious agent, or the amount that is effective at reducing a sign or a symptom of the infection. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or which reduce the load of infectious agent in the subject.

The actual dosage of the immunogenic composition including polymer nanoparticles of an expression vector delivery system complexed with an expression vector encoding an antigen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects.

Dosage can be varied by the attending clinician to maintain a desired concentration at a target site. Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used. In some embodiments, the polymer nanoparticles including the adjuvant prodrug can be co-administered with the expression vector (e.g., by administering an admixed composition) and intracellular delivery of the expression vector can be accomplished using endoscopic electroporation, such as with the EndoVe system (see, e.g., Forde et al., *Molecular Therapy Methods & Clinical Development*, 1, 14012, 2014; and Lee et al., *Hum Vaccin Immunother.*, 11(8):1889-1900, 2015, each of which is incorporated by reference herein). The disclosed therapeutic agents can be formulated in unit dosage form suitable for individual administration of precise dosages. In addition, the disclosed therapeutic agents may be administered in a single dose or in a multiple dose schedule.

In some embodiments, the disclosed methods include providing surgery, radiation therapy, and/or chemotherapeutics to the subject in combination with administration of a disclosed compound or composition containing the compound. Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

Non-limiting examples of additional therapeutic agents that can be used with the combination therapy include microtubule binding agents, DNA intercalators or crosslinkers, DNA synthesis inhibitors, DNA and RNA transcription inhibitors, antibodies, enzymes, enzyme inhibitors, gene regulators, angiogenesis inhibitors, and proteosome inhibitors (such as bortezomib or carfilzomib). These agents (which are administered at a therapeutically effective amount) and treatments can be used alone or in combination. For example, any suitable anti-cancer or anti-angiogenic agent can be administered in combination with the antibodies, conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

A. Additional Embodiments

The following additional embodiments concerning methods of inducing an immune response are also provided.

Clause 1. A method of inducing an immune response to an antigen in a subject, comprising administering to a target location in the subject a therapeutically effective amount of an immunogenic composition comprising:
  polymer nanoparticles comprising a polymer with neutral charge linked to an adjuvant prodrug; and
  an expression vector comprising a nucleic acid molecule encoding the antigen; and
  wherein
  the polymer linked to the adjuvant prodrug can form the polymer nanoparticles under physiological conditions;
  the polymer nanoparticles can enter cells under physiological conditions;

cleavage of an enzyme-degradable labile bond on the adjuvant prodrug by an intracellular enzyme activates the adjuvant to enhance the immune response to the antigen in the subject.

Clause 2. The method of clause 1, wherein the expression vector is non-immunogenic, optionally wherein the expression vector does not comprise any CpG motifs.

Clause 3. The method of any of the prior clauses, wherein the expression vector is a plasmid expression vector.

Clause 4. The method of any of the prior clauses, wherein:
the adjuvant prodrug is linked to a linker by the enzyme-degradable labile bond and the linker is linked to the polymer; and
cleavage of the enzyme-degradable labile bond by the intracellular enzyme activates the adjuvant and releases the adjuvant from the polymer.

Clause 5. The method of any of the prior clauses, wherein the expression vector is admixed with the polymer nanoparticles in the composition.

Clause 6. The method of clause 5, wherein the polymer is a hydrophilic polymer.

Clause 7. The method of clause 6, wherein the hydrophilic polymer is a poly(N-(2-hydroxypropyl(methacrylamide)) (pHPMA)-based co-polymer.

Clause 8. The method of any of the prior clauses, wherein the ratio of adjuvant prodrug to monomer of the polymer is from 1:100 to 1:1 mol/mol, optionally wherein the ratio of adjuvant prodrug to monomer of the polymer is from 1:20 to 1:10 mol/mol.

Clause 9. The method of any of the prior clauses, wherein the polymer comprises a plurality of monomers comprising from 5 monomers to 500 monomers.

Clause 10. The method of any of the prior clauses, wherein administering to a target location in the subject a therapeutically effective amount of an immunogenic composition comprises electroporation.

Clause 11. The method of any of the prior clauses, wherein the adjuvant prodrug is activated to enhance the immune response from 1-10 days following administration of the immunogenic composition to the subject, optionally wherein the adjuvant prodrug is activated to enhance the immune response from 5-10 days following administration of the immunogenic composition to the subject.

Clause 12. The method of any of the prior clauses, wherein the adjuvant prodrug is not activated to enhance the immune response until after the nucleic acid molecule encoding the antigen is expressed in the subject.

Clause 13. The method of any one of the prior clauses, wherein the enzyme-degradable labile bond is a protease-cleavable labile bond, and wherein cleavage of the protease-cleavable labile bond by an intracellular protease activates the adjuvant to induce the immune response against the antigen in the subject.

Clause 14. The method of any of the prior clauses, wherein the intracellular protease is a cathepsin.

Clause 15. The method of clause 14, wherein the linker comprises a cathepsin-cleavable peptide comprising L-amino acids or D-amino acids comprising the amino acid sequence set forth as one of: KPLR (SEQ ID NO: 2), KLRP (SEQ ID NO: 3), SLVR (SEQ ID NO: 4), or SLRV (SEQ ID NO: 5), and cathepsin cleavage of the peptide cleaves the labile bond and activates the adjuvant.

Clause 16. The method of any of the prior clauses, wherein the adjuvant prodrug comprises a pattern recognition receptor agonist.

Clause 17. The method of clause 16, wherein the pattern recognition receptor agonist comprises a toll-like receptor (TLR) agonist, a Stimulator of Interferon Genes (STING) agonist, a C-type lectin receptor (CLR) agonist, a RIG-I-like receptor (RLR) agonist, or a NOD-like receptor (NLR) agonist.

Clause 18. The method of clause 17, wherein the toll-like receptor agonist is a toll-like receptor 7/8 agonist.

Clause 19. The method of clause 18, wherein the toll-like receptor 7/8 agonist comprises a formula:

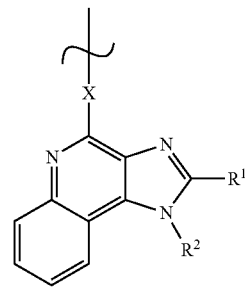

wherein:
X is amine or hydrazine;
$R^1$ is selected from one of hydrogen, optionally-substituted lower alkyl, or optionally-substituted lower ether;
$R^2$ is selected from one of hydrogen, optionally-substituted lower alkyl, optionally substituted aralkyl, optionally substituted benzyl, optionally substituted arylamine, or optionally substituted lower alkylamine; and wherein:
(a) the polymer or linker is joined to X by the labile bond; or
(b) the polymer or linker is joined to one of $R^1$ or $R^2$, and X is joined to a progroup by the labile bond.

Clause 20. The method of clause 19, wherein
$R^1$ is selected from one of:
hydrogen,

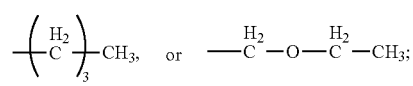

and
$R^2$ is selected from one of:
hydrogen,

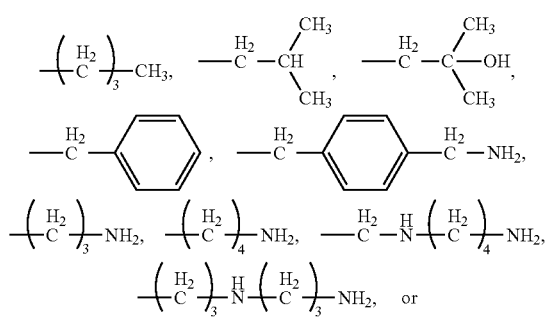

-continued

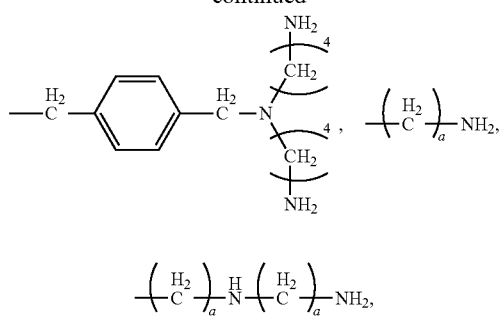

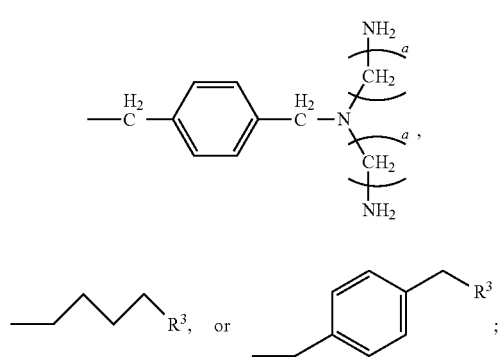

and wherein a, if present, is independently 1 to 4;

wherein R³, if present, is selected from one of

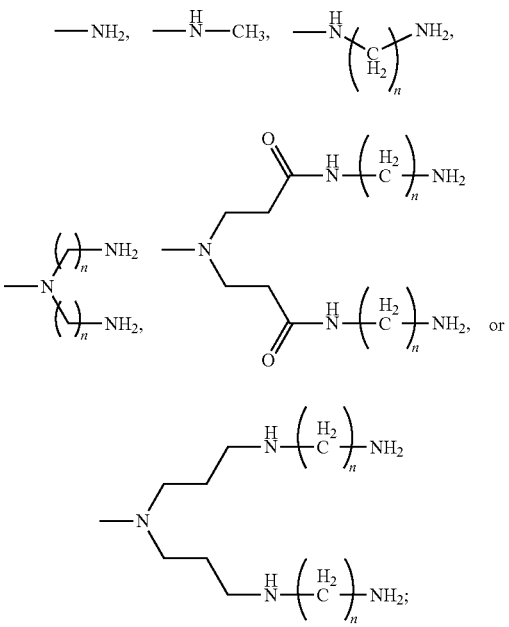

and wherein n, if present, is independently 1 to 12.

Clause 21. The method of clause 19, wherein the linker is joined to X by the labile bond, and wherein the toll-like receptor 7/8 agonist comprises a formula set forth as one of:

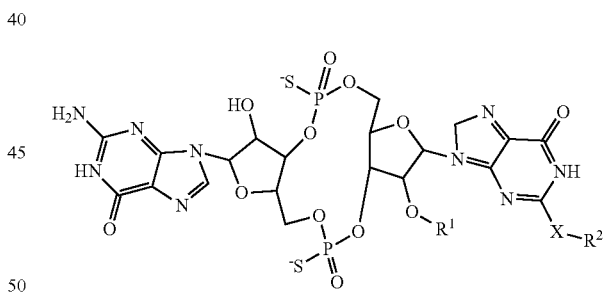

Clause 22. The method of clause 15, wherein the polymer linked to the toll-like receptor 7/8 agonist comprises a structure set forth as one PEI03, PEI04, PEI05, PEI06, PEI07, PL03, PL04, PL05, PL06, PL07, PL08, PL09, or PL10.

Clause 23. The method of clause 17, wherein the STING agonist is a cyclic-dinucleotide (CDN) STING agonist.

Clause 24. The method of clause 23, wherein the CDN STING agonist comprises a formula:

wherein:
X is hydrazide or amine; and one of (a)-(d):
(a) $R^1$ is hydrogen, and $R^2$ is the polymer or linker and is joined to X by the labile bond;
(b) $R^1$ is the polymer or linker and is joined to the ribose by the labile bond, and $R^2$ is hydrogen;
(c) $R^1$ is the polymer or linker and is joined to the ribose, and $R^2$ is a progroup joined to X by the labile bond; or
(d) $R^1$ is a progroup joined to the ribose by the labile bond, and $R^2$ is the polymer or linker.

Clause 25. The method of clause 17, wherein the toll-like receptor agonist is a toll-like receptor 1/2 agonist.

Clause 26. The method of clause 25, wherein the toll-like receptor 1/2 agonist comprises a formula:

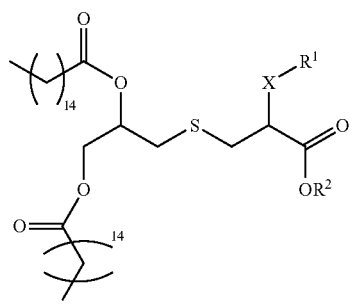

wherein X is hydrazide or amine; and one of (a) or (b):
(a) $R^1$ is the polymer or linker and is joined to X by the labile bond, and $R^2$ is hydrogen; or
(b) $R^1$ is a progroup joined to X by the labile bond, and $R^2$ is the polymer or linker.

Clause 27. The method of any of the prior clauses, wherein the antigen is a tumor associated antigen, a viral antigen, a bacterial antigen, or a protozoan antigen.

IV. Poly(Basic) Adjuvant Compounds

Disclosed therein are novel poly(basic) imidazoquinoline compounds, or a pharmaceutically acceptable salt thereof, for use as adjuvants to induce or enhance an immune response in a subject. The compounds are TLR-7/8 agonists. The cell can be in vitro or in vivo.

In some embodiments, the TLR-7/8a compound, or a pharmaceutically acceptable salt or ester thereof, having a formula of one of:

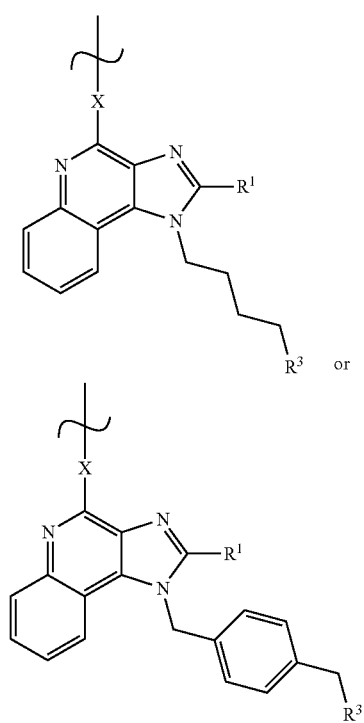

wherein the $R^1$ can be selected from hydrogen,

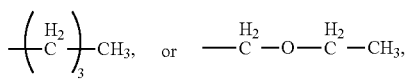

and/or $R^3$ can be selected from one of

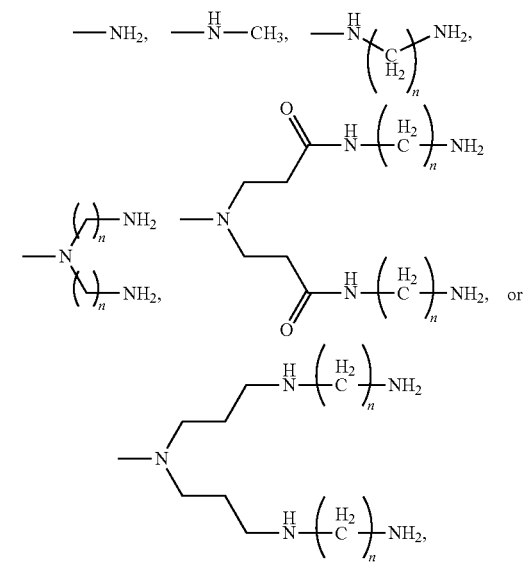

and wherein n is from 1 to 12, such as 1 to 4, for example 1 or 2, and X is amino or hydrazine. In several such embodiments, $R^1$ is

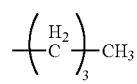

and $R^2$ is amino or hydrazine.

In some embodiments, the TLR-7/8a compound, or a pharmaceutically acceptable salt or ester thereof, having a formula of one of:

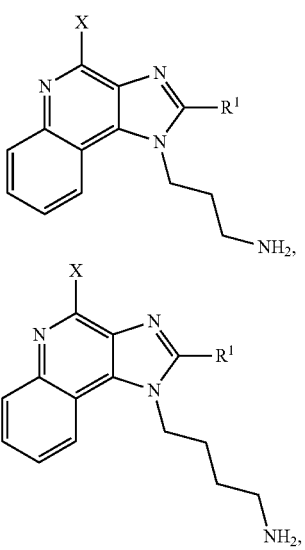

-continued
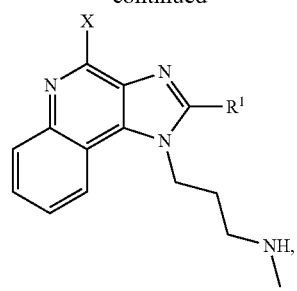
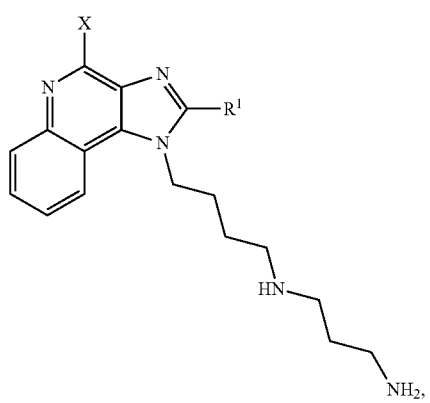
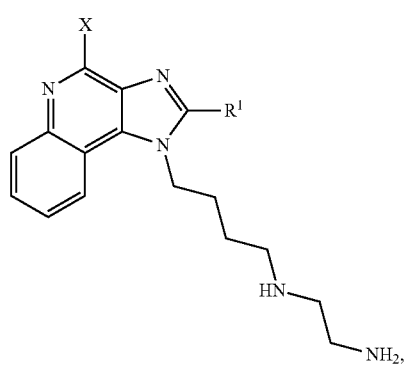
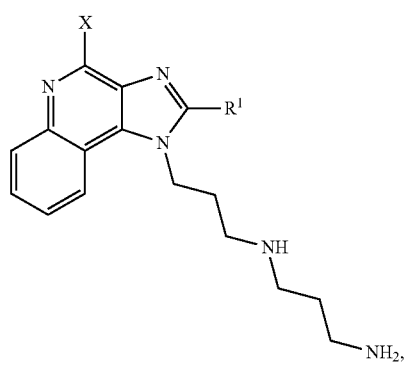
-continued
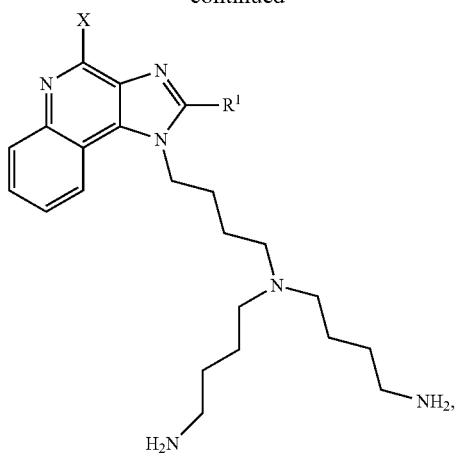
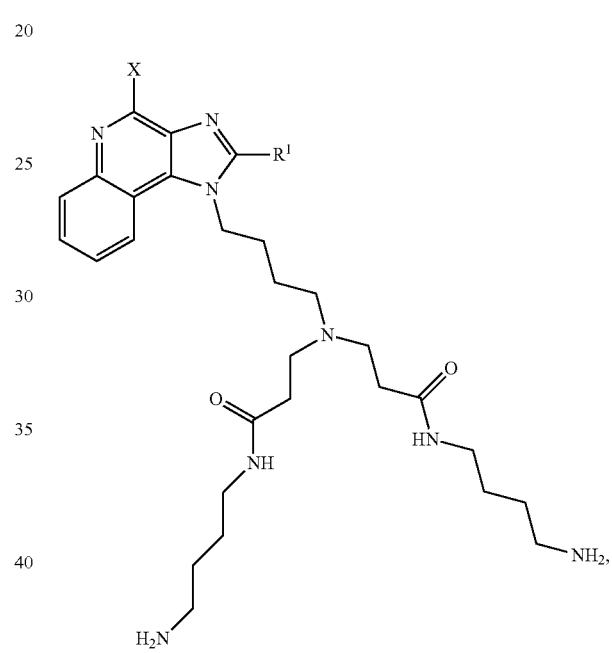
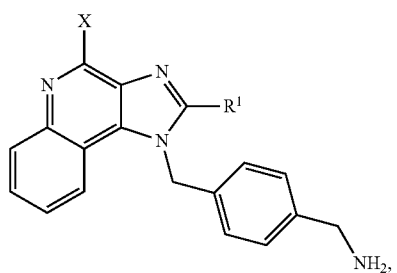
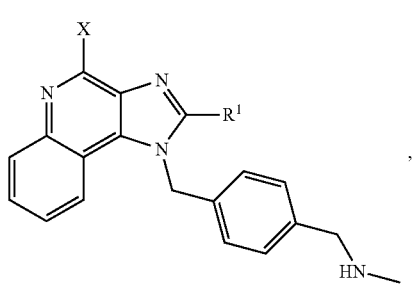

-continued
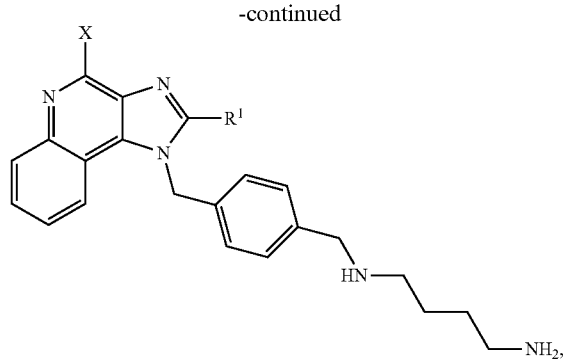
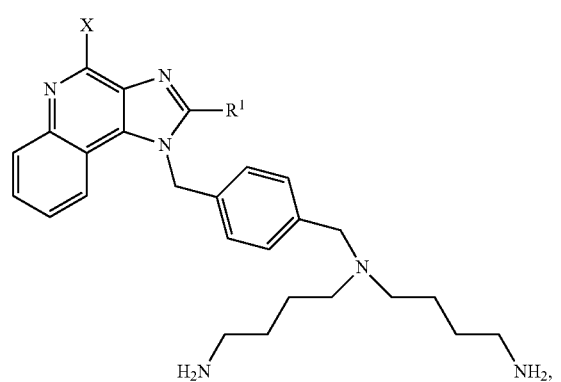
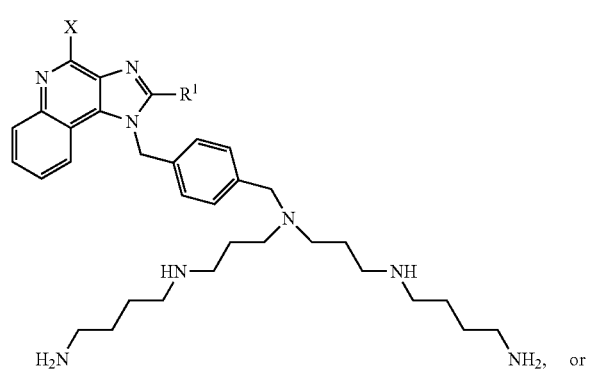
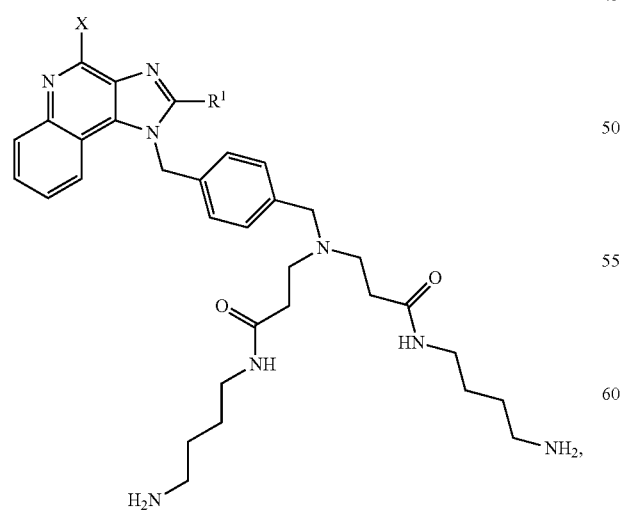
wherein R¹ is one of hydrogen,
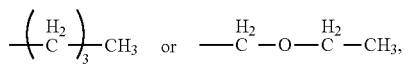
and X is amino or hydrazine. In several such embodiments, R¹ is
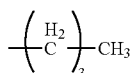
and R² is amino or hydrazine.
In some embodiments, the TLR-7/8a compound, or a pharmaceutically acceptable salt or ester thereof, having a structure of one of:
(1)
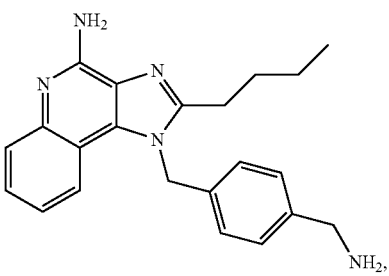
(13)
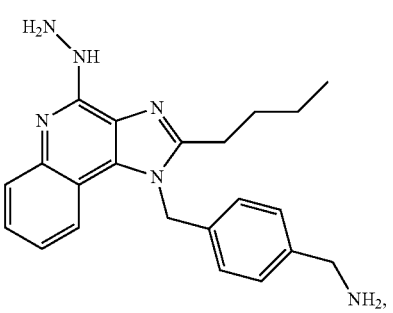
(15)
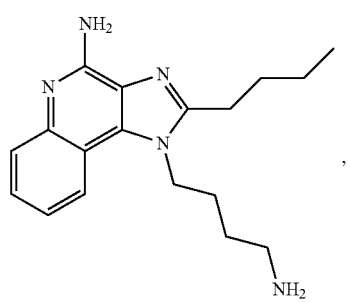

-continued
(16)
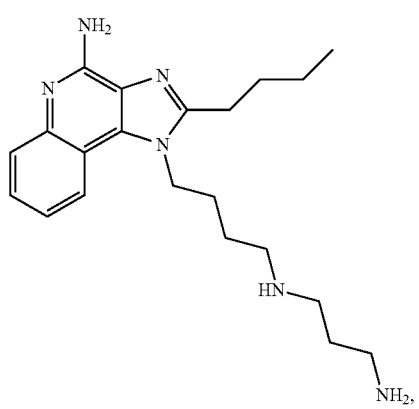
(17)
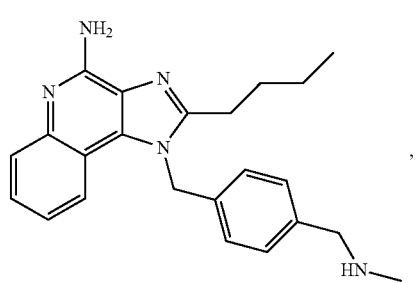
(18)
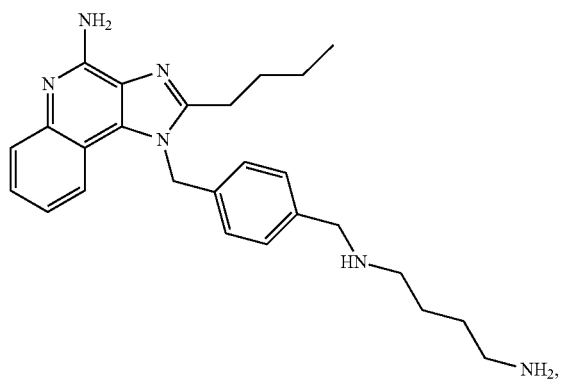
(19)
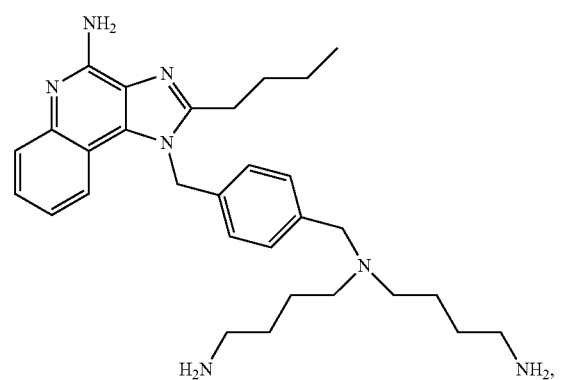
-continued
(20)
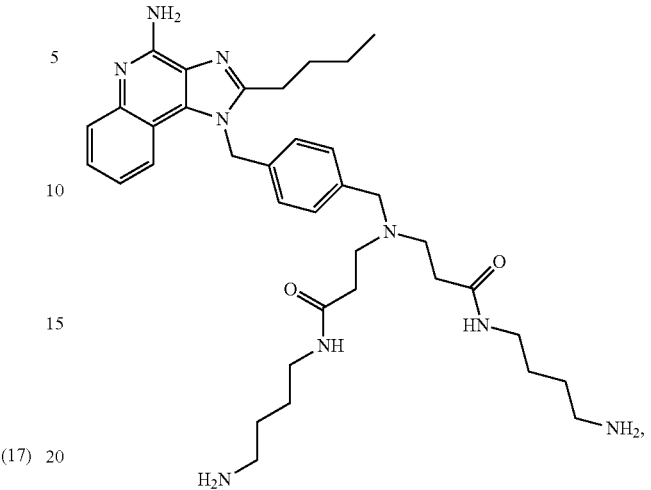
(21)
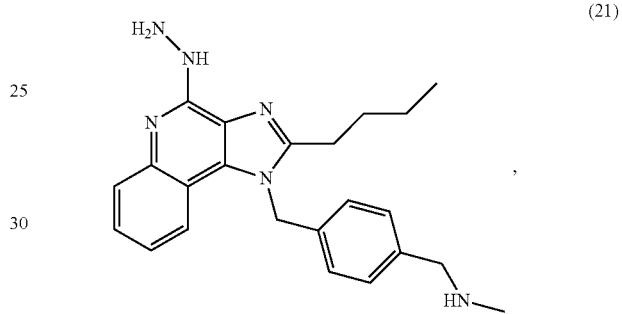
(22)
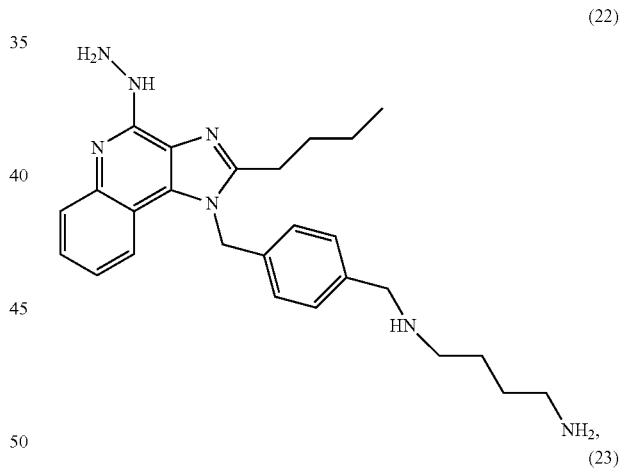
(23)
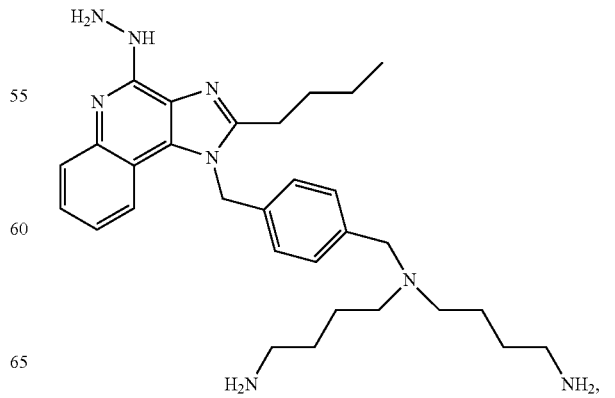

(24)
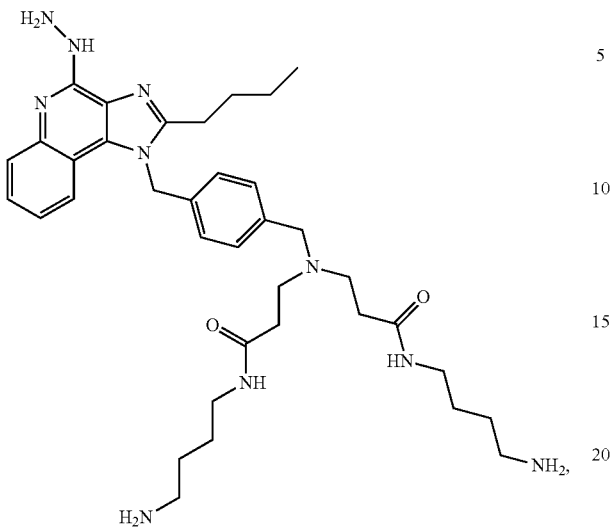

(27)
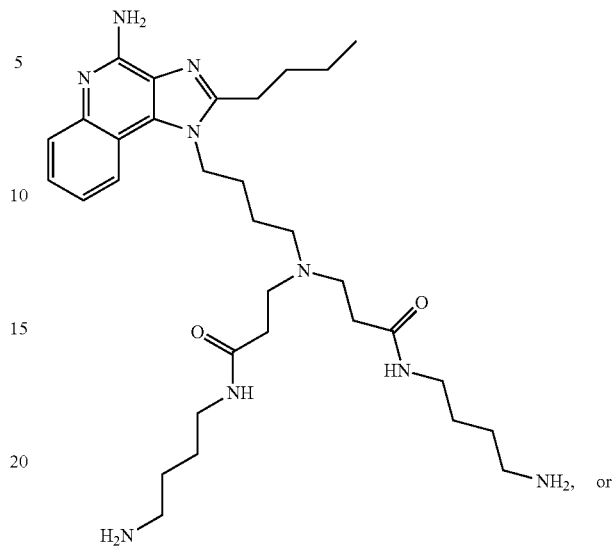

, or

(25)
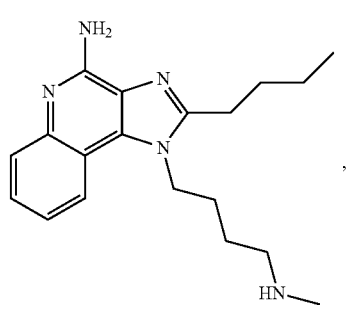

(28)

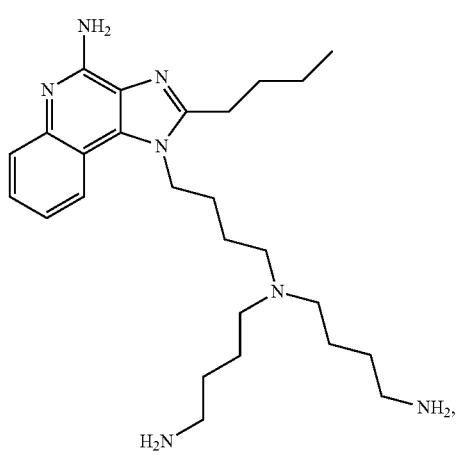

(26)

Polybasic imidazoquinolines can be used as adjuvants in combination with an antigen for inducing an immune response in a subject (see, for example, Czarniecki, M., et al., *J. Med. Chem,* 51, 6621-6626 (2008) and Gerster, J., F., et al. *J. Med. Chem,* 48, 3481-3491 (2005)

In some embodiments, the disclosed the TLR-7/8a compounds can be formulated with an antigen from a hematological tumor for use as a tumor vaccine. Non-limiting examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the disclosed TLR-7/8a compounds can be formulated with an antigen from a solid tumor. Non-limiting examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

In some embodiments, the tumor associated antigen formulated with the TLR-7/8a compound is from a breast cancer, such as a ductal carcinoma or a lobular carcinoma. In some embodiments, the tumor associated antigen is from a prostate cancer. In some embodiments, the tumor associated antigen is from a skin cancer, such as a basal cell carcinoma, a squamous cell carcinoma, a Kaposi's sarcoma, or a melanoma. In some embodiments, the tumor associated antigen is from a lung cancer, such as an adenocarcinoma, a bronchiolaveolar carcinoma, a large cell carcinoma, or a small cell carcinoma. In some embodiments, the tumor associated antigen is from a brain cancer, such as a glioblastoma or a meningioma. In some embodiments, the tumor associated antigen is from a colon cancer. In some embodiments, the tumor associated antigen is from a Liver cancer, such as a hepatocellular carcinoma. In some embodiments, the tumor associated antigen is from a pancreatic cancer. In some embodiments, the tumor associated antigen is from a Kidney cancer, such as a renal cell carcinoma. In some embodiments, the tumor associated antigen is from a Testicular cancer.

In some embodiments, the TLR-7/8a compounds as adjuvants can be formulated with a peptide or protein antigen from an infectious agent, such as virus, a bacteria, or a fungus.

Non-limiting examples of infectious viruses include: Retroviridae (for example, human immunodeficiency viruses, such as HIV-1; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses, such as MERS, SARs, etc); Arboviruses (eastern equine, western equine, St. Louis, Venezuelan equine encephalitis, and West Nile viruses); Epstein-Barr virus; Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses).

In some embodiments, the TLR-7/8a compound can be formulated with an antigen from human immunodeficiency virus protein, such as a HIV-1 gag p41 protein, a HIV-1 gp120 protein, a HIV-1 gp41 protein, HIV-1 gp140, HIV-1 gp145, or a HIV-1 Env protein. In some embodiments, the antigen comprises an antigen from an influenza protein, such as a hemagglutinin protein or a neuraminidase protein. In some embodiments, the antigen comprises an antigen from an Ebolavirus protein, such as a GP protein.

In some embodiments, the peptide or protein antigen combined with the TLR-7/8a compound adjuvant comprises an antigen from an infectious bacterial protein. Non-limiting examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococci, Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Pseudomonas aeruginosa, Clositridium Streptobacillus moniliformis, Treponema pallidium, Treponema pertenue, Leptospira*, and *Actinomyces israelli*.

In some embodiments the antigen comprises an antigen from a *Mycobacterium tuberculosis* protein, such as an ESAT-6 protein or a 85B protein.

In some embodiments, the antigen comprises an antigen from an infectious fungi protein. Non-limiting examples of infectious fungi include, but are not limited to, *Cryptococcus neoformans, Histoplasma capsulatum, Coccidioides immitis, Blastomyces dermatitidis, Chlamydia trachomatis*, and *Candida albicans*.

Other infectious agents include *Plasmodium falciparum, Plasmodium vivax, Leishmania major, Trypanosoma cruzi, Giardia lablia*, and *Toxoplasma gondii*.

In additional embodiments, the antigen is a toxin or immunogenic portion thereof, such as a protein-based toxins produced by bacteria, such as Anthrax and Tetanus toxins. In additional embodiments, the antigen is a toxin or immunogenic portion thereof, such as a manmade toxin or drug of abuse, such as protein toxins (ricin).

Imidazoquinolines and other agonists of Toll like receptors are known to directly mediate tumor regression through innate immune cell stimulation (See Singh, M., et al., *J. Immunology*, 193, 4722-4731 (2014)). Accordingly, any of the TLR-7/8a compounds described herein can be administered directly (intratumorally) into a tumor for treatment purposes. The acidic tumor environment could allow for improved retention of the TLR-7/8a compound (which is a polybasic imidazoquinoline), therefore prolonging activity of the agonist in the tumor environment. In some embodiments the TLR-7/8a compound agonist can be directly injected into a solid tumor. Non-limiting examples of solid tumors that can be treated with a therapeutically effective amount of one of the disclosed TLR-7/8a compounds include HPV+ head and neck tumors or cervical cancers that are directly accessible to injection.

V. Compositions

Another aspect of the disclosure includes pharmaceutical compositions (such as immunogenic compositions) prepared for administration to a subject and which include a therapeutically effective amount of one or more of polybasic TLR-7/8 adjuvants, or the expression vector delivery systems and/or expression vectors disclosed herein. For example, the composition can include polymer nanoparticles including expression vector delivery system as disclosed herein linked to an expression vector of interest, or admixed with the expression vector. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, PA, 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N, N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-co-lactic acid), poly(epsilon-caprolactone-co-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, poly-orthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

In some embodiments, the composition can be formulated for nasal administration or otherwise administered to the lungs of a subject by any suitable means, e.g., administered by an aerosol suspension of respirable particles comprising the nanoparticles, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, Drug Delivery to the Respiratory Tract, Ellis Horwood (1987); Gonda (1990) Critical Reviews in Therapeutic Drug Carrier Systems 6:273-313; and Raeburn et al., J. Pharmacol. Toxicol. Meth. 27:143 (1992). Aerosols of liquid particles comprising the nanoparticles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the nanoparticles can likewise be produced with any solid particulate medicament aerosol generator, by techniques known in the pharmaceutical art.

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

The following examples are provided to illustrate particular features of certain embodiments, but the scope of the claims should not be limited to those features exemplified.

Example 1

Prodrug Gene Delivery Systems for Delayed Onset Immune Activation

Cancer causes about 25% of deaths in the United States. Historically, surgery, chemotherapy and radiation were the primary modalities used for treating many cancers. Such therapies have limited efficacy against solid tumors that have metastasized and often lead to limiting toxicities due the non-specific nature of the treatments Immunotherapies have emerged as a promising alternative approach to these traditional treatment modalities and encompass a broad range of technologies that harness natural immunological mechanisms to mediate cancer-specific killing (Topalian et al., *J Clin Oncol* 29, 4828-4836, 2011). Of the cancer immunotherapies, adoptive transfer of tumor specific lymphocytes has been shown to mediate regression and even cure in up to 20% of subjects with melanoma. Recently, antibodies that improve T cell function in vivo reducing inhibition mediated by CTLA4 and PD1, collectively termed checkpoint inhibitors, have been shown to induce anti-tumor effects in ~30% of subjects with specific solid tumors. To further improve outcomes for the large patient population for which checkpoint inhibitors are presently not effective, additional approaches for inducing tumor specific lymphocytes will need to be employed that can then work alone or synergistically in combination with checkpoint inhibitors.

Generating tumor specific T cells directed against a specific type of cancer cell requires identification of antigens that are expressed by the cancer cells and are recognized by patient's own T cells. These so-called tumor-associated antigens can either be self-antigens that are expressed by both normal cells and cancer cells, or neoantigens, which are mutated self-antigens that are only present on the cancer cells. Until recently, the majority of cancer vaccine strategies have used tumor-associated self-antigens to generate cancer-specific T cell responses (Aranda et al. *Oncoimmunology* 2, e26621, 2013). While adoptive transfer of tumor specific lymphocytes against self-antigens can be effective, these approaches can also result in significant toxicity and morbidity due to immune activation against normal cells expressing self-antigen. As an alternative to self-antigens, recent advances in DNA and RNA sequencing technologies have been used to identify tumor-specific neoantigens from patient tumor samples (see, e.g., Yadav et al. *Nature* 515, 572-576, 2014). Based on these unique antigens, predictive algorithms are then applied to determine which sequences of the neoantigens have the potential to be immunogenic in the context of the patient's own histocompatibility loci. Such tumor specific neoantigens can then be formulated as a subunit vaccine and given to patients to generate lymphocyte responses against these neoantigens. Data show that tumor specific neo-antigens are distinct across all cancers. Thus, commercial development of an immunization protocol targeting tumor neoantigens may require an individualized vaccine approach that is relatively rapid, safe and scalable for broad application.

Tumor neoantigens can be given as a subunit vaccine to patients using either a peptide- or gene delivery system. Peptide-based vaccines are chemically well defined and can be produced rapidly using solid-phase peptide synthesis. The disadvantage of peptide-based vaccines is that the broad physical and chemical diversity of peptide sequences makes formulation strategies unpredictable and responses variable depending on the pharmacokinetic properties of the peptide. Moreover, peptide-based vaccines may be limited for generating sufficient magnitude of T cell responses against the cancer primarily due to inefficient loading on MHC-I class restricted molecules, a process referred to as antigen cross-presentation. In contrast, gene based delivery of constructs encoding tumor neoantigens by viral vectors (e.g., Adenovirus) offer the advantages of generating more potent neoantigen-specific T cells. A limitation of using viral vectors is that anti-vector antibody responses may be present in the individual already from prior natural exposure and/or will be generated by the vaccination itself thereby limiting its use for repetitive immunization which may be needed to sustain protective anti-tumor T cell immunity. Additionally, the lead-time required, and costs associated with generating viruses expressing patient-specific neoantigens may be prohibitive to development since rapidly deployable technologies will likely be needed for patient-specific immunotherapy approaches.

DNA and RNA-based plasmids overcome many of the limitations of peptide and viral vector-based subunit vaccine systems. Accordingly, nucleic acid-based approaches (1) offer the ability to be rapidly deployed and provide predictable physicochemical behavior during formulation; (2) provide endogenous production of the tumor neoantigen, which promotes presentation of the antigen to T cells; and, (3) non-viral gene delivery approaches can be used repeatedly in patients to boost T cell responses, which may be required for maintaining CTLs above a protective threshold to clear rapidly growing cancerous lesions.

While DNA and RNA-based systems offer many advantages to peptide and viral-based vaccines, the major limitation is that current strategies for delivering adjuvants with DNA or RNA are either insufficiently immunostimulatory for promoting strong CTLs against the transgenic antigen expressed by the plasmid, or the adjuvants combined with the DNA or RNA limit expression of the plasmid before the transgenic antigen is produced. Vaccine adjuvants, such as imidazoquinoline-based Toll-like receptor 7 and 8 agonists (TLR-7/8a), that induce IL-12 and Type-I Interferons (IFNs) can be used to enhance CTLs against protein antigens. However, when combined with gene-delivery based vaccine systems (i.e., viral vectors, DNA or RNA), these same adjuvants can abrogate immune responses due to the capacity of Type-I IFNs to suppress endogenous production of the transgenic antigen. Thus, while Type-I IFNs are critical for promoting T cell responses to antigens, the antigen must first be produced by the gene delivery system before the onset of Type-I IFNs occurs. Therefore, one way to optimize T cell immunity with DNA- and RNA-based delivery systems is to control the temporal gene expression of the tumor antigen and timing of Type-I IFN so that transgenic antigens can be produced prior to the onset of Type-I IFNs.

Figure 2:
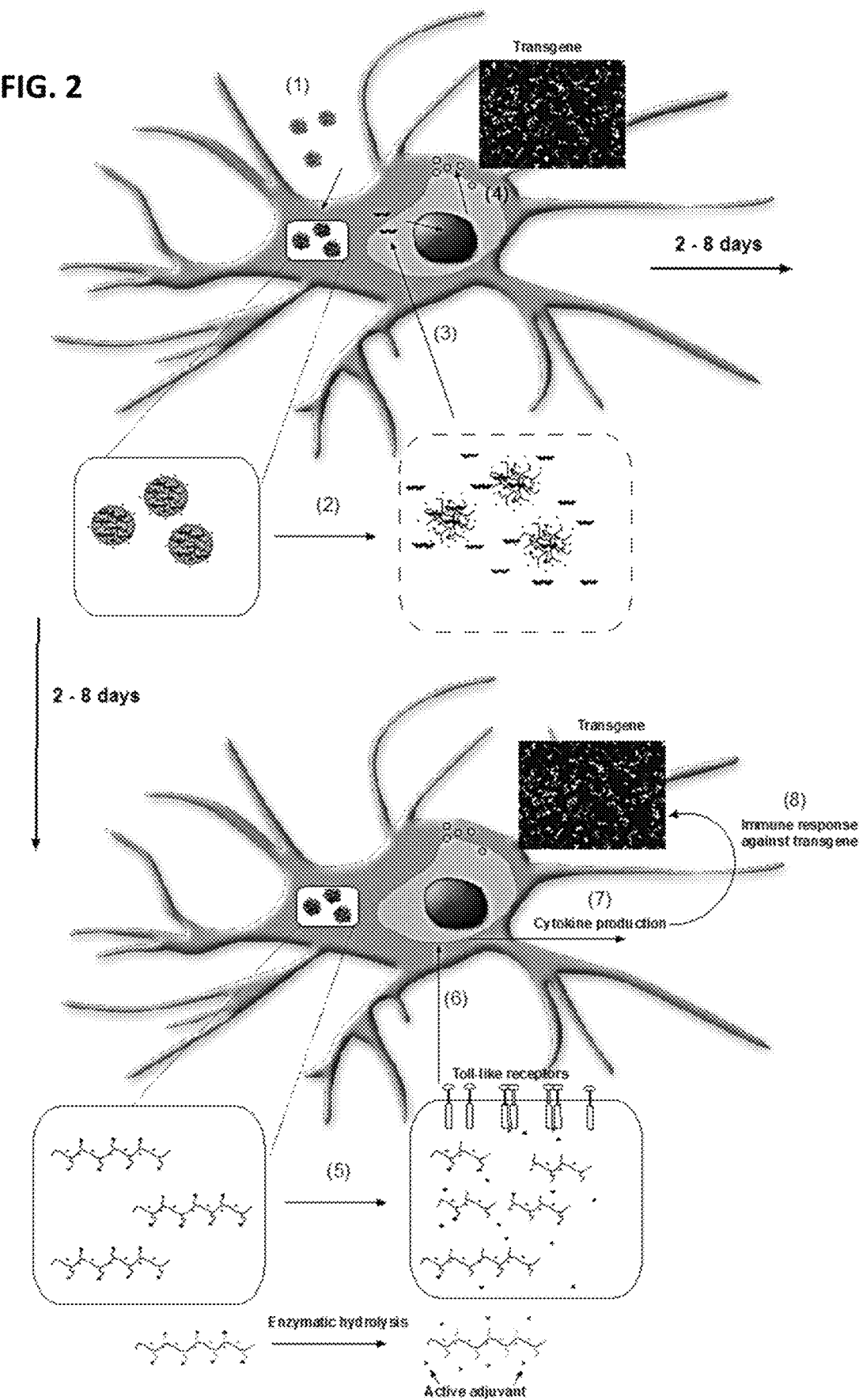
FIG. 2 is a cartoon schematic representing the proposed mechanism of action of the adjuvant prodrug system: (1) antigen presenting cells take up nanoparticles comprised of a cationic polymer linked to an adjuvant prodrug electrostatically complexed to a DNA-based expression vector; (2) buffering by the cationic polymer during endosomal acidification leads to endosomal swelling and allows for release of the co-delivered expression vector; (3) the expression vector is translocated to the nucleus and the transgene antigen is transcribed to RNA; (4) RNA encoding the antigen is translated to protein to produce the antigen encoded by the expression system; (5) over 2-8 days, the prodrug adjuvant is released from the polymer backbone and the active form of the adjuvants binds cognate TLRs in the endosome; (6) TLR signaling leads to immune activation, including antigen presentation to T cells and (7) cytokine production; (8) innate immune stimulation by the adjuvant drives adaptive immune responses against the transgene encoded by the expression vector.

A novel strategy for promoting enhanced T cell responses to gene-expressed antigens (such as antigens expressed from DNA or RNA plasmids) is to use a gene delivery system comprised of prodrug TLR-7/8a that are chemically linked to polymeric gene delivery systems based on either poly(ethylenimine) or Poly(Lysine) that can be linked to a gene expression vector (such as DNA or RNA) through electrostatic interactions to form polymer nanoparticles, sometimes referred to as Poly(plexes) (FIG. 1). The polymer nanoparticles administered to a host can be taken up by immune cells (such as an antigen presenting cell) wherein the buffering capacity of the particle can rupture the endosome and release the gene expression vector for expression in the cell (FIG. 2, top). Over several days, the adjuvant prodrug linked to the gene expression delivery system can be hydrolyzed by enzymes (e.g., cathepsins) to release the active form of the adjuvant that can bind to pattern recognition receptors and mediate an immune response (FIG. 2, bottom).

Based on recent studies defining structure-activity relationships for imidazoquinoline-based TLR-7/8a (FIG. 3) (Shukla et al., *J Med Chem* 53, 4450-4465, 2010; Gerster et al., *J Med Chem* 48, 3481-3491, 2005; Ryu et al., *Journal of the American Chemical Society* 136, 10823-10825, 2014), a series of active and prodrug forms of TLR-7/8a that were linked to PEI and PL-based polymers were produced through a process of combinatorial synthesis to generate 18 unique constructs. A subset of this material library was evaluated for the capacity to delay the onset of immune activation in vivo and to deliver DNA plasmids carrying reporter proteins.

Altogether, this study provides a chemical and structural basis for modulating the timing of onset of immune activity for generating robust T cell immunity to DNA-based subunit vaccines that could have important translational implications for improved delivery of neoantigens for personalized immunotherapy.

Materials and Methods

Synthesis of Conjugatable TLR-7/8a

Several conjugatable TLR-7/8a were prepared so that activity of the agonist is conserved following attachment to polymer-based gene delivery systems. These TLR-7/8a use a linker site that does not interfere with TLR-7/8 binding and, therefore, permits immediate onset immune activity when used with gene delivery systems. The synthesis, purification and characterization of these compounds are described below.

The benzyl amine group on compound (1) permits a chemically labile group that allows for attachment to linkers or directly to macromolecular and particulate delivery systems.

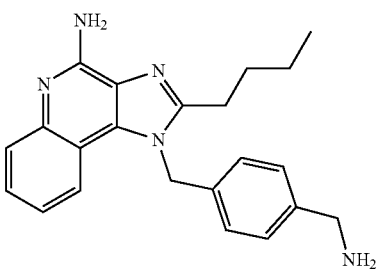

(1)

Synthesis of compound (1). The synthesis of 1-(4-(aminomethyl)benzyl)-2-butyl-1H-imidazo[4,5-c]quinolin-4-amine was carried out as previously described (See Shukla et al., *J Med Chem* 53, 4450-4465 (2010); Nanba, R. J., Iizuka, Takao (JP), Ishii, Takeo (JP) (TERUMO CORP (JP), 1999); Shukla et al., *Bioorg Med Chem Lett* 20, 6384-6386 (2010); each of which is incorporated by reference herein). $^1$H NMR (400 MHz, DMSO-d6) δ 7.77 (dd, J=8.4, 1.4 Hz, 1H), 7.55 (dd, J=8.4, 1.2 Hz, 1H), 7.35-7.28 (m, 1H), 7.25 (d, J=7.9 Hz, 2H), 7.06-6.98 (m, 1H), 6.94 (d, J=7.9 Hz, 2H), 6.50 (s, 2H), 5.81 (s, 2H), 3.64 (s, 2H), 2.92-2.84 (m, 2H), 2.15 (s, 2H), 1.71 (q, J=7.5 Hz, 2H), 1.36 (q, J=7.4 Hz, 2H), 0.85 (t, J=7.4 Hz, 3H). MS (APCI) calculated for $C_{22}H_{25}N_5$ m/z 359.2, found 360.3 (M+H)$^+$.

Compound (2) is a conjugatable TLR-7/8a with a terminal azide group that permits attachment to polymer-based gene delivery systems using "click chemistry" reactions.

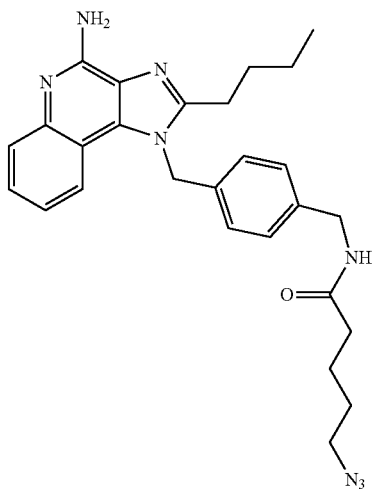

(2)

Synthesis of compound (2). To 2 mL of ethyl acetate was added 100 mg (0.28 mmol, 1 eq) of (1), 50 mg (0.14 mmol, 1 eq) of CDMT and 22 mg (0.15 mmol, 1.1 eq) of Azidopentanoic acid, followed by the dropwise addition of 20 μl (0.17 mmol, 1.2 eq) of NMM, while stirring vigorously. After 16 hours at room temperature, the reaction mixture was filtered and then washed 3×50 mL with 1 M HCl. The organic phase was dried with $Na_2SO_4$ and then evaporated to dryness. The resulting solid was purified by reverse phase HPLC chromatography using a 15-45% acetonitrile/H2O (0.05% TFA) gradient over 15 minutes. The resulting fractions were collected, frozen and lyophilized to obtain a spectroscopically pure (>95% at 254 nm) white solid. MS (APCI) calculated for $C_{27}H_{32}N_8O$ m/z 484.3, found 485.3 (M+H)$^+$.

Compound (3) is a conjugatable TLR-7/8a with an enzyme-degradable tetrapeptide (KPLR, SEQ ID NO: 2) linker. The KPLR (SEQ ID NO: 2) peptide that is recognized by cathepsin proteases localized to endosomal compartments of cells.

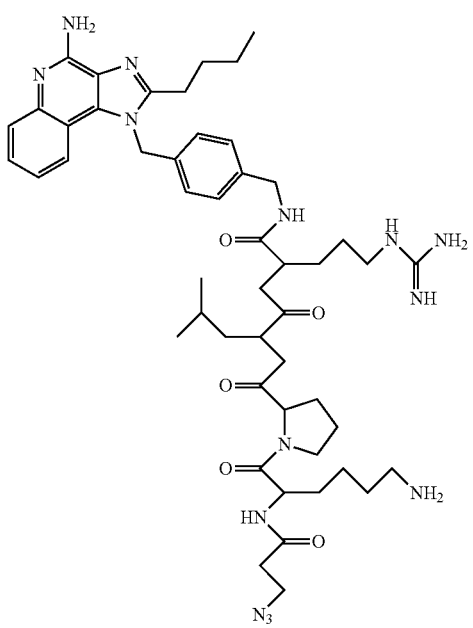

(3)

Synthesis of compound (3). To 2 mL of ethyl acetate was added 20 mg (0.055 mmol, 1.1 eq) of (1), 9 mg (0.061 mmol, 1 eq) of CDMT and 50 mg (0.051 mmol, 1 eq) of an azide-terminated tetrapeptide with protected side groups (X-KPLR(SEQ ID NO: 2)-COOH, where x=azido-pentanoic acid) and a free acid C-terminus, followed by the dropwise addition of 20 μl (0.17 mmol, 1.2 eq) of NMM, while stirring vigorously. After 16 hours at room temperature, the reaction mixture was filtered and then washed 3×50 mL with 1 M HCl. The organic phase was dried with $Na_2SO_4$ and then evaporated to dryness. The resulting solid was treated with 1 mL of an 88:5:5:2 solution of TFA/TIPS/Phenol/$H_2O$ to remove the protecting groups on the side chains of the tetrapeptide. After 1 h, the reaction mixture was added to 50 mL of ethyl ether and the de-protected product (3) precipitated from solution. The resulting crude product was purified by reverse phase HPLC chromatography using a 20-55% acetonitrile/$H_2O$ (0.05% TFA) gradient over 15 minutes (column=Zorbax SBC18 9.4×150 mm). The resulting fractions were collected, frozen and lyophilized to obtain a spectroscopically pure (>95% at 254 nm) white solid. MS (APCI) calculated for $C_{50}H_{74}N_{16}O_5$ m/z 978.6, found 979.7 (M+H)$^+$.

Synthesis of Conjugatable Prodrug TLR-7/8a

Figure 3A:
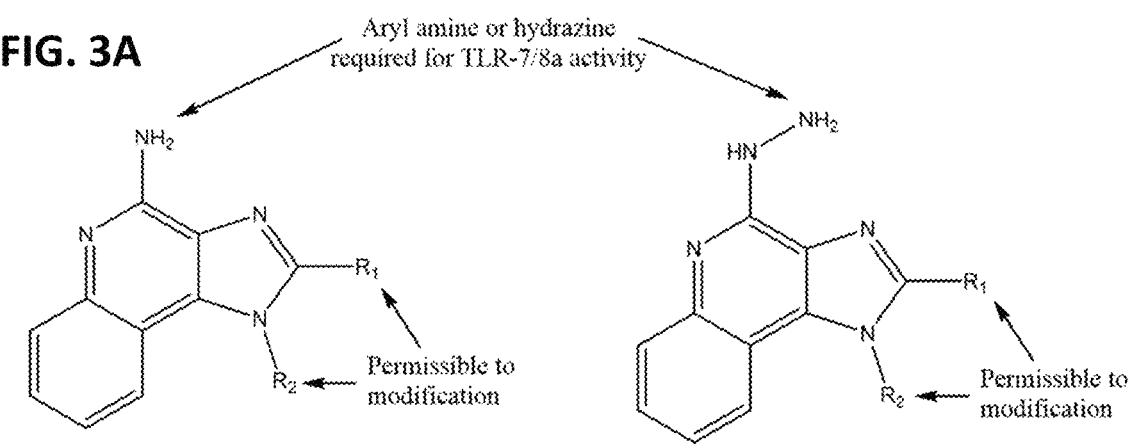
FIG. 3A-3C show generic structures of imidazoquinoline-based TLR-7/8 agonist (TLR-7/8a) as well as various linker groups that can be to attach the agonists to polymer carriers. Chemical modification of R1 and R2 is permissible, whereas modification of the aryl-amine abrogates activity. As disclosed herein, modification of the aryl-amine using a chemically labile bond provides a prodrug molecule that can be modulated to control the location and timing of activation of TLR-7/8a activity.
Figure 3B:
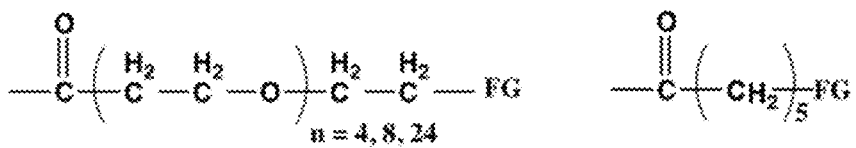
Figure 3B:
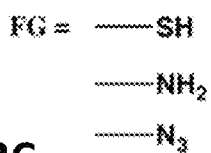
Figure 3B:
Figure 3C:
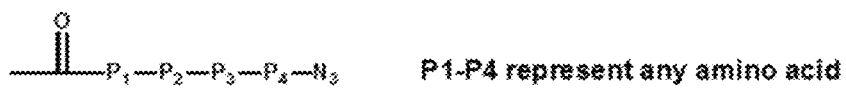
Figure 3C:
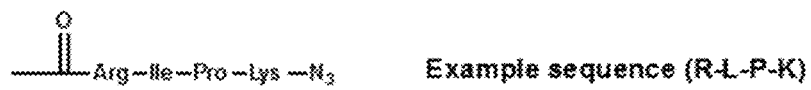
Figure 3C:
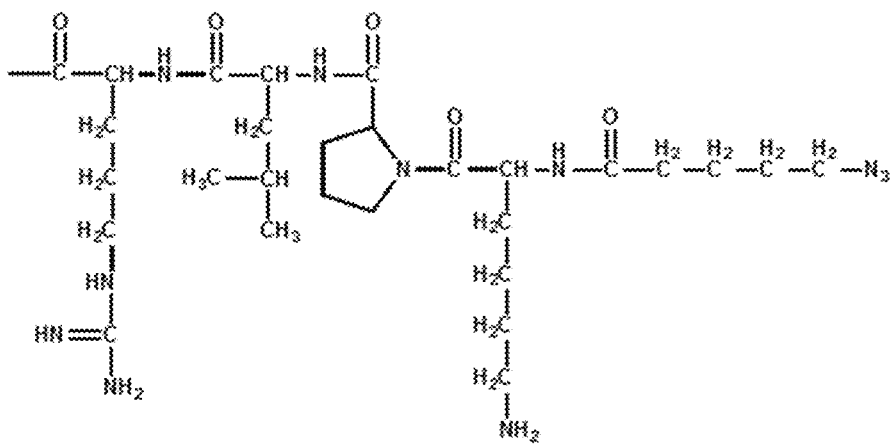

Conjugatable prodrug TLR-7/8a were prepared by attaching chemically labile linker groups to an aryl hydrazine on compound (4) (e.g., as shown in FIG. 3B), resulting in Linker group (L) functionalized TLR-7/8a that are inactive while the linker group is attached. The synthesis of (1-benzyl-2-butyl-1H-cyclopenta[a]naphthalen-4-yl)hydrazine (compound (4)) was carried out as previously described (See Shukla et al., *J Med Chem* 53, 4450-4465 (2010). MS (APCI) calculated for $C_{21}H_{23}N_5$ m/z 345.20, found 345.5 (M+H)$^+$.

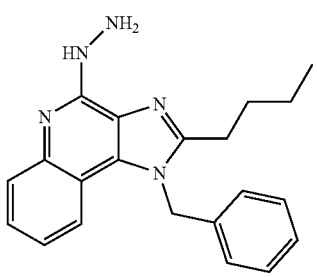
(4)

Modulating the bond stability between the TLR-7/8a and linker provides a means of controlling the release of the active TLR-7/8a from the inactive prodrug form of the molecule. FIGS. 3B and C illustrate two different types of linker groups. A hydrolytically stable hydrazide bond was used for attachment of either PEG linkers with terminal thiols, azides or amines, or an azido-pentanoyl linker was used (FIG. 3B). A second linker approach was to use tetrapeptide sequences that are recognized by proteases found in living systems (FIG. 3C).

By changing the sequence of the tetrapeptide it is possible to promote degradation by different classes of proteolytic enzymes. This study focused on evaluating how different sequences and either L or D-amino acid-based tetrapeptides predicted to be recognized by endosomally-localized cathepsin proteases influence the rate of release, and therefore, delay of onset of immune activity. The tetrapeptide sequences were produced based on previous findings regarding the substrate recognition by endosomal cathepsins.

Specific examples of conjugatable prodrug TLR-7/8a are described below.

Compound (5) is a conjugatable prodrug TLR-7/8a including compound (4) conjugated via the aryl-hydrazine to a hydrolytically stable linker including a terminal azide for conjugation to a polymer scaffold.

(5)

Synthesis of compound (5). To 2 mL of ethyl acetate was added 50 mg (0.15 mmol, 1 eq) of (4), 25 mg (0.15 mmol, 1 eq) of CDMT and 23 mg (0.16 mmol, 1.1 eq) of Azidopentanoic acid, followed by the drop wise addition of 19 μl (0.17 mmol, 1.2 eq) of NMM, while stirring vigorously. After 16 hours at room temperature, the reaction mixture was filtered and then washed 3×50 mL with 1 M HCl. The organic phase was dried with $Na_2SO_4$ and then evaporated to dryness. The resulting solid was purified by recrystallization from 4:1 Hexanes/ethyl acetate. A spectroscopically pure (>95% at 254 nm) white solid was obtained. MS (APCI) calculated for $C_{26}H_{30}N_8O$ m/z 470.3, found 471.3 $(M+H)^+$.

Compound (6) is a conjugatable prodrug TLR-7/8a including compound (4) conjugated via the aryl-amine to an enzyme degradable tetrapeptide linker including a terminal azide functional moiety for conjugation to a polymer scaffold. Compound (6) includes a KPLR (SEQ ID NO: 2)tetrapeptide of L-amino acids (6)

Synthesis of compound (6). To 2 mL of ethyl acetate was added 19 mg (0.055 mmol, 1.1 eq) of (4), 9 mg (0.061 mmol, 1 eq) of CDMT and 50 mg (0.051 mmol, 1 eq) of an azide-terminated L-amino acid-based tetrapeptide with protected side groups (X-KPLR(SEQ ID NO: 2)-COOH, where x=azidopentanoic acid) and a free acid C-terminus, followed by the dropwise addition of 20 μl (0.17 mmol, 1.2 eq) NMM, while stirring vigorously. After 16 hours at room temperature, the reaction mixture was filtered and then washed 3×50 mL with 1 M HCl. The organic phase was dried with $Na_2SO_4$ and then evaporated to dryness. The resulting solid was treated with 1 mL of an 88:5:5:2 solution of TFA/TIPS/Phenol/$H_2O$ to remove the protecting groups on the side chains of the tetrapeptide. After 1 h, the reaction mixture was added to 50 mL of ethyl ether and the de-protected product (6) precipitated from solution. The resulting crude product was purified by reverse phase HPLC chromatography using a 20-55% acetonitrile/H2O (0.05% TFA) gradient over 15 minutes (column=Zorbax SBC18 9.4×150 mm). The resulting fractions were collected, frozen and lyophilized to obtain a spectroscopically pure (>95% at 254 nm) white solid. MS (APCI) calculated for $C_{49}H_{72}N_{16}O_5$ m/z 964.6, found 965.6 $(M+H)^+$.

Synthesis of compound (7). The same procedure was used as reported for compound (6), except D-amino acids were used for the tetrapeptide. MS (APCI) calculated for $C_{49}H_{72}N_{16}O_5$ m/z 964.6, found 965.6 $(M+H)^+$. Compound (7) is a conjugatable prodrug TLR-7/8a including compound (4) conjugated via the aryl-amine to an enzyme degradable tetrapeptide linker including a terminal azide functional group for conjugation to a polymer scaffold. Compound (7) includes a KPLR (SEQ ID NO: 2) tetrapeptide of D-amino acids.

Compound (8) is a conjugatable prodrug TLR-7/8a including compound (4) conjugated via the aryl-amine to an enzyme degradable tetrapeptide linker including a terminal azide functional group for conjugation to a polymer scaffold. Compound (8) includes a KLRP (SEQ ID NO: 3)tetrapeptide of L-amino acids.

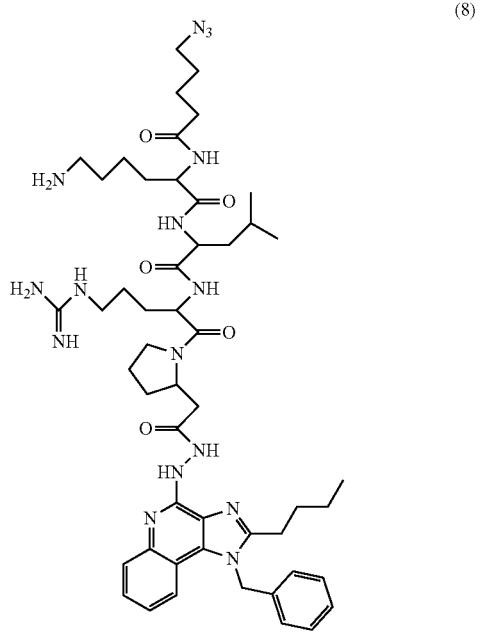 [SMILES: CCCCc1nc2c(NNC(=O)CC3CCCN3C(=O)C(CCCNC(=N)N)NC(=O)C(CC(C)C)NC(=O)C(CCCCN)NC(=O)CCCCN=[N+]=[N-])nc3ccccc3c2n1Cc1ccccc1]

(8)

Synthesis of compound (8). The same procedure was used as reported for compound (6), except the tetrapeptide sequence was X-KLRP (SEQ ID NO: 3). MS (APCI) calculated for $C_{49}H_{72}N_{16}O_5$ m/z 964.6, found 965.5 (M+H)$^+$.

Compound (9) is a conjugatable prodrug TLR-7/8a including compound (4) conjugated via the aryl-amine to an enzyme degradable tetrapeptide linker including a terminal azide functional group for conjugation to a polymer scaffold. Compound (9) includes a SLVR (SEQ ID NO: 4) tetrapeptide of L-amino acids.

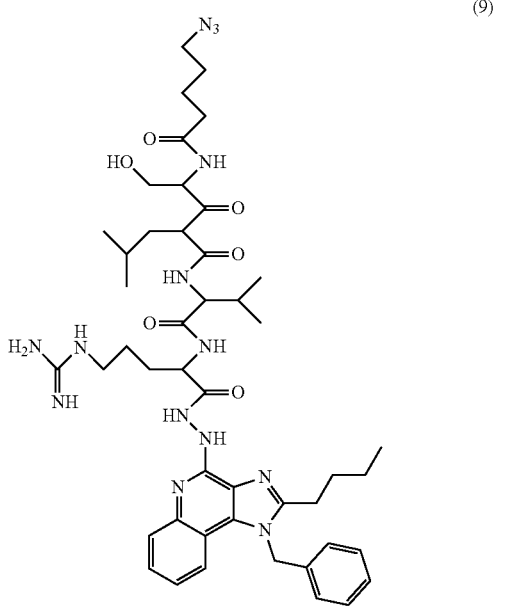 [SMILES: CCCCc1nc2c(NNC(=O)C(CCCNC(=N)N)NC(=O)C(NC(=O)C(CC(C)C)C(=O)C(CO)NC(=O)CCCCN=[N+]=[N-])C(C)C)nc3ccccc3c2n1Cc1ccccc1]

(9)

Synthesis of compound (9). The same procedure was used as reported for compound (6), except the tetrapeptide sequence was X-SLVR (SEQ ID NO: 4). MS (APCI) calculated for $C_{46}H_{67}N_{15}O_6$ m/z 925.5, found 926.6 (M+H)$^+$.

Synthesis of compound (10). The same procedure was used as reported for compound (9), except D-amino acids were used for the tetrapeptide. MS (APCI) calculated for $C_{49}H_{72}N_{16}O_5$ m/z 925.5, found 926.5 (M+H)$^+$. Compound (10) is a conjugatable prodrug TLR-7/8a including compound (4) conjugated via the aryl-amine to an enzyme degradable tetrapeptide linker including a terminal azide functional group for conjugation to a polymer scaffold. Compound (10) includes a SLVR (SEQ ID NO: 4) tetrapeptide of D-amino acids.

Compound (11) is a conjugatable prodrug TLR-7/8a including compound (4) conjugated via the aryl-amine to an enzyme degradable tetrapeptide linker including a terminal azide functional group for conjugation to a polymer scaffold. Compound (11) includes a SLRV (SEQ ID NO: 5) tetrapeptide of L-amino acids.

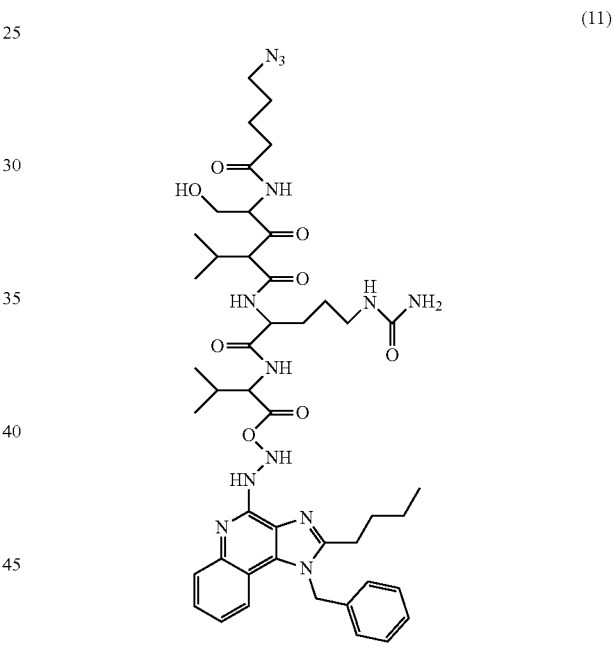

(11)

Synthesis of compound (11). The same procedure was used as reported for compound (9), except the tetrapeptide sequence was X-SLRV (SEQ ID NO: 5). MS (APCI) calculated for $C_{49}H_{72}N_{16}O_5$ m/z 925.5, found 926.6 (M+H)+.

Synthesis of Polybasic Conjugatable Prodrug TLR-7/8a

Conjugatable pro-drug TLR-7/8a can be prepared with multiple basic sites per molecule that allows the molecule to carry a high density of positive charge at physiologic pH. This high density of positive charge may reduce membrane permeability of the compound thereby slowing rate of clearance of the molecule from intracellular vesicles or lymphatic spaces.

Compound (12) was prepared as previously described (See Shukla et al., *J Med Chem* 53, 4450-4465 (2010)) and was used as a precursor to prepare the polybasic conjugatable pro-drug TLR-7/8 compound (13).

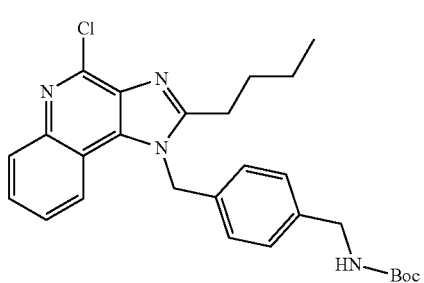

(12)

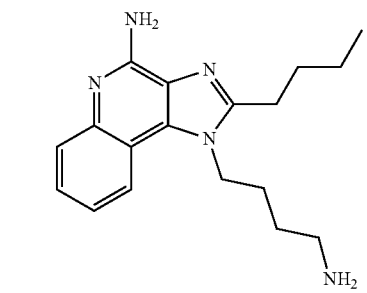

(15)

Compound (13) was prepared in a two-step reaction. To 800 μL of ethanol was added 200 mg (0.418 mmol, 1 eq) of (12), 122 μL (0.251 mmol, 6 eq) of hydrazine monohydrate followed by heating at 90 C for 5 hours. The reaction mixture was cooled to room temperature and then 400 μL of 15% aqueous ammonia was added to precipitate out the boc-protected intermediate as a yellow solid. The solid was washed with aqueous ammonia solution, followed by washing with DI water and then dried under vacuum. The solid was then added to 1 mL of 33% trifluoroacetic acid (TFA)/DCM solution to remove the boc protecting group. The TFA/DCM solution was removed by evaporation under argon to yield 186 mg of a yellow solid (94% yield). MS (APCI) calculated for $C_{22}H_{26}N_6$ m/z 374.2, found 374.5 $(M+H)^+$.

Compound (16) was prepared using the same reaction scheme as compound (1) except N—$N^1$,$N^5$-bis-boc-spermidine was used in place of 1-(N-Boc-aminomethyl)-4-(aminomethyl)benzene. MS (APCI) calculated for $C_{21}H_{32}N_6$ m/z 368.27, found 369.1 $(M+H)^+$.

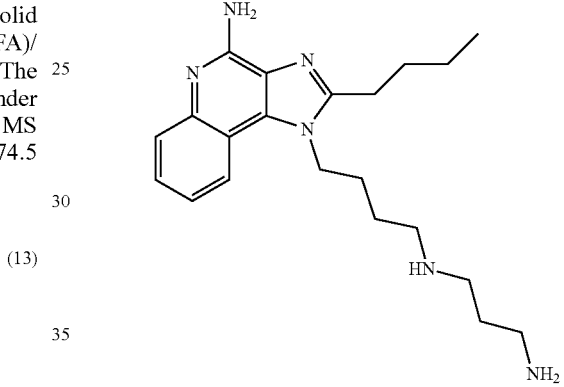

(16)

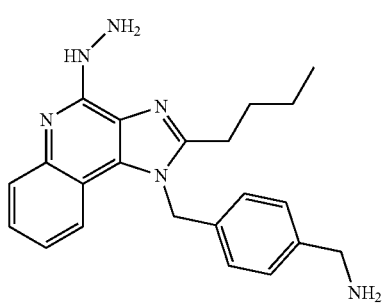

(13)

Compound (17) can be accessed from compound (1) through reaction with methyl triflate in hexafluoroisopropanol using the monomethylation process as described by Lebleu et al., *Chem. Commun.* 50, 1836-1838 (2014).

Compound (14) was prepared as previously described (See Shukla et al., *J Med Chem* 53, 4450-4465 (2010)). MS (APCI) calculated for $C_{22}H_{26}N_6$ m/z 374.2, found 374.5 $(M+H)^+$.

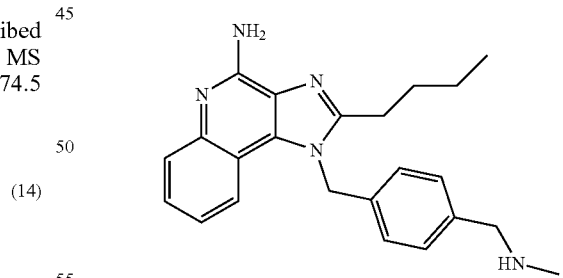

(17)

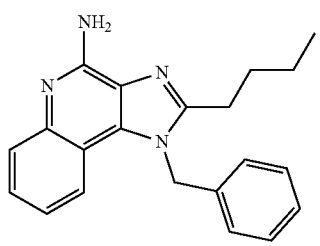

(14)

Compound (15) was prepared using the same reaction scheme as compound (1) except N-Boc-1,4-butanediamine was used in place of 1-(N-Boc-aminomethyl)-4-(aminomethyl)benzene. MS (APCI) calculated for $C_{22}H_{26}N_6$ m/z 311.2, found 312.2 (M+H)+.

Compounds (18) and (19) can be accessed through alkylation of (1) using a suitable alkyl halide in the presence of base. A non-limiting example includes 4-(Boc-amino)butyl bromide. A mixture of N alkylated products would be expected and can he separated by chromatography, followed by deprotection using 30% trifluoroacetic acid/DCM to yield compounds (18) and (19). The ratio of products can be controlled by choice of solvent, base and temperature, as previously described (see: Lebleu et al., *Chem. Commun.* 50, 1836-1838 (2014)). An alternative route to compounds (18) and (19) is to react compound (1) with a stuiable acid to form an amide intermediate that can be reduced with a suitable reducing agent, such as lithium aluminum hydride (LiAlH₄). A non-limiting example could be amide bond formation between the benzyle amine of (1) and the acid of N-boc amino butyric acid using standard coupling chemistry, such as using a carbodiimide, such as 1-Ethyl-3-(3-dimethylaminopropyl)carbodiimide. The resulting amide intermediate could then be reduced to yield the mono alkylated product. The amide coupling and reduction would be repeated to yield the tertiary amine product, followed be deprotection to yield compounds (18) and (19).

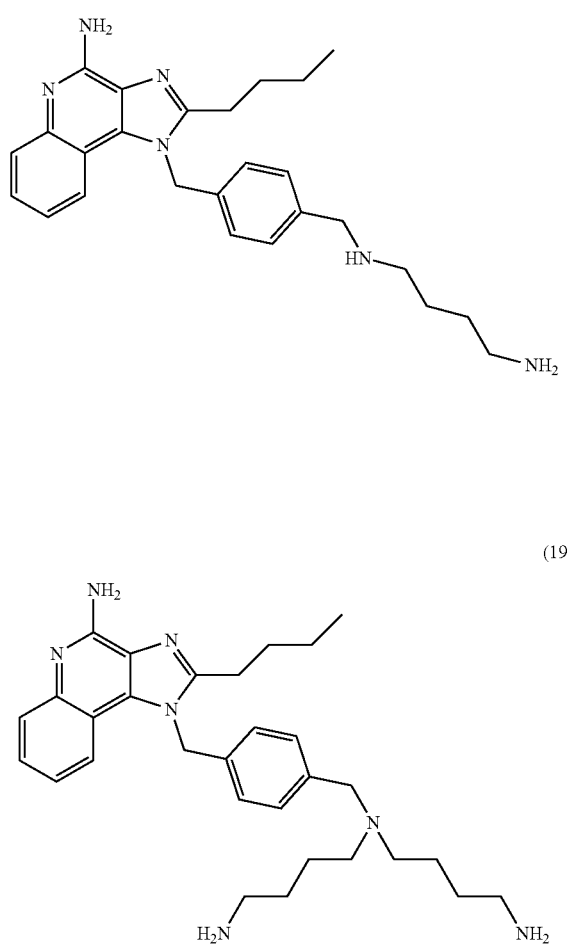

(18)

(19)

Compound (20) could be accessed through reaction of compound (1) with a suitable acrylamide through Michael Addition reaction, followed by boc deprotection. A non-limiting example of an acrylamide could be tert-butyl (4-acrylamidobutyl)carbamate, which can be prepared from a reaction of the acid chloride, acryloyl chloride, with tert-butyl (4-aminobutyl)carbamate in the presence of base. Low temperatures and a suitable radical acceptor, such as MEHQ should be used to avoid polymerization. The acrylamide could then be reacted with (1) to afford a boc protected intermediate. The boc protected intermediate can be deprotected in 30% TFA/DCM to yield compound (20), or the intermediate can be reduced with LiAlH₄ to reduce the amide and remove the boc groups, resulting in compound (28).

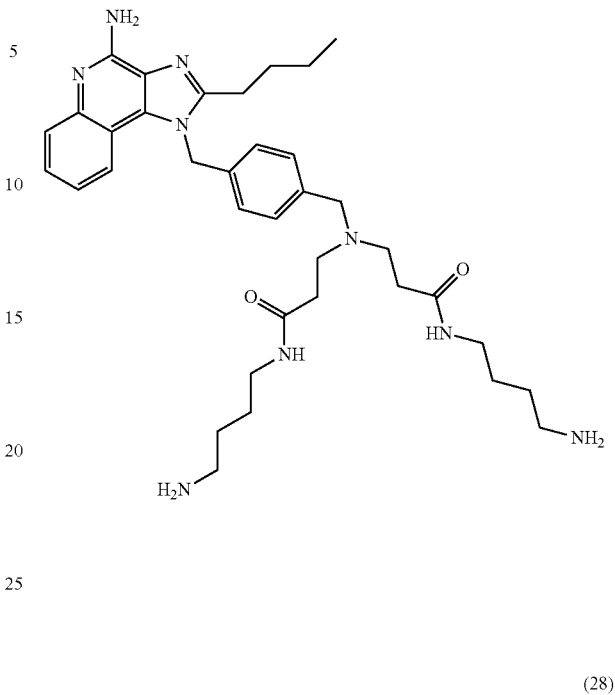

(20)

(28)

Compounds (21) can be prepared through a similar process as described for compound (17) except by starting from compound (12). In short, compound (12) can first be deprotected using 30% TFA-DCM to yield to yield compound (29).

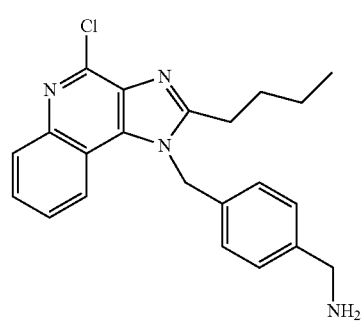

(29)

Compound (29) can then be reacted with excess (>10 equivalents) of tertbutyl carbazate at high temperatures (>90 C) in a suitable polar solvent to yield compound (30).

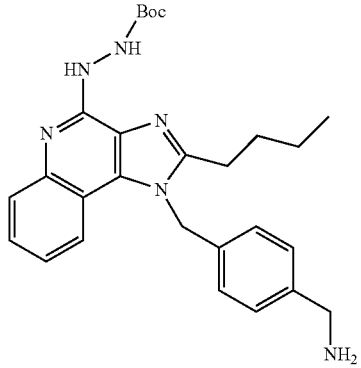
(30)

Compound (21) can then be prepared from compound (30) using a similar process as described for compound (17).

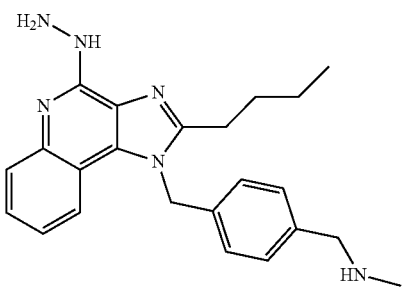
(21)

Compound (22) can then be prepared from compound (30) using a similar process as described for compound (18).

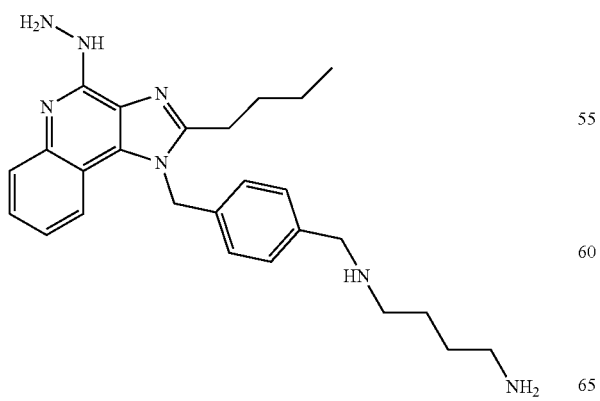
(22)

Compound (23) can then be prepared from compound (30) using a similar process as described for compound (19).

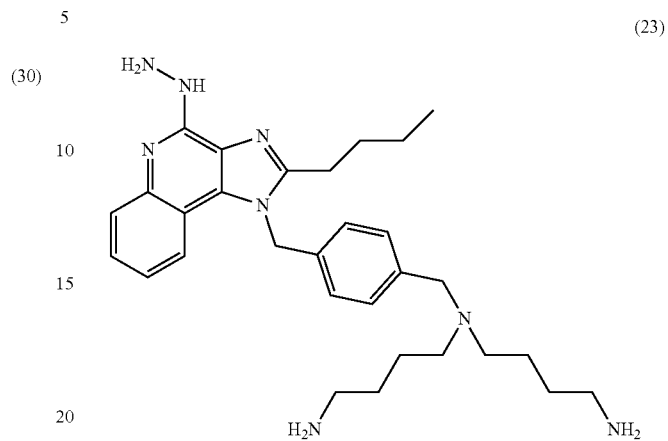
(23)

Compound (24) can then be prepared from compound (30) using a similar process as described for compound (20).

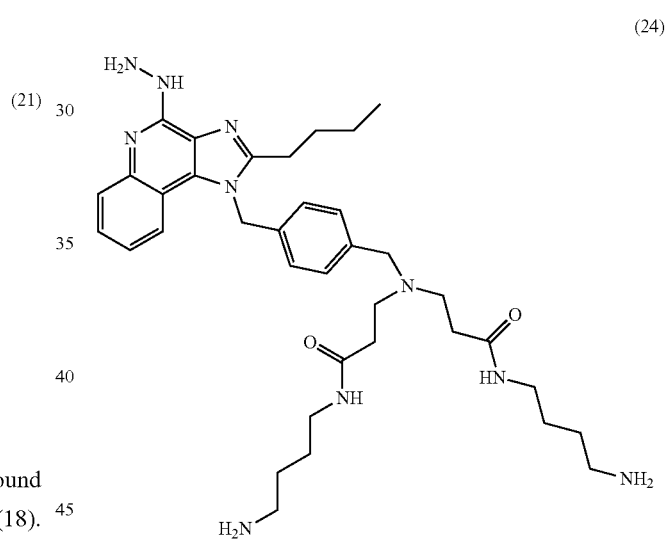
(24)

Compound (25) can be accessed from compound (15) through reaction with methyl triflate in hexafluoroisopropanol using the monomethylation process as described by Lebleu et al., *Chem. Commun.* 50, 1836-1838 (2014)

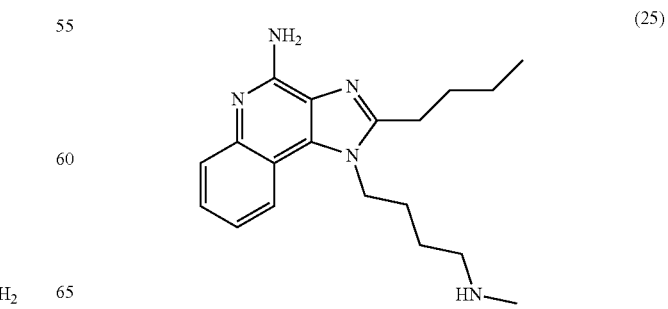
(25)

Compound (26) can then be prepared from compound (15) using a similar process as described for compound (19).

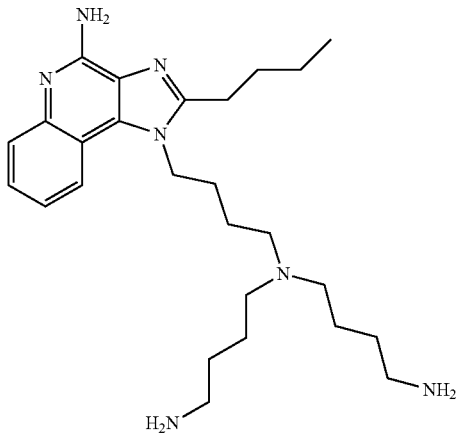

(26)

Compound (27) can then be prepared from compound (15) using a similar process as described for compound (20).

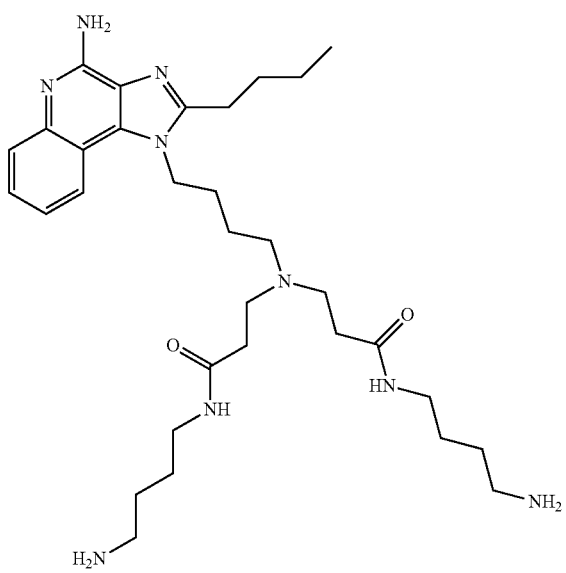

(27)

Figure 4A:
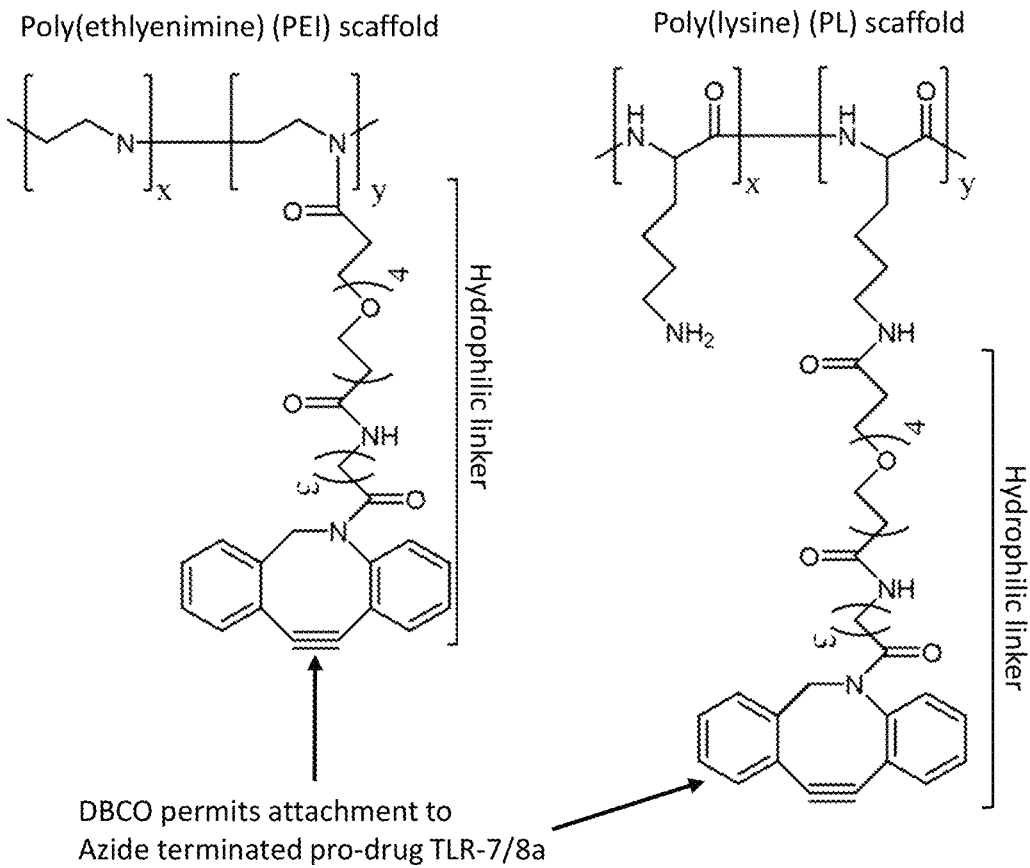
FIGS. 4A and 4B show exemplary poly(ethylenimine) (PEI)-, poly(lysine) (PL)-, and poly(glutamate)-based polymer scaffolds that include a hydrophilic linker with an azide-reactive group for conjugation with terminal-azide labeled adjuvant prodrugs. (4A) PEI- and PL-based polymer scaffolds with an azide-reactive dibenzylcyclooctyne (DBCO) group. (4B) PL- and PG-based polymer scaffolds with azide-reactive terminal alkynes. The cationic PEI and PL polymer scaffolds can form a complex with nucleic acid molecules via electrostatic interaction. The anionic PG scaffold can be complexed with a cation that interacts with nucleic acid. The PEI scaffold is positively charged at physiologic pH and has been shown to be an effective delivery system for nucleic acid delivery to a subject. The PL scaffold is positively charged at physiological pH and can be used for nucleic acid delivery. Unlike the PEI scaffold, the PL scaffold is biodegradable. The brackets represent repeating units of each monomer, with the subscripts, x and y, representing the percentage composition (mol %) of each monomer.
Figure 4B:
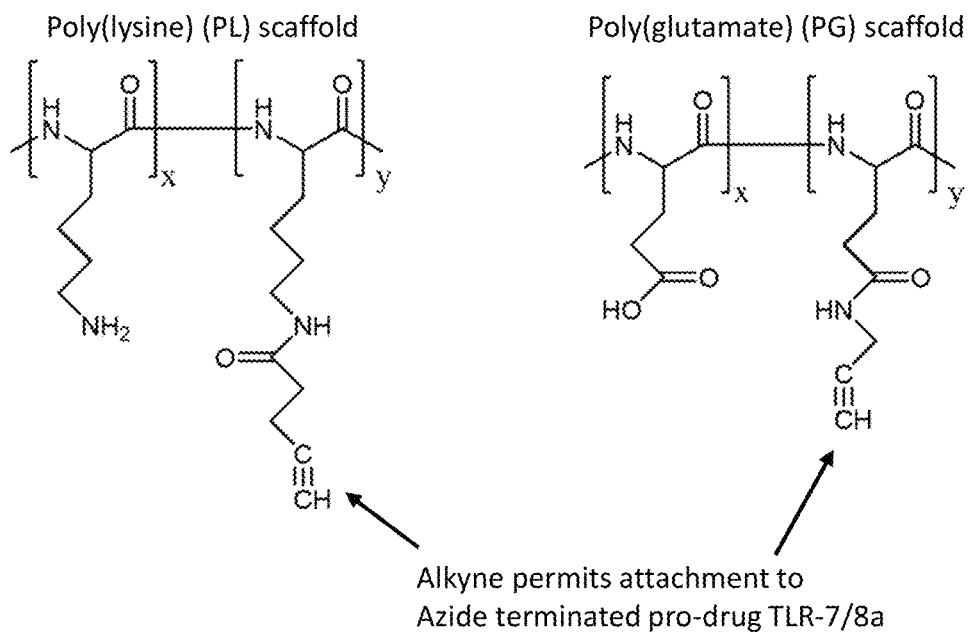

Synthesis of azide-reactive PEI and PL-based polymeric gene delivery systems. PEI and PL-based gene delivery systems were chemically modified with azide-reactive, dibenzylcyclooctyne (DBCO) chemical cross-linkers to permit attachment of active and prodrug TLR-7/8a (FIG. 4A). The DBCO group reacts with azide groups at room temperature and does not require addition of a catalyst, unlike acetylene groups that require Cu(I) to catalyze the cycloaddition reaction (FIG. 4B), thus permitting a facile strategy for attaching azide-bearing active and prodrug TLR-7/8a to polymer backbones.

Conjugation of active TLR-7/8a to PEI-based polymers. Synthesis of PEI-based carriers of active TLR-7/8a was carried out in a simple 2-step reaction in methanol.

Figure 5:
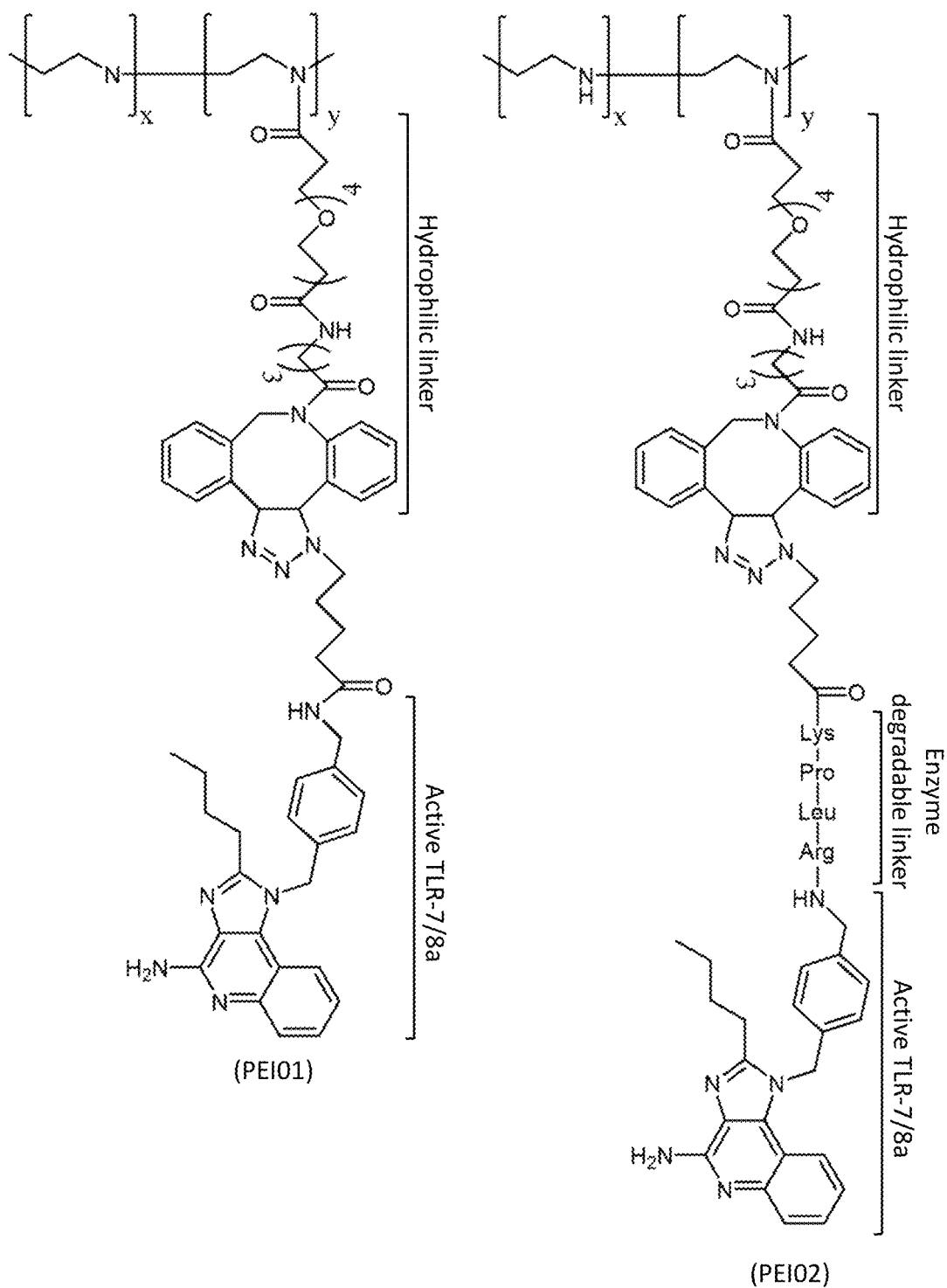
FIG. 5 shows structures of PEI-based polymers linked to compound (2) (left, with a hydrolytically stable amide bond) or compound (3) (right, with an enzyme degradable tetrapeptide linker) using a DBCO-based chemical cross-linker. The brackets represent repeating units of each monomer, with the subscripts, x and y, representing the percentage composition (mol %) of each monomer.

Example reactions to generate PEI-based polymer (PEI01) (including to compound (2), with a hydrolytically stable amide bond) and polymer (PEI02) (including compound (3), with an enzyme degradable tetrapeptide linker) are provided below. The polymer structure is shown in FIG. 5. The (PEI01) and (PEI02) polymers include a DBCO-based chemical cross-linker.

(PEI01) To 500 µL of methanol was added 13.2 mg (308 µmoles, 1 EQ) of 25 kDA PEI (free base) followed by addition of 5.0 mg (8 µmoles, 0.025 EQ) NHS-PEG4-DBCO. After 1 hour, 4.85 mg (10.4 µmoles, 0.033 EQ) of compound (2) was added and the reaction proceeded at room temperature for 18 hours. The polymer-TLR-7/8a conjugate was then purified by dialysis in methanol and characterized for TLR-7/8a content and polymer molecular weight.

(PEI02) To 500 µL of methanol was added 13.2 mg (308 µmoles, 1 EQ) of 25 kDA PEI (free base) followed by addition of 5.0 mg (8 µmoles, 0.025 EQ) NHS-PEG4-DBCO. The reaction mixture appeared cloudy but then became translucent as the cross-linker reacted with the soluble polymer. After 1 hour, 10.2 mg (10.4 µmoles, 0.033 EQ) of compound (3) was added and the reaction proceeded at room temperature for 18 hours. The polymer-TLR-7/8a conjugate was purified by dialysis in methanol and characterized for TLR-7/8a content and polymer molecular weight.

TABLE 1

| PEI-based carriers of active TLR-7/8a. Note that the ligand density is the percentage of monomer units of the polymer that have TLR-7/8a attached. | | | |
|---|---|---|---|
| Polymer | Carrier | Ligand | TLR-7/8a density actual (theoretical) |
| PEI01 | PEI | (2) | 2.14 (2.5) mol % |
| PEI02 | PEI | (3) | 2.10 (2.5) mol % |

Conjugation of active TLR-7/8a to PL-based polymers. Synthesis of PL-based carriers of active TLR-7/8a was carried out in a simple 2-step reaction in aqueous buffer.

Figure 6:
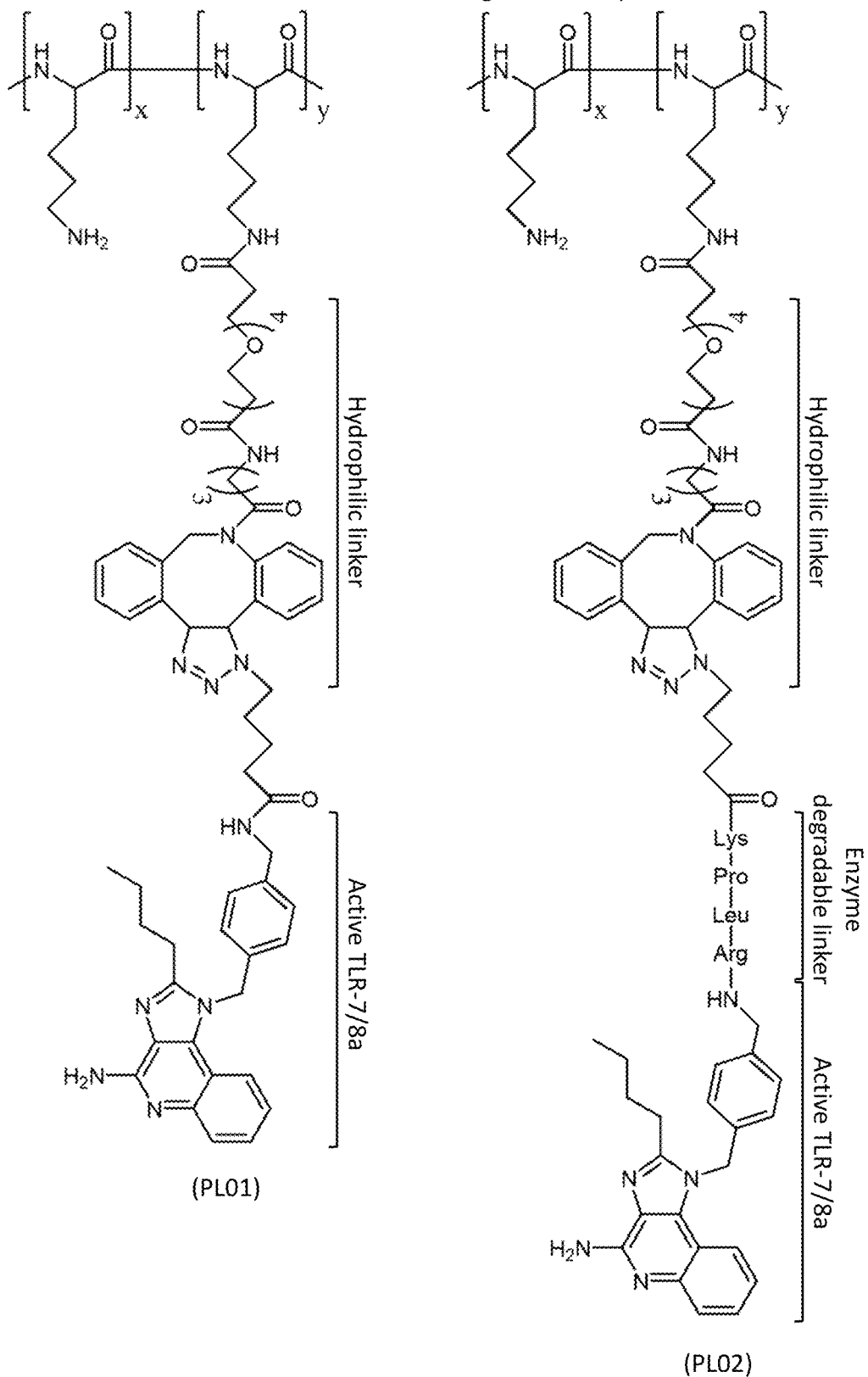
FIG. 6 shows structures of PL-based polymers linked to compound (2) (left, with a hydrolytically stable amide bond) or compound (3) (right, with an enzyme degradable tetrapeptide linker) using a DBCO-based chemical cross-linker. The brackets represent repeating units of each monomer, with the subscripts, x and y, representing the percentage composition (mol %) of each monomer.

Example reactions to generate PL-based polymer (PL01) (including to compound (2), with a hydrolytically stable amide bond) and polymer (PL03) (including compound (3), with an enzyme degradable tetrapeptide linker) are provided below. The polymer structure is shown in FIG. 6. The (PL01) and (PL02) polymers include a DBCO-based chemical cross-linker.

(PL01) To 1 mL of 0.1 Molar HEPES (pH 8.0) was added 10 mg (48 µmoles, 1 EQ) of Poly(L-Lysine).HBr, followed by addition of 1.55 mg (2.4 µmoles, 0.05 EQ) NHS-PEG4-DBCO. The reaction mixture appeared cloudy but then became translucent as the cross-linker reacted with the soluble polymer. After 1 hour, 1.27 mg (2.6 µmoles, 0.055 EQ) of compound (2) was added and the reaction proceeded at room temperature for 18 hours. The polymer-TLR-7/8a conjugate was purified by dialysis in methanol and characterized for TLR-7/8a content and polymer molecular weight. The same procedure was carried out for (PL02) except 4.8 and 5.2 µmoles of NHS-PEG4-DBCO and compound (2), respectively, where used in the reaction to produce a polymer with a higher density of the active TLR-7/8a.

(PL03) To 1 mL of 0.1 Molar HEPES (pH 8.0) was added 10 mg (48 µmoles, 1 EQ) of Poly(L-Lysine).HBr, followed by addition of 1.24 mg (2 µmoles, 0.04 EQ) NHS-PEG4-DBCO. The reaction mixture appeared cloudy but then became translucent as the cross-linker reacted with the soluble polymer. After 1 hour, 2 mg (2 µmoles, 0.04 EQ) of compound (3) was added and the reaction proceeded at room temperature for 18 hours. The polymer-TLR-7/8a conjugate was purified by dialysis in methanol and characterized for TLR-7/8a content and polymer molecular weight.

TABLE 2

PL-based carriers of active TLR-7/8a. Note that the ligand density is the percentage of monomer units of the polymer that have TLR-7/8a attached.

| Polymer | Carrier | Ligand | TLR-7/8a density actual (theoretical) |
|---|---|---|---|
| PL01 | PL | (2) | 4.73 (5.0) mol % |
| PL02 | PL | (2) | 10.83 (10.0) mol % |
| PL03 | PL | (3) | 3.55 (4.0) mol % |

Figure 7:
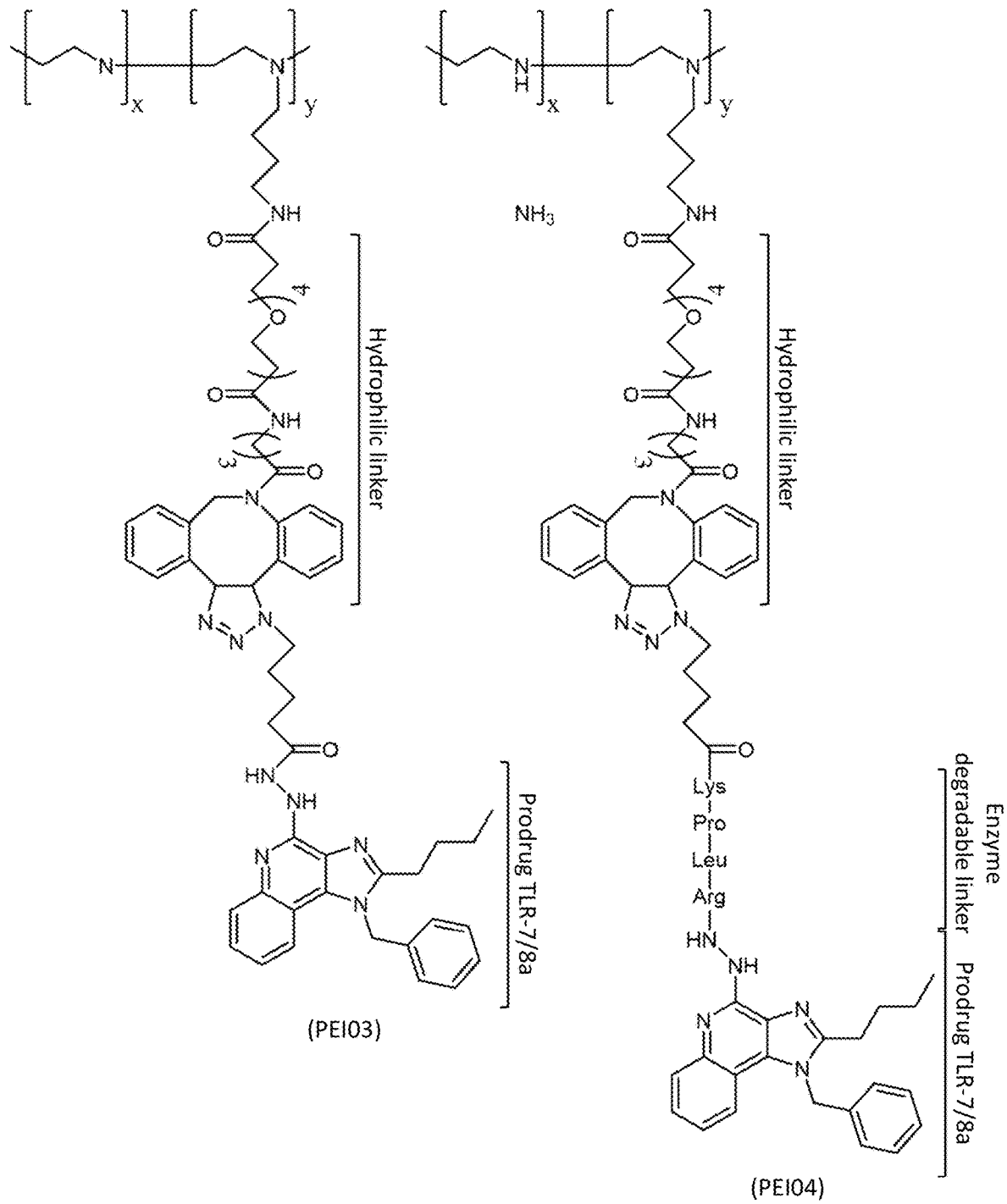
FIG. 7 shows structures of PEI-based polymers linked to compound (5) (left, with a hydrolytically stable amide bond) or compound (6) (right, with an enzyme degradable tetrapeptide linker) using a DBCO-based chemical cross-linker. The TLR-7/8a is not active until the hydrazide bond is cleaved. The brackets represent repeating units of each monomer, with the subscripts, x and y, representing the percentage composition (mol %) of each monomer.

Conjugation of prodrug TLR-7/8a to PEI-based polymers. PEI-based polymers were linked to compounds (5-9) using a DBCO-based chemical cross-linker to generate polymers including prodrug TLR-7/8a. Synthesis of the PEI-based carriers of prodrug TLR-7/8 was carried out in a simple 2-step reaction in methanol as described above for polymers PEI01 and PEI02. The polymer structures for (PEI03) and (PEI04) are shown in FIG. 7.

TABLE 3

PEI-based carriers of prodrug TLR-7/8a. Note that the ligand density is the percentage of monomer units of the polymer that have TLR-7/8a attached.

| Polymer | Carrier | Ligand | TLR-7/8a density - Actual (theoretical) |
|---|---|---|---|
| PEI03 | PEI | (5) | 3.92 (4.0) mol % |
| PEI04 | PEI | (6) | 1.77 (2.5) mol % |
| PEI05 | PEI | (7) | 1.73 (2.5) mol % |
| PEI06 | PEI | (8) | 1.52 (2.5) mol % |
| PEI07 | PEI | (9) | 2.43 (2.5) mol % |

Figure 8:
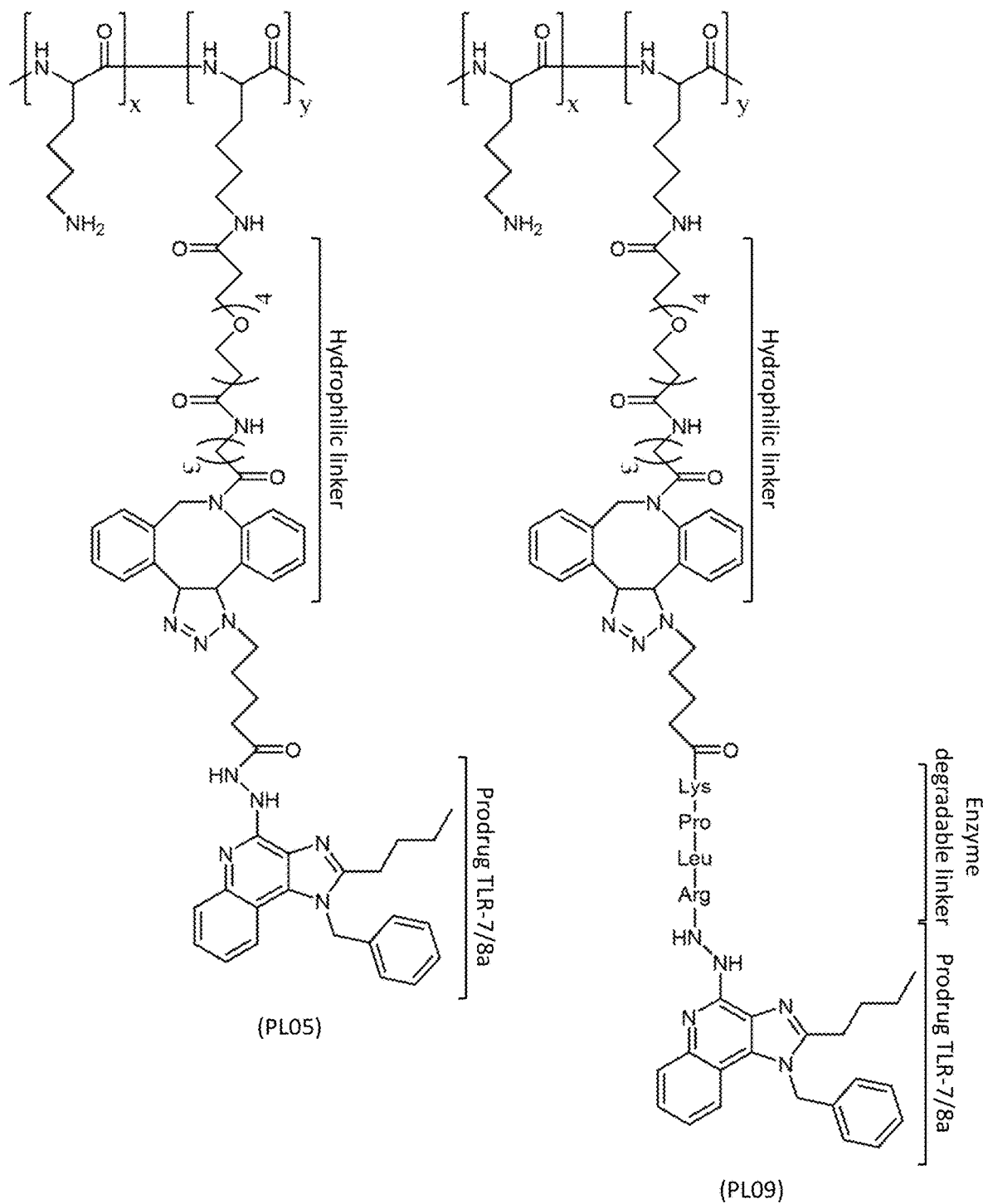
FIG. 8 shows structures of PL-based polymers linked to compound (5) (left, with a hydrolytically stable amide bond) or compound (6) (right, with an enzyme degradable tetrapeptide linker) using a DBCO-based chemical cross-linker. The TLR-7/8a is not active until the hydrazide bond is cleaved. The brackets represent repeating units of each monomer, with the subscripts, x and y, representing the percentage composition (mol %) of each monomer.
Figure 9:
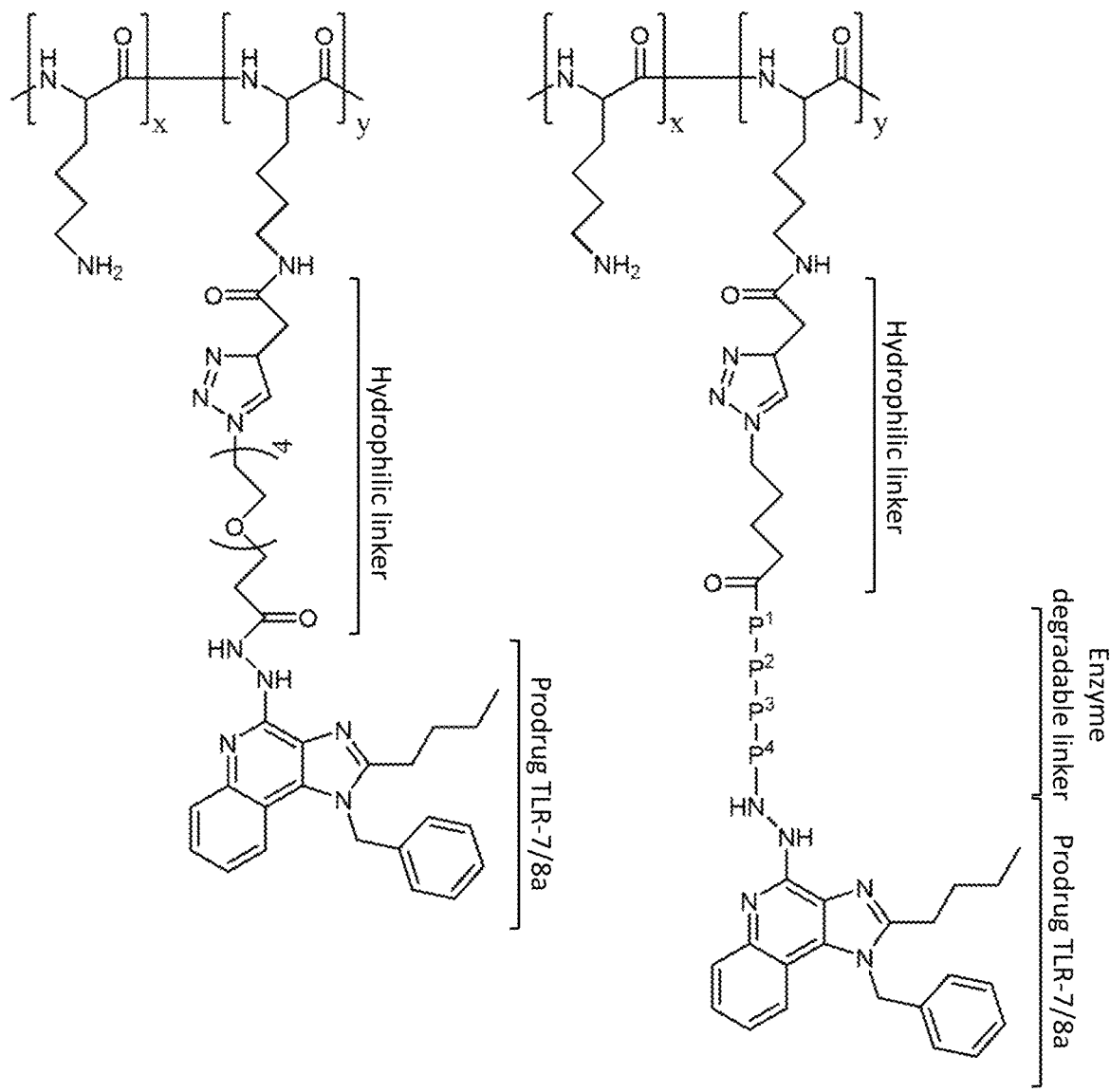
FIG. 9 shows structures of PL-based polymers linked to compound (5) with a terminal alkyne-based linker including a hydrolytically stable amide bond (left) or an enzyme degradable tetrapeptide linker (right). The TLR-7/8a is not active until the hydrazide bond is cleaved.

Conjugation of prodrug TLR-7/8a to PL-based polymers. PL-based polymers were linked to compounds (5), (6), and (9) using a DBCO-based chemical cross-linker to generate polymers including prodrug TLR-7/8a. Synthesis of the PL-based carriers of prodrug TLR-7/8 was carried out in a simple 2-step reaction in HEPES buffer as described above for polymers PL01 and PL02. The polymer structures for (PL03) and (PL04) are shown in FIG. 8.

TABLE 4

PL-based carriers of prodrug TLR-7/8a. Note that the ligand density is the percentage of monomer units of the polymer that have TLR-7/8a attached.

| Polymer | Carrier | Ligand | TLR-7/8a density Actual (theoretical) |
|---|---|---|---|
| PL04 | PL | (5) | 4.17 (5) mol % |
| PL05 | PL | (5) | 11.3 (10) mol % |
| PL06 | PL | (5) | 27.5 (20) mol % |
| PL07 | PL | (5) | 44.8 (40) mol % |
| PL08 | PL | (6) | 4.96 (5) mol % |
| PL09 | PL | (6) | 9.97 (10) mol % |
| PL10 | PL | (9) | 3.09 (5) mol % |
| PL11 | PL | (9) | 9.33 (10) mol % |

Formation of polymer nanoparticle. Expression vector delivery systems (i.e., PEI and PL-based cationic polymers) linked to either active or pro-drug TLR-7/8a were complexed with DNA based plasmids through electrostatic interactions to generate polymer nanoparticles, referred to as Polyplexes. An N:P ratio (where N=moles of base and P=moles of phosphate) of 10:1 was used to ensure that the DNA was fully complexed with the expression vector delivery system and to allow for a net positive charge that is known by those skilled in the art to promote cellular uptake by interacting with negatively charged cell surfaces. The buffer used for the preparation of the polymer nanoparticles was PBS. An example of the formulation is provided: to generate polymer nanoparticles comprised of PEI03 and a CpG-free DNA-based Luciferase reporter plasmid (5158 BP in length), 55 µL of the DNA plasmid at 1 mg/mL (55 µg mass DNA; ~0.16 µmoles P) in PBS was added to a 73 µL solution of PBS containing 56 µg of PEI03 and 43 µg of PEI alone (1.6 µmoles N) while stirring vigorously. The solution became turbid upon mixing, indicating nanoparticle formation as confirmed by dynamic light scattering. Both PEI03 and PEI were used as a co-formulation to control for the dose of the prodrug TLR-7/8a as well as the charge ratio between the base (PEI) and the phosphate on the nucleic acid. The formulation delivered at 60 µL per site of injection contains 25 µg of the DNA plasmid and 10 nmole of the prodrug TLR-7/8a.

Figure 10A:
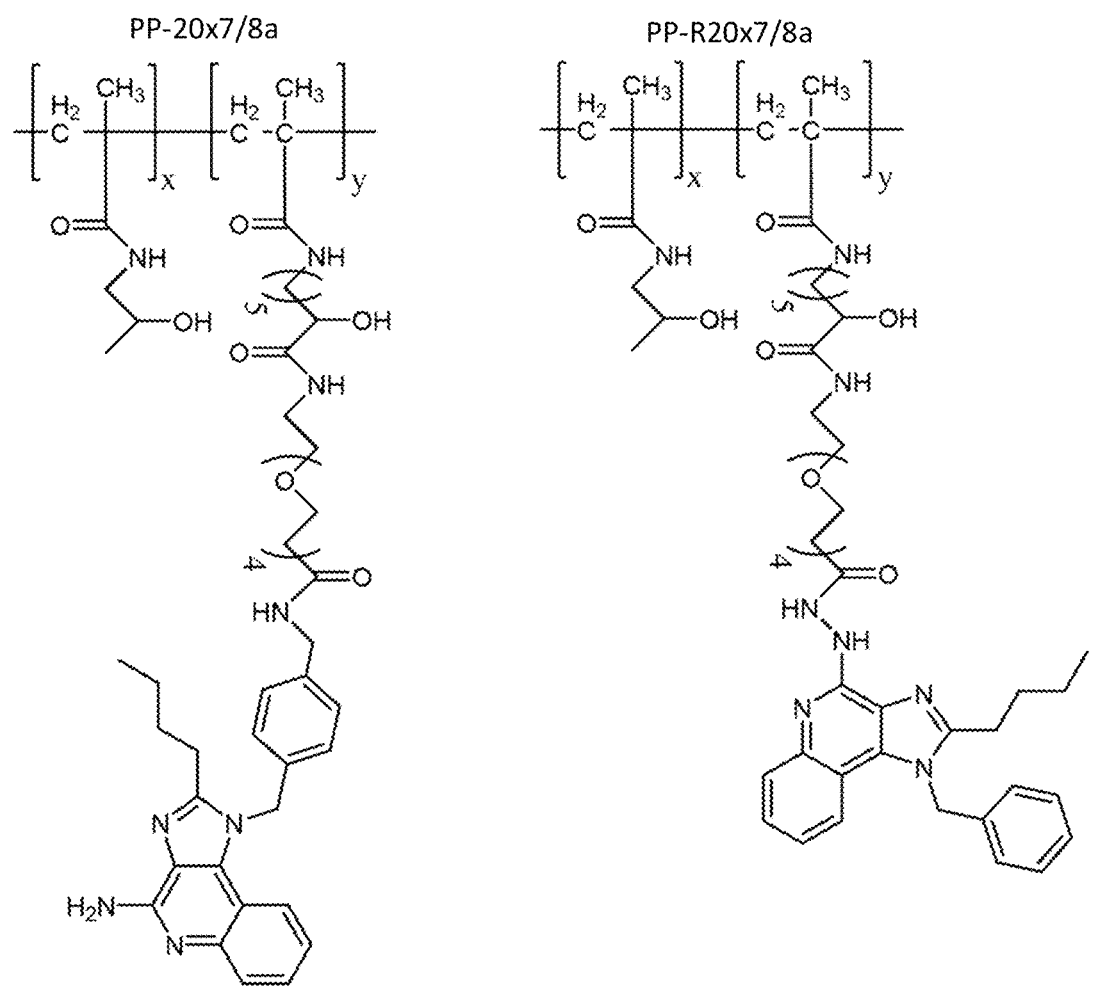

Delayed induction of an immune response using polymer nanoparticles without plasmid. Polymer nanoparticles comprised of polymers linked to TLR-7/8a were prepared with the TLR-7/8a attached to the polymer carrier with either the $C_4$-amine exposed (PP-20×7/8a) or blocked (PP-R20×7/8a). The linkage of the TLR-7/8a to the polymer in PP-R20×7/8a did not include a cathepsin-cleavable linker. The polymer nanoparticles including the polymer/TLR-7/8a conjugates were administered subcutaneously into the hind footpads of $C_{57}BL/6$ mice without co-formulation with DNA plasmid and lymph nodes were isolated at serial time points thereafter and cultured overnight. Supernatant from the ex vivo lymph node cell suspensions (n=4) were evaluated for IL-12 and IP-10 by ELISA. As shown in FIG. 10, blocking the $C_4$-amine delayed onset and lowered the magnitude of cytokine production.

Figure 11:
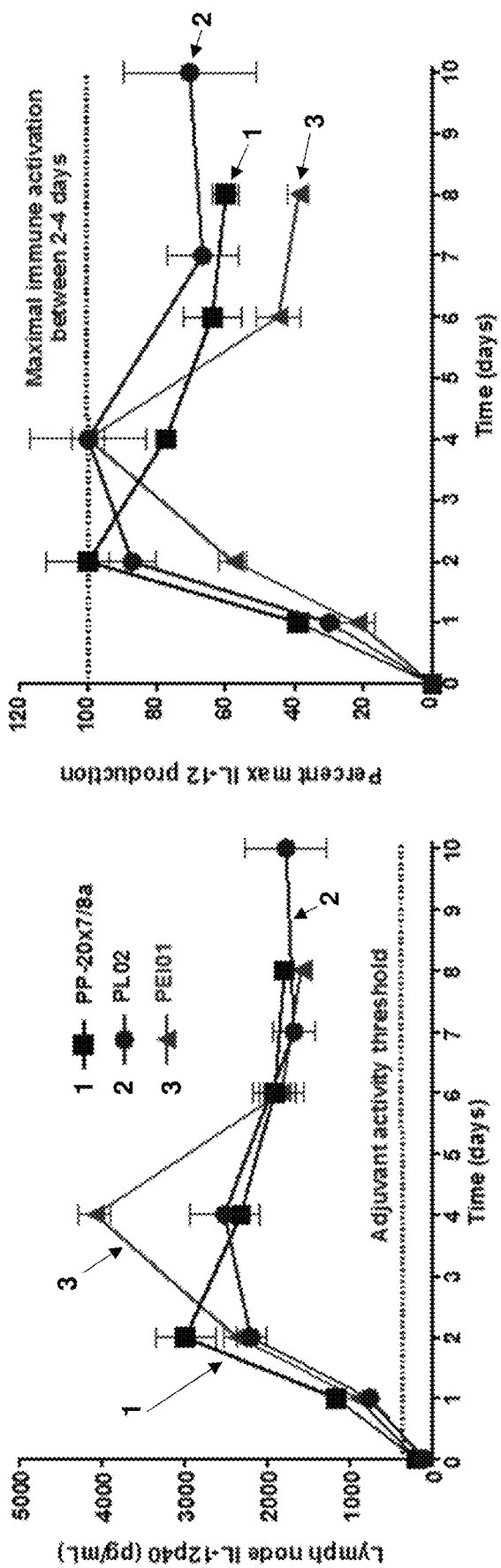
FIG. 11 shows a set graphs illustrating that three different compositions of polymers linked to the active form of an adjuvant lead to immune activation less than one day after administration in the host. Polymer nanoparticles comprised of HPMA (PP-20×7/8a), PL (PL02) and PEI (PEI01) linked to TLR-7/8a were prepared with the TLR-7/8a attached to the polymer carrier with the C4-amine exposed (PP-20×7/8a) and were co-formulated with a DNA plasmid. The linkage of the TLR-7/8a to the polymers did not include a cathepsin-cleavable linker. The polymer nanoparticles including the cationic polymer/TLR-7/8a conjugates (PLO2 and PEI01) were linked (N:P 10:1) to the DNA plasmid, whereas the hydrophilic HPMA polymer (PP-20×7/8a) was simply admixed with the plasmid. The polymer nanoparticle formulations with the DNA plasmid were administered subcutaneously into the hind footpads of C57BL/6 mice and lymph nodes were isolated at serial time points thereafter and cultured overnight. Supernatant from the ex vivo lymph node cell suspensions (n=4) were evaluated for IL-12 by ELISA.

Induction of an immune responses using polymer nanoparticles with active TLR-7/8a linked or unlinked with DNA plasmid. Polymer nanoparticles comprised of HPMA (PP-20×7/8a), PL (PL02) and PEI (PEI01) linked to TLR-7/8a were prepared with the TLR-7/8a attached to the polymer carrier with the $C_4$-amine exposed (PP-20×7/8a) and were co-formulated with a DNA plasmid (FIG. 11 top). The linkage of the TLR-7/8a to the polymers did not include a cathepsin-cleavable linker (FIG. 11 top). The polymer nanoparticles including the cationic polymer/TLR-7/8a conjugates (PL02 and PEI01) were linked (N:P 10:1) to the DNA plasmid, whereas the hydrophilic HPMA polymer (PP-20×7/8a) was simply admixed with the plasmid. The polymer nanoparticle formulations with the DNA plasmid were administered subcutaneously into the hind footpads of $C_{57}BL/6$ mice and lymph nodes were isolated at serial time points thereafter and cultured overnight. Supernatant from the ex vivo lymph node cell suspensions (n=4) were evaluated for IL-12 by ELISA. As shown in FIG. 11, the polymers linked to the TLR-7/8a with the $C_4$-amine exposed induce high magnitude immune responses by day 1, indicating rapid onset of immune activation.

Figure 12:
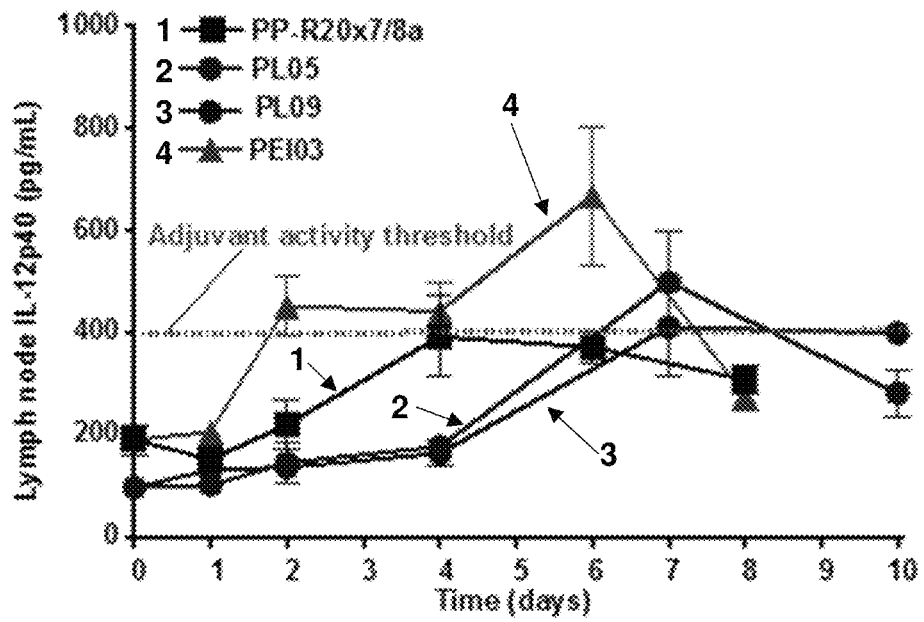
FIG. 12 shows a set graphs illustrating that various polymer compositions linked to a prodrug TLR-7/8a can delay the onset of immune activation in vivo when admixed or linked with a DNA plasmid. Polymer nanoparticles comprised of HPMA (PP-R20×7/8a), PL (PLO5 and PL09) and PEI (PEI03) based polymers were linked to the TLR-7/8a so as to block the C4-amine that is critical to activity. The poly(basic) PL and PEI-based polymers were co-formulated with a DNA plasmid at 10:1, whereas the HPMA-based polymer, PP-R20×7/8a was simply admixed with the DNA plasmid. The linkage of the TLR-7/8a to the polymers did not include a cathepsin-cleavable linker for PP-R20×7/8a, PLO5 and PEI03 but PLO9 did include a tetrapeptide, enzyme degradable linker between the polymer and pro-drug. The polymer nanoparticles including the polymer/TLR-7/8a conjugates linked (N:P 10:1) or unlinked (PP-20× 7/8a) with the DNA plasmid were administered subcutaneously into the hind footpads of C57BL/6 mice and lymph nodes were isolated at serial time points thereafter and cultured overnight. Supernatant from the ex vivo lymph node cell suspensions (n=4) were evaluated for IL-12 by ELISA.
Figure 12:
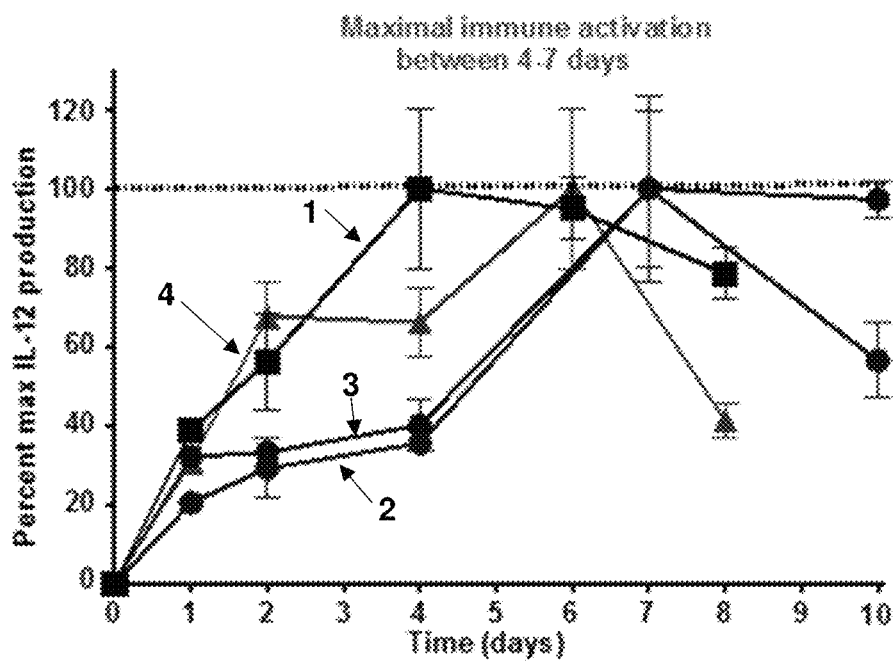

Delayed induction of immune responses using polymer nanoparticles with prodrug TLR-7/8a linked or unlinked with DNA plasmid. Polymer nanoparticles comprised of HPMA (PP-R20×7/8a), PL (PL05 and PL09) and PEI (PEI03) based polymers were linked to the TLR-7/8a so as to block the $C_4$-amine that is critical to activity (FIG. 12A). The poly(basic) PL and PEI-based polymers were co-formulated with a DNA plasmid at 10:1 N:P, whereas the HPMA-based polymer, PP-R20×7/8a was simply admixed with the DNA plasmid. The linkage of the TLR-7/8a to the polymers did not include a cathepsin-cleavable linker for PP-R20×7/8a, PL05 and PEI03 but PL09 did include a tetrapeptide, enzyme degradable linker between the polymer and pro-drug (FIG. 12A). The polymer nanoparticles including the polymer/TLR-7/8a conjugates linked (N:P 10:1) or unlinked (PP-20×7/8a) with the DNA plasmid were administered subcutaneously into the hind footpads of $C_{57}BL/6$ mice and lymph nodes were isolated at serial time points thereafter and cultured overnight. Supernatant from the ex vivo lymph node cell suspensions (n=4) were evaluated for IL-12 by ELISA. As shown in FIG. 12, the polymers linked to the pro-drug TLR-7/8a did not induce immune activation (>2×S.D of responses by polymer alone, ~400 pg/mL IL-12) until between 2 and 7 days after administration.

Measuring Gene Expression In Vivo

Figure 13:
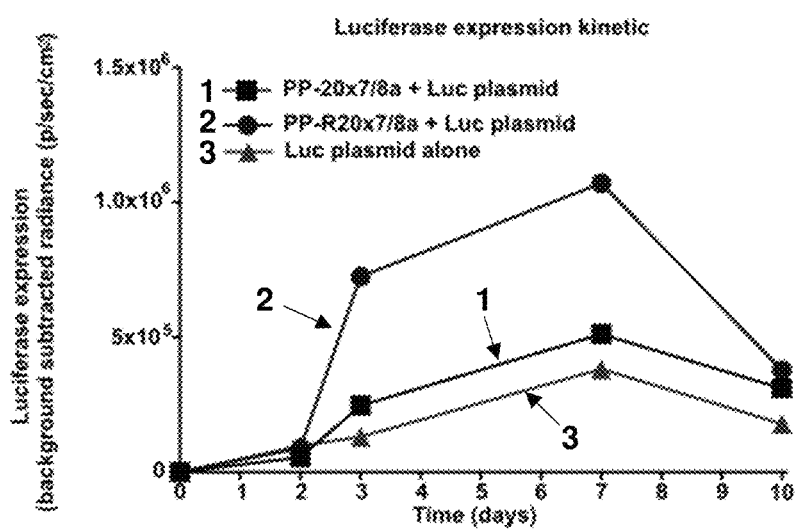
FIG. 13 shows that polymer nanoparticles comprised of HPMA linked to either active adjuvant (PP-20×7/8a) or prodrug adjuvant (PP-R20×7/8a) and admixed with DNA plasmid administered intramuscularly into the thigh of BALB/c mice can induced gene expression. Luciferase expression was monitored at serial time points and is shown in the top of FIG. 13. Note that peak cytokine responses, observed in the previous figures, occurs concomitant with peak transgene expression.

Gene expression by plasmid admixed with polymer nanoparticles carrying prodrug and active TLR-7/8a. Polymer nanoparticles comprised of HPMA with either active adjuvant (PP-20×7/8a) or prodrug adjuvant (PP-R20×7/8a) were admixed with DNA plasmid administered intramuscularly into the thigh of BALB/c mice. Luciferase expression was monitored at serial time points and is shown in the top of FIG. 13. The bottom of FIG. 13 shows luciferase expression in mice that received the pro-drug adjuvant (PP-R20×7/8a) co-administered with the DNA plasmid expressing luciferase.

Figure 14:
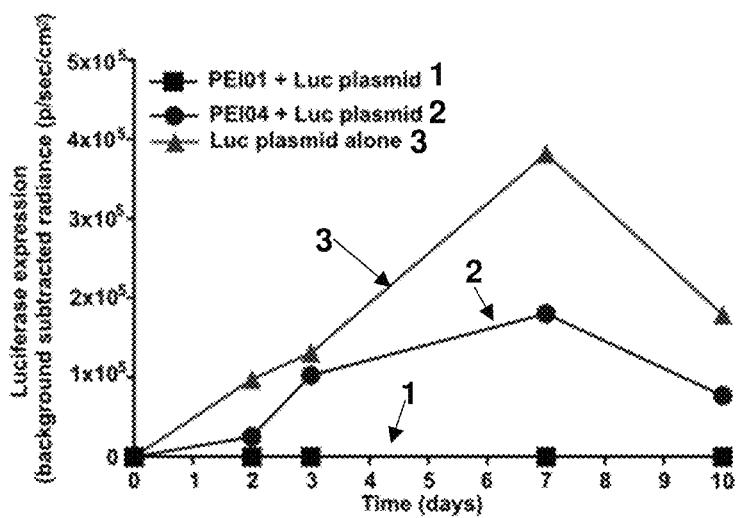
FIG. 14 shows that polymer nanoparticles comprised of PEI polymers linked to either active adjuvant (PEI01) or prodrug adjuvant (PEI04) and linked to a DNA plasmid and administered intramuscularly into the thigh of BALB/c mice leads to in vivo transgene expression. Luciferase expression was monitored at serial time points and is shown in the top of FIG. 14. Note that peak cytokine responses, observed in the previous figures, occurs concomitant with peak transgene expression.

Gene expression by plasmid linked to expression vector delivery systems carrying prodrug and active TLR-7/8a. Polymer nanoparticles comprised of PEI polymers with either active adjuvant (PEI01) or prodrug adjuvant (PEI04) were linked to a DNA plasmid and administered intramuscularly into the thigh of BALB/c mice. Luciferase expression was monitored at serial time points and is shown in the top of FIG. 14. The bottom of FIG. 14 shows luciferase expression in mice that received the expression vector delivery system linked with the pro-drug adjuvant (PEI04) linked to the DNA plasmid expressing luciferase.

Example 2

Figure 15A:
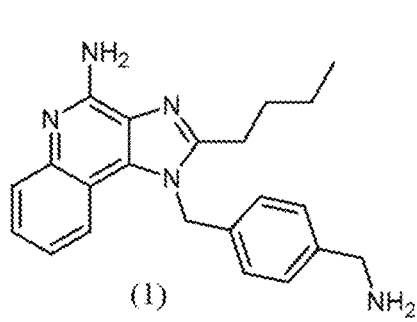
FIGS. 15A-15C illustrate the structure and in vivo activity of poly(basic) TLR-7/8 agonists. (15A) Polybasic TLR-7/8a, which can be linked through aryl amine or hydrazine to be used as a prodrug, were evaluated for the capacity to induce innate immune activation following subcutaneous footpad injection in mice. (15B, 15C) 5 nmol of each compound in 504 of PBS was administered into the hind footpads of mice. After 24 hours, (popliteal) lymph nodes draining the site of vaccine administration were harvested and mechanically disrupted to create a cell suspension that was cultured for 8 hours. The lymph node cell suspension supernatant was assessed for (15B) IP-10 and (15C) IL-12 by ELISA.
Figure 15A:
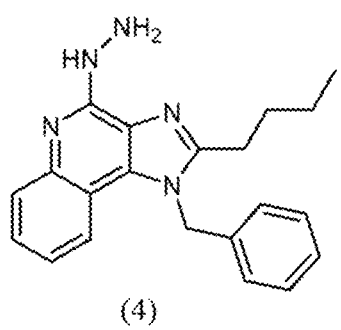
Figure 15A:
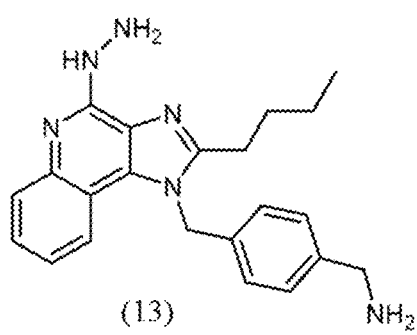
Figure 15A:
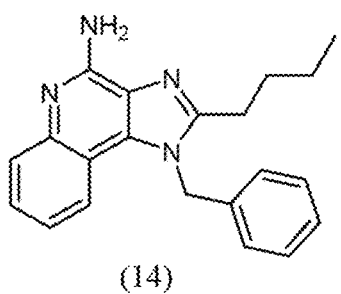
Figure 15A:
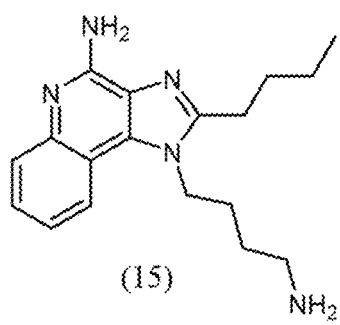
Figure 15A:
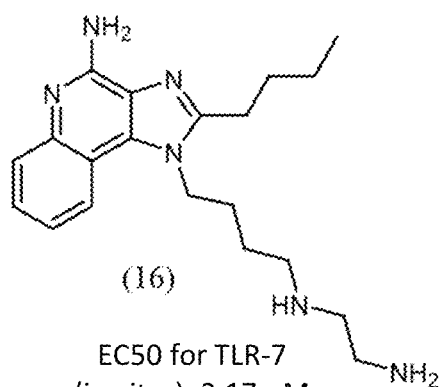
Figure 15B:
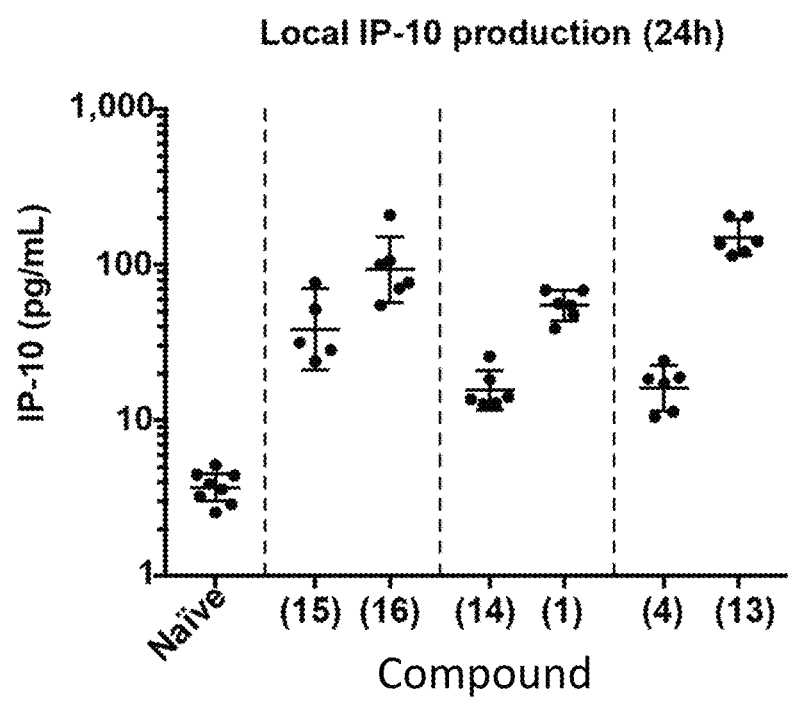
Figure 15C:
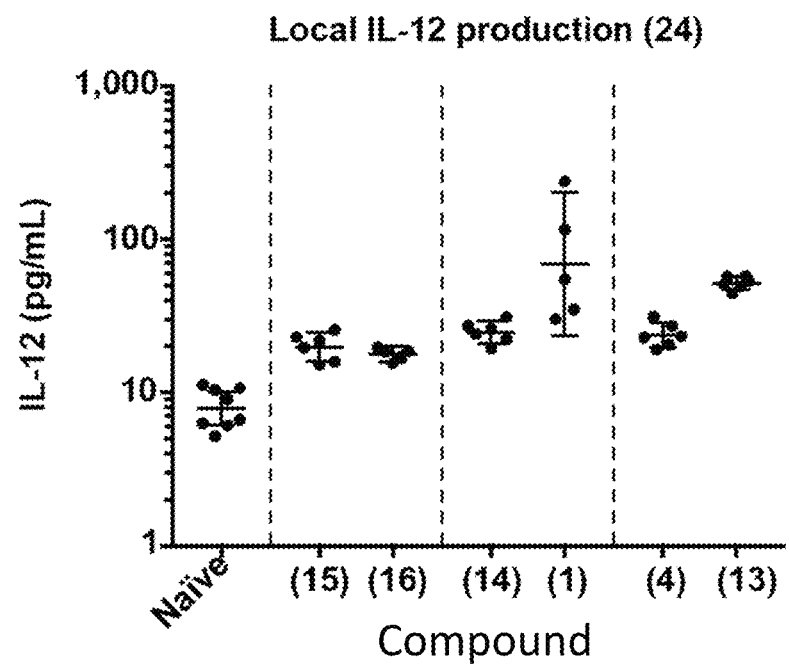
Figure 16A:
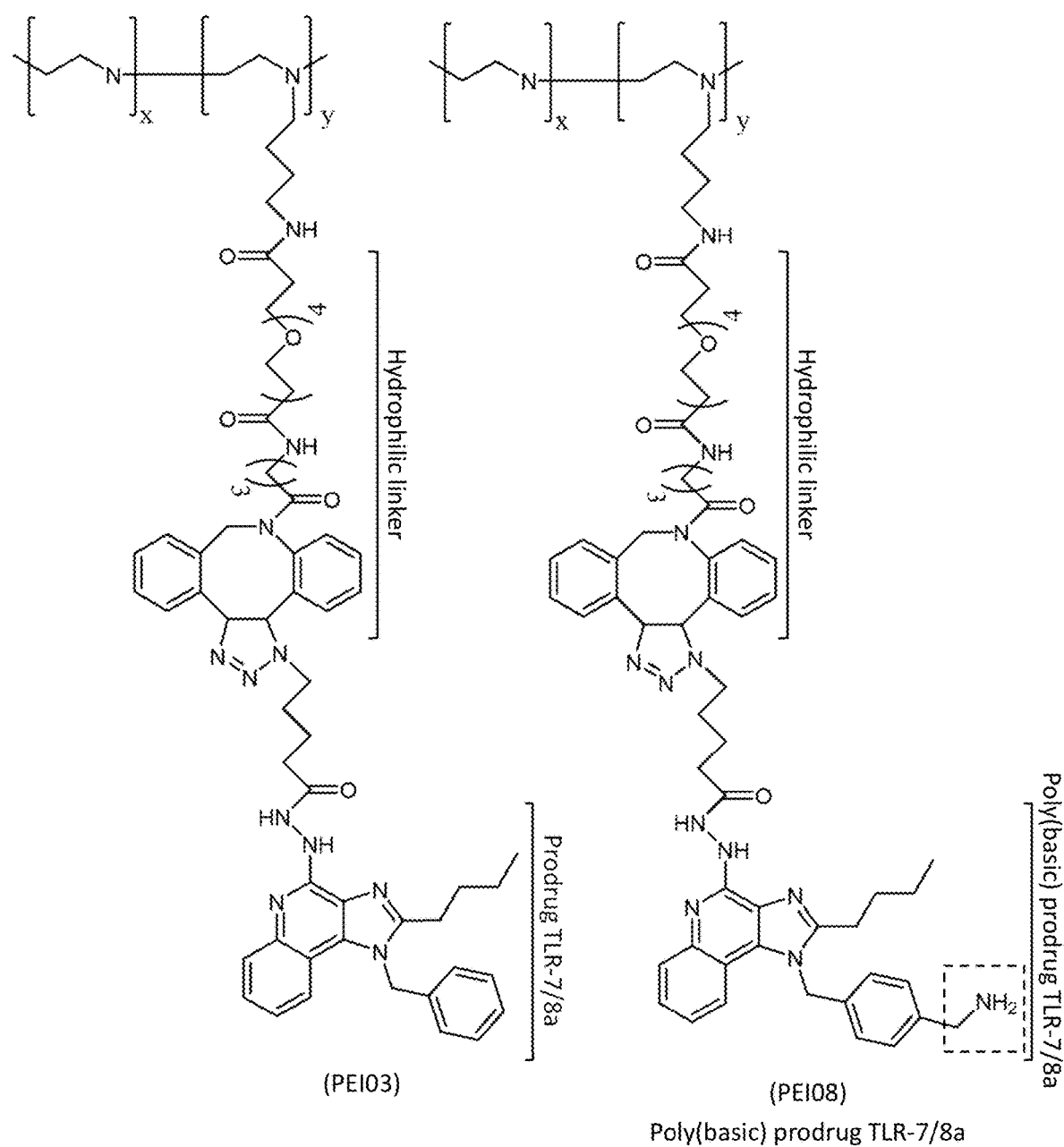
FIGS. 16A-16C show a set of molecular structures and graphs illustrating that gene expression delivery systems carrying poly(basic) prodrug TLR-7/8a induce higher magnitude and more durable immune activation those same systems delivering the monobasic TLR-7/8a analog. (16A and 16B) Chemical structures of mono-basic and di-basic prodrug Toll-like receptor 7/8 agonists. Hydrolysis of the labile bond results in the release of a free amine that is protonated and carries a positive charge at physiologic pH. The di-basic compound (right) is predicted to carry two positive charges at pH<8. (16C) Polymer nanoparticles comprised PEI (PEI03 and PEI08) based polymers were linked to the TLR-7/8a so as to block the C4-amine that is critical to activity. The polymer nanoparticles were administered subcutaneously into the hind footpads of C57BL/6 mice and lymph nodes were isolated at serial time points thereafter and cultured overnight. Supernatant from the ex vivo lymph node cell suspensions (n=4) were evaluated for IL-12 by ELISA.
Figure 16B:
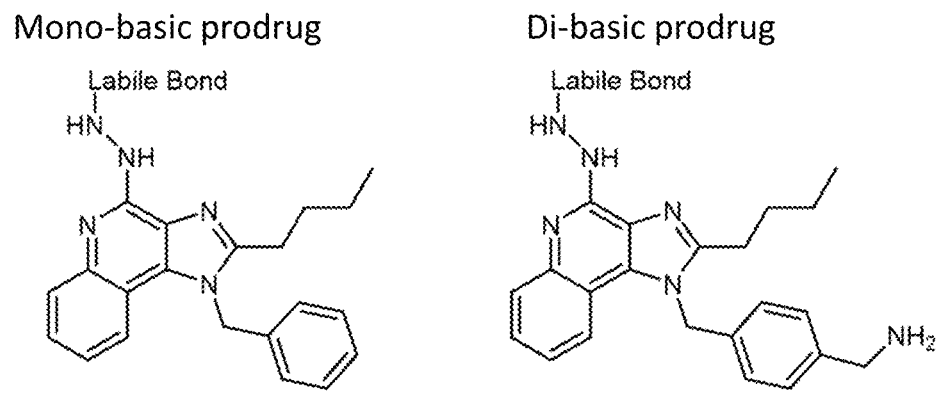
Figure 16C:
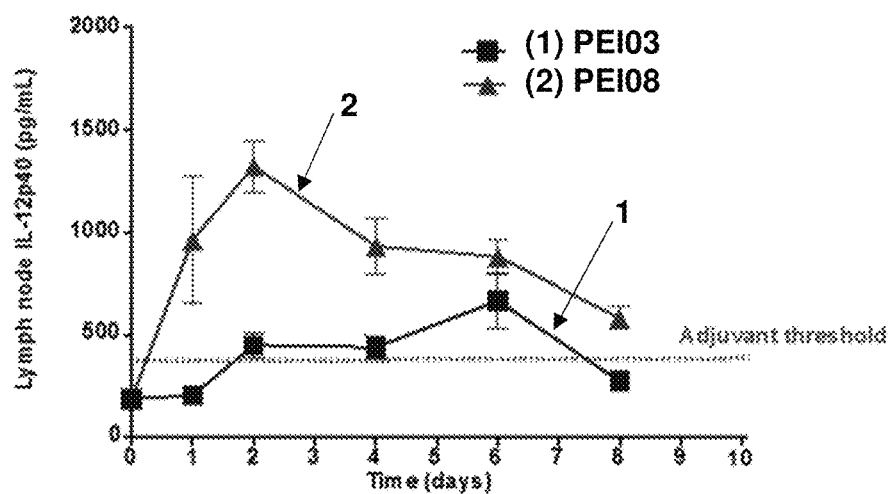

Prodrugs of Poly(Basic) TLR-7/8 Agonists Induce Immune Responses of Increased Magnitude and Duration Another unexpected finding is that the magnitude and duration of the activity induced by prodrug TLR-7/8a can be dependent on the poly(basic) character of the released TLR-7/8a. For example, in comparing two compositions of prodrug TLR-7/8a (FIG. 15B), the dibasic TLR-7/8a (right) provides higher magnitude and greater duration of immune activity as compared with the mono-basic compound. This finding is exemplified by FIG. 15, which shows that a PEI-based copolymer carrying a poly(basic) TLR-7/8a prodrug induces high magnitude immune activation as compared with the mono-basic prod-drug TLR-7/8a. Non-limiting explanations include that this finding is due to increased retention of the dibasic TLR-7/8a in the endosomal compartment of immune cells following hydrolysis of the chemically labile prodrug site, or may result from the 2+ charge on the di-basic molecule preventing membrane permeability and therefore leading to increased retention of the molecule in the draining lymphatics.

It will be apparent that the precise details of the methods or compositions described may be varied or modified without departing from the spirit of the described embodiments. We claim all such modifications and variations that fall within the scope and spirit of the claims below.

We claim:

1. A polymer linked to an adjuvant prodrug, wherein:

the polymer linked to the adjuvant prodrug forms polymer nanoparticles that enter immune cells under physiological conditions, and the adjuvant of the adjuvant prodrug comprises a functional moiety for adjuvant activity that is masked by linkage to a linker connected to the polymer, the linker comprises an enzyme-degradable labile bond, and cleavage of the enzyme-degradable labile bond by an intracellular enzyme unmasks the functional moiety and releases an active adjuvant;

wherein the adjuvant prodrug comprises a toll-like receptor 7/8 agonist comprising the structure set forth as one of:

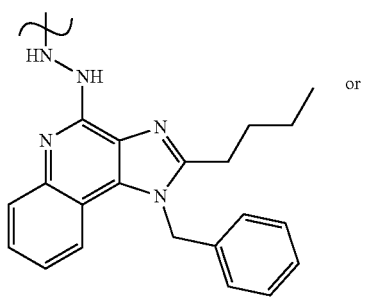

or

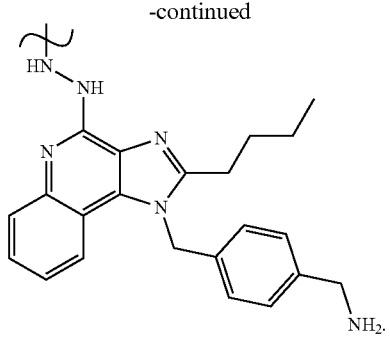

2. The polymer linked to the adjuvant prodrug of claim 1, wherein the enzyme is a cathepsin.

3. The polymer linked to the adjuvant prodrug of claim 1, wherein the linker comprises a cathepsin-cleavable peptide comprising L-amino acids or D-amino acids comprising the amino acid sequence set forth as one of: KPLR (SEQ ID NO: 2), KLRP (SEQ ID NO: 3), SLVR (SEQ ID NO: 4), or SLRV (SEQ ID NO: 5), and cathepsin cleavage of the peptide cleaves the labile bond to release the active adjuvant.

4. The polymer linked to the adjuvant prodrug of claim 1, wherein the polymer linked to the toll-like receptor 7/8 agonist comprises a structure set forth as one of compounds PEI04, PEI05, PEI06, PEI07, PL08, PL09, or PL10.

5. The polymer linked to the adjuvant prodrug of claim 1, wherein the polymer is a cationic polymer or a hydrophilic polymer.

6. The polymer linked to the adjuvant prodrug of claim 5, wherein
the cationic polymer is a poly(ethylenimine) polymer, a poly(lysine) polymer, or a poly(arginine) polymer; or
the hydrophilic polymer is a poly(N-(2-hydroxypropyl (methacrylamide))-based co-polymer.

7. The polymer linked to the adjuvant prodrug of claim 1, wherein the ratio of adjuvant prodrug to monomer of the polymer is from 1:100 to 1:1 mol/mol.

8. The polymer linked to the adjuvant prodrug of claim 1, wherein the ratio of adjuvant prodrug to monomer of the polymer is from 1:20 to 1:10 mol/mol.

9. The polymer linked to the adjuvant prodrug of claim 1, wherein the polymer comprises a plurality of monomers comprising from 5 monomers to 500 monomers.

10. The polymer linked to the adjuvant prodrug of claim 1, wherein the toll-like receptor 7/8 agonist comprises a structure set forth as:

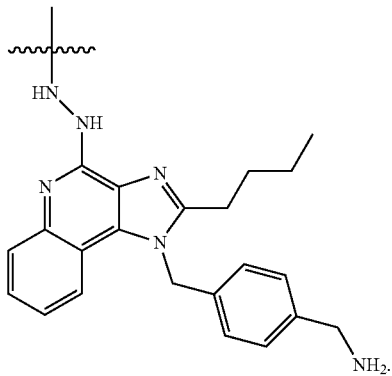 [SMILES: *NNc1nc2ccccc2c2c1nc(CCCC)n2Cc1ccc(CN)cc1]

11. An immunogenic composition, comprising the polymer linked to the adjuvant prodrug of claim 1; and an expression vector comprising a nucleic acid molecule operably linked to a promoter, wherein the nucleic acid molecule encodes an antigen of interest.

12. The immunogenic composition of claim 11, wherein the expression vector does not comprise any CpG motifs.

13. The immunogenic composition of claim 11, wherein the expression vector is a plasmid expression vector.

14. The immunogenic composition of claim 11, wherein the polymer is a cationic polymer and the expression vector is linked to the cationic polymer by an electrostatic interaction.

15. The immunogenic composition of claim 11, wherein the polymer, the expression vector, and the adjuvant prodrug form polymer nanoparticles in the immunogenic composition.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: peptide sequence

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: peptide sequence

<400> SEQUENCE: 2

Lys Pro Leu Arg
1

<210> SEQ ID NO 3
<211> LENGTH: 4
<212> TYPE: PRT
<213> ORGANISM: Artificial Sequence
<220> FEATURE:
<223> OTHER INFORMATION: peptide sequence

<400> SEQUENCE: 3
```

```
Lys Leu Arg Pro
1

<210> SEQ ID NO 4
<211> LENGTH: 4
<212> TYPE: PRT
<213> ORGANISM: Artificial Sequence
<220> FEATURE:
<223> OTHER INFORMATION: peptide sequence

<400> SEQUENCE: 4

Ser Leu Val Arg
1

<210> SEQ ID NO 5
<211> LENGTH: 4
<212> TYPE: PRT
<213> ORGANISM: Artificial Sequence
<220> FEATURE:
<223> OTHER INFORMATION: peptide sequence

<400> SEQUENCE: 5

Ser Leu Arg Val
1
```